US008466177B2

(12) United States Patent
Luo et al.

(10) Patent No.: US 8,466,177 B2
(45) Date of Patent: Jun. 18, 2013

(54) TREATING AND PREVENTING VIRAL INFECTIONS

(75) Inventors: Ming Luo, Birmingham, AL (US); Zhen Yang, Ridgewood, NJ (US)

(73) Assignee: The UAB Research Foundation, Birmingham, AL (US)

( * ) Notice: Subject to any disclaimer, the term of this patent is extended or adjusted under 35 U.S.C. 154(b) by 387 days.

(21) Appl. No.: 12/682,341

(22) PCT Filed: Oct. 31, 2008

(86) PCT No.: PCT/US2008/082140
§ 371 (c)(1),
(2), (4) Date: Jul. 14, 2010

(87) PCT Pub. No.: WO2009/059243
PCT Pub. Date: May 7, 2009

(65) Prior Publication Data
US 2010/0286212 A1    Nov. 11, 2010

Related U.S. Application Data

(60) Provisional application No. 60/984,601, filed on Nov. 1, 2007, provisional application No. 61/049,665, filed on May 1, 2008.

(51) Int. Cl.
*A61K 31/4439* (2006.01)
*A61K 31/426* (2006.01)
*A61K 31/427* (2006.01)
*C07D 277/36* (2006.01)
*C07D 277/34* (2006.01)
*C07D 417/06* (2006.01)

(52) U.S. Cl.
USPC ......... 514/342; 546/269.7; 514/369; 548/183

(58) Field of Classification Search
USPC ................ 548/183; 546/269.7; 514/342, 369
See application file for complete search history.

(56) References Cited

U.S. PATENT DOCUMENTS

| | | | |
|---|---|---|---|
| 3,345,334 | A | 10/1967 | Angelo |
| 4,293,563 | A | 10/1981 | Jamieson et al. |
| 5,523,314 | A | 6/1996 | Bue-Valleskey et al. |
| 5,661,168 | A | 8/1997 | Panetta et al. |
| 6,008,350 | A | 12/1999 | Roschger et al. |
| 7,009,048 | B2 | 3/2006 | Uehira et al. |
| 7,566,732 | B2 * | 7/2009 | Singh et al. ............ 514/369 |
| 2006/0276520 | A1 | 12/2006 | Singh et al. |
| 2006/0287319 | A1 | 12/2006 | Jiang et al. |

FOREIGN PATENT DOCUMENTS

| | | |
|---|---|---|
| WO | 00/10573 | 3/2000 |
| WO | 2004/024061 | 3/2004 |
| WO | 2005/041951 | 5/2005 |
| WO | 2007/045877 | 4/2007 |

OTHER PUBLICATIONS

Schafer et al. Drug Discovery Today 2008, 13 (21/22), 913-916.*
Medicines in Development for HIV/AIDS 2010.*
Horig et al., Journal of Translational Medicine 2004, 2(44).*
Mullin et al., "Increased amounts of the influenza virus nucleoprotein do not promote higher levels of viral genome replications," J Gen Virol., 85(12):3689-3698 (2004).
Muramoto et al., "Hierarchy among viral RNA (vRNA) segments in their role in vRNA incorporation into influenza A virions," J Virol. 80(5):2318-2325 (2006).
Noda et al., "Architecture of ribonucleoprotein complexes in influenza A virus particles," Nature 439(7075):490-492 (2006).
Obenauer et al., "Large-scale sequence analysis of avian influenza isolates," Science 311(5767):1576-1580 (2006).
Omar et al., "Nucleophilic addition to the exocyclic couble bond of 5-substituted 2-thioxo-4-oxothiazolidines," Egyptian Journal of Chemistry 47(1):75-92 (2004).
O'Neill et al., "Nuclear import of influenza virus RNA can be mediated by viral nucleoprotein and transport factors required for protein import," J Biol Chem 270(39):22701-22704 (1995).
Ortega et al., "Ultrastructural and functional analyses of recombinant influenza virus ribonucleoproteins suggest dimerization of nucleoprotein during virus amplification," J Virol 74(1):156-163 (2000).
Ott et al., "Effect of the virostatic Norakin (triperiden) on influenza virus activities," Antiviral Res. 24(1):37-42 (1994).
Park et al., "Preparation of a 990-member chemical compound library of hydantoin- and isoxazoline-containing heterocycles using multipin technology," J. Comb. Chem. 3(2):171-176 (2001).
Park et al., "Solution- and solid-phase synthesis of novel hydantoin and isoxazoline-containing heterocycles," Chemical Communications, 16:1679-1680 (1998).
Pons et al., "Isolation and characterization of the ribonucleoprotein of influenza virus," Virology 39:250-259 (1969).
Poole et al., "Functional domains of the influenza A virus PB2 protein: identification of NP- and PB-1 binding sites," Virology 321(1):120-133 (2004).
Portela et al., "The influenza virus nucleoprotein: a multifunctional RNA-binding protein pivotal to virus replication," J Gen Virol 83(4):723-734 (2002).
Powers et al., "SAR and mode of action of novel non-nucleoside inhibitors of hepatitis C NS5b RNA polymerase," J Med Chem. 49:1034-1046 (2006).
Prokudina et al., "Stability of intracellular influenza virus nucleocapsid protein oligomers," Arch Virol 150(4):833-839 (2005).
Prosch et al., "Mutations in the hemagglutinin gene associated with influenza virus resistance to norakin," Arch Virol 102(1-2):125-129 (1988).
Przegalinski, E., "Phamacological properties of some new hydantoin and thiohydantoin derivatives. I. General pharmacological screening," Dissertationes Pharmaceuticae et Pharmacologicae, 21 (2): 113-124 (1969).
Raulais et al., "Synthesis and characterization of phenylthiohydantoin derivatives of amino-acids protected in their side-chain functions, and their application for monitoring solid-phase peptide synthesis," Journal of Chemical Research, Synopses 1:11 (1978).

(Continued)

*Primary Examiner* — Jason M Nolan
(74) *Attorney, Agent, or Firm* — Kilpatrick, Townsend & Stockton LLP

(57) ABSTRACT

Compounds that are useful in treating or preventing viral infections, such as influenza, are described herein. Further described are compositions made from these compounds and methods for using the compounds and their compositions in treating or preventing viral infections.

18 Claims, 4 Drawing Sheets

OTHER PUBLICATIONS

Rodgers et al., "Purification, crystallization and preliminary X-ray crystallographic analysis of the nucleocapsid protein of Bunyamwera virus," Acta Crystallograph Sect F Struct Biol Cryst Commun. 62(4):361-364 (2006).

Rudolph et al., "Crystal structure of the borna disease virus nucleoprotein," Structure 11(10:1219-1226 (2003).

Ruigrok et al., "Structure of influenza virus ribonucleoprotein particles. II. Purified RNA-free influenza virus ribonucleoprotein forms structures that are indistinguishable from the intact influenza virus ribonucleoprotein particles," J Gen Virol. 76(4):1009-1014 (1995).

Saito et al., "Attenuation of a human H9N2 influenza virus in mammalian host by reassortment with an avian influenza virus," Arch Virol. 102(1-2):125-129 (1988).

Salomon et al., "The polymerase complex genes contribute to the high virulence of the human H5N1 influenza virus isolate A/Vietnam/1203/04," J Exp Med 203(3):689-697 (2006).

Scholtissek et al., "Analysis of influenza A virus nucleoproteins for the assessment of molecular genetic mechanisms leading to new phylogenetic virus lineages," Arch Virol., 131(3-4):237-250 (1993).

Shu et al., "Analysis of the evolution and variation of the human influenza A virus nucleoprotein gene from 1933 to 1990," J Virol. 67(5):2723-2729 (1993).

Sidwell et al., "Efficacy of orally administered T-705 on lethal avian influenza A (H5N1) virus infections in mice," Antimicrob Agents Chemother. 51(3):845-851 (2007).

Sidwell et al., "In vivo influenza virus-inhibitory effects of the cyclopentane neuraminidase inhibitor RJW-270201," Antimicrob Agents Chemother. 45(3):749-757 (2001).

Smirnov et al., "Action of hydrolytic enzymes on influenza virus A ribonucleoprotein," Vopr Virusol., Jul.-Aug. (4):477-481 (1981).

Solorzano et al., "Mutations in the NS1 protein of swine influenza virus impair anti-interferon activity and confer attenuation in pigs," J Virol. 79(12):7535-7543 (2005).

Staschke et al., "Inhibition of influenza virus hemagglutinin-mediated membrane fusion by a compound related to podocarpic acid," Virology 248(2):264-274 (1998).

Stevens et al., "Structure and receptor specificity of the hemagglutinin from an H5N1 influenza virus," Science 312 (5772):404-410 (2006).

Stray et al., "A heteroaryldihydropyrimidine activates and can misdirect hepatitis B virus capsid assembly," Proc Natl Acad Sci USA 102(23);8138-8143 (2005).

Tai et al., "Characterization of human influenza virus varients selected in vitro in the presence of the neuraminidase inhibitor GS 4071," Antimicrob Agents Chemother. 42(12):3234-3241 (1998).

Tchatalbachev et al., "The packaging signal of influenza viral RNA molecules," RNA 7(7):979-989 (2001).

Thoennes et al., "Analysis of residues near the fusion peptide in the influenza hemagglutinin structure for roles in triggering membrane fusion," Virology 370(2):403-414 (2008).

Tompkins et al., "Recombinant parainfluenza virus 5 (PIV5) expressing the influenza A virus hemagglutinin provides immunity in mice to influenza A virus challenge," Virology 362(1):139-150 (2007).

Velu et al., "Tethered dimer inhibitors of NAD synthetase: parallel synthesis of an aryl-substituted SAR library," J Comb Chem, 7(6):898-904 (2005).

Vreede et al., "Model suggesting that replication of influenza virus is regulated by stabilization of replicative intermediates," J Virol. 78(17):9568-9572 (2004).

Wang et al., "Dexamethasone as a chemoprotectant in cancer chemotherapy: hematoprotective effects and altered pharmacokinetcs and tissue distribution of carboplatin and gemcitabine," Cancer Chemother Pharmacol 53(6):459-467 (2004).

Wang et al., "Immunomodulatory oligonucleotides as novel therapy for breast cancer: pharmacokinetics, in vitro and in vivo anticancer activity, and potentiation of antibody therapy," Mol Cancer Ther. 5(8):2106-2114 (2006).

Wang et al., "The NPI-1/NPI-3 (karyppherin alpha) binding site on the influenza a virus nucleoprotein NP is a nonconventional nuclear localization signal," J. Virol. 71(3):1850-1856 (1997).

Whittaker, G.R., "Intracellular trafficking of influenza virus: clinical implications for molecular medicine," Expert Reviews in Molecular Medicine, Feb. 8 1-13 (2001).

Yano et al., "Synthetic inhibitors of cytochrome-P-450 2A6: Inhibitory activity, difference spectra, mechanism of inhibition, and protein cocrystallization," J. Med. Chem. 49:6987-7001 (2006).

Yoshimoto et al., "Identification of amino acids of influenza virus HA responsible for resistance to a fusion inhibitor, Stachyflin," Microbiol Immunol 44(8):677-685 (2000).

Abou El-Regal et al., "Synthesis of new thiohydantoin derivatives under phase transfer catalysis," Phosphorus, Sulfur, and Silicon and the Related Elements, 182(4):845-851 (2007).

Albo et al., "Identification of an RNA binding region within the N-terminal third of the influenza A virus nucleoprotein," J Virol. 69(6):3799-3806 (1995).

Area et al., "3D structure of the influenza virus polymerase complex: localization of subunit domans," Proc Natl Acad Sci USA 101(1):308-313 (2004).

Bantia et al., "Anti-influenza virus activity of peramivir in mice with single intramuscular injection," Antiviral Research 69(1):39-45 (2006).

Baudin et al., "Structure of influenza virus RNP. 1. Influenza virus nucleoprotein melts secondary structure in panhandle RNA and exposes the bases to the solvent," EMBO J. 13(13):3158-3165 (1994).

Biswas et al., "Influenza virus nucleoprotein interacts with influenza virus polymerase proteins," J Virol. 72 (7):5493-5501 (1998).

Bodian et al., "Inhibition of the fusion-inducing conformational change of influenza hemagglutinin by benzoquinones and hydroquinones," Biochemistry, 32(12):2967-2978 (1993).

Chang et al., "pH-dependence of intermediate steps of membrane fusion induced by the influenza fusion peptide," Biochem J., 396(3):557-563, (2006).

Cianci et al., "Antiviral activity and molecular mechanism of an orally active respiratory syncytial virus fusion inhibitor," J. Antimicrob Chemother. 55(3):289-292 (2005).

Cianci et al., "Orally active fusion inhibitor of respiratory syncytial virus," Antimicrob Agents Chemother., 48 (2):413-422 (2004).

Compans et al., "Structure of the ribonucleoprotein of influenza virus," J Virol., 10(4):795-800 (1972).

Cros et al., "An unconventional NLS is critical for the nuclear import of the influenza A virus nucleoprotein and ribonucleoprotein," Traffic 6(3):205-213 (2005).

Cross, K. et al., "Mechanisms of cell entry by influenza virus," Expert Reviews in Molecular Medicine, Aug. 6 1-18 (2001).

Dalton et al., "Temperature sensitive influenza A virus genome replication results from low thermal stability of polymerase-cRNA complexes," Virol J. 3:58 (2006).

Deres et al., "Inhibition of hepatitis B virus replication by drug-induced depletion of nucleocapsids," Science, 299 (5608):893-896 (2003).

Ding et al., "Crystallization and preliminary X-ray analysis of a proteinase-K-resistant domain within the phosphoprotein of vesicular stomatitis virus (Indiana)," Acta Crystallogr D Biol Crystallogr. 60(Pt 11):2087-2090 (2004).

Dos Santos Afonso et al., "The generation of recombinant influenza A viruses expressing a PB2 fusion protein requires the conservation of a packaging signal overlapping the coding and noncoding regions at the 5' end of the PB2 segment," Virology 341(1):34-46 (2005).

Eisenberg et al., "Penetration of GS4071, a novel influenza neuraminidase inhibitor, into rat bronchoalveolar lining fluid following oral administration of the prodrug GS4104," Antimicrob. Agents Chemother. 41(9):1949-1952 (1997).

Epstein et al., "Protection against multiple influenza A subtypes by vaccination with highly conserved nucleoprotein," Vaccine 23(46-47):5404-5410 (2005).

Finley et al., "Novel aromatic inhibitors of influenza virus neuraminidase make selective interactions with conserved residues and water molecules in the active site," J Mol Biol. 293(5)1107-1119 (1999).

Frey et al., "Small molecules that bind the inner core of gp41 and inhibit HIV envelope-mediated fusion," Proc Natl Acad Sci USA 103(38):13938-13943 (2006).

Fujii et al., "Importance of both the coding and the segment-specific noncoding regions of the influenza A virus NS segment for its efficient incorporation into virions," J Virol. 79(6):3766-3774 (2005).

Ghedin et al., "Large-scale sequencing of human influenza reveals the dynamic nature of viral genome evolution," Nature, 437(7062):1162-1166 (2005).

Ghendon et al., "Haemagglutinin of influenza A virus is a target for the antiviral effect of Norakin," J Gen Virol 67(6):1115-1122 (1986).

Green et al., "Structure of the vesicular stomatitis virus nucleoprotein-RNA complex," Science 313(5785):357-360 (2006).

Green et al., "Study of the assembly of vesicular stomatitis virus N protein: role of the P protein," J. Virol. 74 (20):9515-9524 (2000).

Han et al., "Membrane structure and fusion-triggering conformational change of the fusion domain from influenza hemagglutinin," Nat Struct Biol 8(8):715-720 (2001).

Hayden et al., "Efficacy and safety of the neuraminidase inhibitor zanamivir in the treatment of influenza virus infections. GG167 Influenza Study Group." N Engl J Med 337(13):874-880 (1997).

Heider et al., "The influence of Norakin on the reproduction of influenza A and B viruses," Arch Virol., 86 (3-4):283-290 (1985).

Herlocher et al., "Sequence comparisons of A/AA/6/60 influenza viruses: mutations which may contribute to attenuation," Virus Res. 42(1-2):11-25 (1996).

Hoffman et al., "Structure-based identification of an inducer of the low-pH conformational change in the influenza virus hemagglutinin: irreversible inhibition of infectivity," J Virol 71(11):8808-8820 (1997).

Honda et al, "RNA polymerase of influenza virus: role of NP in RNA chain elogantion," J Biochem 104(6):1021-1026 (1988).

Huang et al., "Protonation and stability of the globular domain of influenza virus hemagglutinin," Biophys J. 82(2):1050-1058 (2002).

Jiang et al., "N-substituted pyrrole derivatives as novel human immunodeficiency virus type 1 entry inhibitors that interfere with the gp41 six-helix bundle formation and block virus fusion," Antimicrob Agents Chemother 48 (11):4349-4359 (2004).

Kati, M. et al., "In Vitro Characterization of A-315675 a Highly Potent Inhibitor of A and B Strain Influenza Virus Neuraminidases and Influenza Virus Replication," Antimicrobial Agents and Chemotherapy, 46(4): 1014-1021 (2002).

Kingsbury et al., "Assembly of influenza ribonucleoprotein in vitro using recombinant nucleoprotein," Virology 156(2): 396-403 (1987).

Klumpp et al., "Roles of the influenza virus polymerase and nucleoprotein in forming a functional RNP structure," EMBO J. 16(6):1248-1257 (1997).

Kobasa et al., "Enhanced virulence of influenza A viruses with the haemagglutinin of the 1918 pandemic virus," Nature 431(7009):703-707 (2004).

Kobayashi et al., "Molecular dissection of influenza virus nucleoprotein: deletion mapping of the RNA binding domain," J Virol. 68(12):8433-8436 (1994).

Lai et al., "Locking the kink in the influenza hemagglutinin fusion domain structure," J Biol Chem., 282 (33):23946-23956 (2007).

Lavillette et al., "Hepatitis C virus glycoproteins mediate low pH-dependent membrane fusion with liposomes," J Biol Chem. 281(7):3909-3917 (2006).

Liang et al., "cis-Acting packaging signals in the influenza virus PB1, PB2, and PA genomic RNA segments," J Virol. 79(16):10348-10355 (2005).

Liu et al., "Attenuating mutations of the matrix gene of influenza A/WSN/33 virus," J Virol. 79(3):1918-1923 (2005).

Luan et al., "High-throughput expression of C. elegans proteins," Genome Research 14(10B):2102-2110 (2004).

Luo et al., "Characterization of a hemagglutinin-specific inhibitor of influenza A virus," Virology 226(1):66-76 (1996).

Luo, G. et al., "Molecular mechanism underlying the action of a novel fusion inhibitor of influenza A virus," Journal of Virology, 71(5):4062-4070 (1997).

Luo, M., "Antiviral drugs fit for a purpose," Nature, 443(7):37-38 (2006).

Manfredi et al., "A novel antiretroviral class (fusion inhibitors) in the management of HIV infection. Present features and future perspectives of enfuvirtide (T-20)," Curr Med Chem 13(20):2369-2384 (2006).

Mittra et al., "Michael addition of pyrazaolone and thiazolidone to bis- and cyclopropane derivatives: their fungitoxicity study," Acta Ciencia Indica, Chemistry 11(4):267-272 (1985).

Mittra et al., "Synthesis of quinazolone and benzimidazole and their derivatives as potential fungicides," Acta Ciencia Indica, Chemistry 9(1-4):109-112 (1983).

* cited by examiner

TREATING AND PREVENTING VIRAL INFECTIONS

CROSS-REFERENCE TO PRIORITY APPLICATIONS

This application claims priority to U.S. Provisional Application Nos. 60/984,601, filed Nov. 1, 2007 and 61/049,665, filed May 1, 2008, both of which are incorporated herein by reference in their entirety.

STATEMENT REGARDING FEDERALLY FUNDED RESEARCH

This invention was made with government support under Grant No. 5U54AI057157-04 awarded by the National Institutes of Health. The U.S. government has certain rights in this invention.

BACKGROUND

Influenza viruses commonly infect the upper respitory tract of mammals, including humans, pigs, horses, mink, seals, and whales. Influenza viruses can also have gastrointestinal tropism in bird species. Seasonal epidemics of flu generally occur after January and typically affect 10-20% of the general human population. Influenza viruses are members of the Orthomyxoviridae family of RNA viruses. Such viruses are commonly referred to as enveloped viruses. The three types of influenza viruses are A, B, and C. Most animal species can be infected with Influenza A. Influenza B and C were once thought to only infect humans, but researchers have recently discovered seals can be infected with Influenza B.

It is well known that influenza viruses can mutate and form new strains from season to season. New strains in human populations typically develop from other animal species (e.g., birds). Viral transmission from birds to animals is thought to proceed through an intermediate animal (e.g., swine), since human and avian influenza viruses are quite different. Occasionally, however, avian to human transmission can occur.

Any subject can be susceptible to influenza viral infection (even healthy subjects), and serious problems from influenza can happen at any age. While most subjects who get influenza will recover in a few days to less than 2 weeks, some subjects can develop complications (e.g., pneumonia, bronchitis, and sinus and ear infections) or experience exacerbation of chronic health problems such as asthma or chongestive heart failure. Such complications and exacerbation of chronic health problems can lead to the death of an infected subject. The infamous influenza pandemic of 1918-1919, for example, killed an estimated 20-40 million people worldwide. Further, in non-pandemic years, an average of about 36,000 people per year in the United States die from influenza, and more than 200,000 have to be admitted to the hospital as a result of influenza. As influenza is caused by a virus, antibiotics (e.g., penicillin) do not treat the infection. The current method of preventing the flu is to get an influenza vaccine annually, prior to flu season.

The influenza A virus particle or virion is 80-120 nm in diameter. Unusual for a virus, the influenza A genome is not a single piece of nucleic acid; instead, it contains eight pieces of segmented negative-sense RNA (13.5 kilobases total), which encode 10 proteins (HA (hemagglutinin), NA (neuraminidase), NP (nucleoprotein), M1, M2, NS1, PA, PB1, PB1-F2, PB2). Hemagglutinin and neuraminidase are two large glycoproteins found on the outside of the viral particles. Neuraminidase is an enzyme involved in the release of progeny virus from infected cells by cleaving sugars that bind the mature viral particles. By contrast, hemagglutinin is a lectin that mediates binding of the virus to target cells and entry of the viral genome into the target cell. Because a virus must bind to the target cell, inhibition of viral binding prevents infection.

The ability of a virus (e.g., influenza) to overtake the replication infrastructure of a host cell and effect virus replication begins with recognition by the virus of certain receptors on the host cell's membrane. This process can be mediated by a surface protein or multiple surface proteins on the virion, e.g., hemagglutinin (HA) of influenza virus. Once HA is synthesized on membrane bound ribosomes, its polypeptide chain is eventually cleaved into two chains of 328 and 221 amino acids known as $HA_1$ and $HA_2$, which can be held together by disulfide bonds. Three HA monomers (each with one $HA_1$ and $HA_2$) can trimerize and be transported to the plasma membrane, where the $HA_2$ tails anchor the monomers to the membrane, with the large part of the monomers protruding outside of the membrane. It is believed that about 20 residues at the N-terminal end of $HA_2$ are associated with the mechanism by which virus particles penetrate a host cell. This N-terminal portion is known as the fusion peptide.

Influenza viruses bind through hemagglutinin onto sialic acid sugars on the surfaces of epithelial cells. The predominant type of sialic acids is N-acetylneuraminic acid (Neu5Ac). Two types of sialic acids, Neu5Ac $\alpha(2,3)$-Gal and Neu5Ac $\alpha(2,6)$-Gal, both of which can be recognized as a receptor by influenza viruses, are important for viral infection of cells. Once a virus recognizes the sialic acids, cell fusion is then necessary to complete the transfer of the influenza genome into the target cell.

The cell imports the virus by endocytosis. In the acidic endosome, part of the hemagglutinin protein fuses the viral envelope with the vacuole's membrane, thus releasing the viral RNA (vRNA) molecules, accessory proteins and RNA-dependent RNA transcriptase into the cytoplasm.

HA functions in at least two known roles during viral infection. First, HA binds to the cell, and second, HA acts as a membrane fusogen. HA protein binds to sialic acid residues of glycosylated receptor molecules on target cell surfaces. Once bound, the virus can then enter the cell through endocytosis. The sialic acid binding site has been shown by X-ray crystallography to be located at the tip of an HA subunit within the jelly roll motif.

SUMMARY

Compounds useful for treating and/or preventing viral infections such as, for example, Influenza type A, Influenza type B, as well as other viruses, for example, HIV, as well as methods of making and using these compounds are described. Also described are compositions that are effective as a treatment against influenza and other viral infection, for example, as a method for inoculating a subject against influenza virus infection. Further described are methods for treating influenza and other viral infections and for inhibiting fusion mediated by hemagglutinin from the influenza and other virions.

One class of compounds useful in treating and/or preventing viral disorders comprises compounds of the following formula:

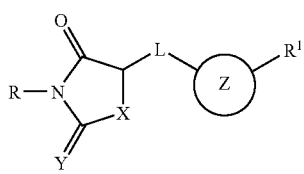

and includes pharmaceutically acceptable salts and prodrugs thereof. In this class of compounds, R is selected from a substituted or unsubstituted fused or bicyclic cycloalkyl ring; X is S or NH; Y is O or S; Z is selected from a substituted or unsubstituted 5-member heteroaryl ring, 6-member heteroaryl ring, or phenyl; $R^1$ is selected from a substituted or unsubstituted aryl or heteroaryl ring; and L is a direct bond or a substituted or unsubstituted linking unit, the linking unit having 1 to 4 carbon atoms and up to 2 heteroatoms selected from oxygen, nitrogen, and sulfur.

Another class of compounds useful in treating and/or preventing viral disorders comprises compounds of the following formula:

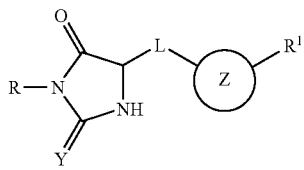

and includes pharmaceutically acceptable salts and prodrugs thereof. In this class of compounds, R is a substituted or unsubstituted cycloalkyl ring having 3 to 14 carbon ring atoms; Y is O or S; Z is selected from a substituted or unsubstituted 5-member heteroaryl ring, 6-member heteroaryl ring, or phenyl; $R^1$ is selected from a substituted or unsubstituted aryl or heteroaryl ring; and L is a direct bond or a substituted or unsubstituted linking unit, the linking unit having 1 to 4 carbon atoms and up to 2 heteroatoms selected from oxygen, nitrogen, and sulfur.

Further described herein are methods for treating or preventing a viral infection in a subject. These methods include administering to the subject an effective amount of one or more of the compounds or compositions described herein.

Also described herein are methods of inhibiting viral entry into a cell. These methods include administering to the cell an effective amount of one or more of the compounds or compositions described herein.

Additionally described herein are methods of inhibiting viral mediated membrane fusion. These methods include administering to the cell an effective amount of one or more of the compounds or compositions described herein.

Also described herein are methods of destabilizing a viral fusion protein. These methods include administering to a virally infected cell an effective amount of one or more of the compounds or compositions described herein.

DETAILED DESCRIPTION

Figure 1:
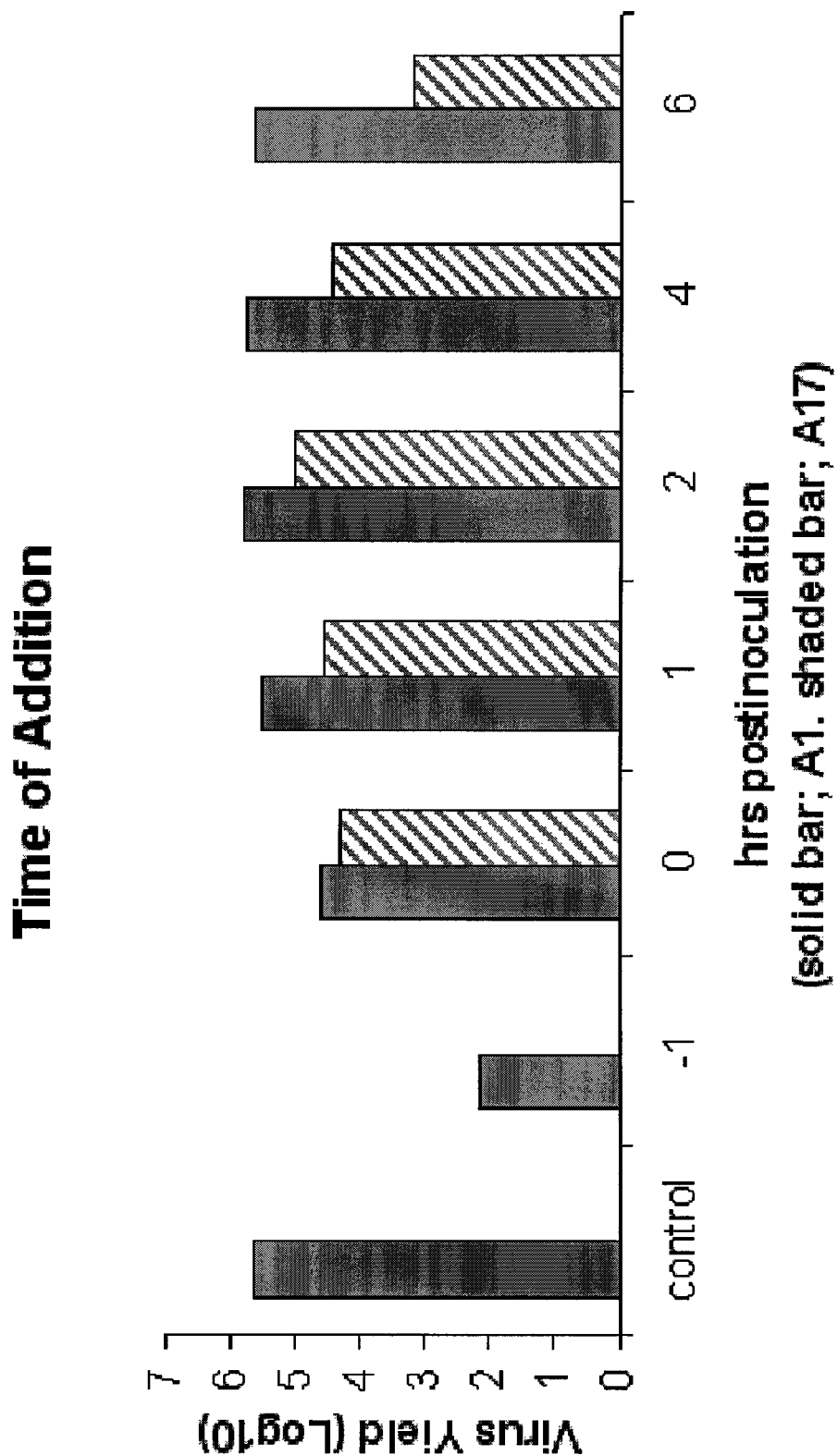
FIG. 1 depicts the results of a yield reduction assay when the inhibitor A1 was added to MDCK cells at different times post infection.

Compounds, compositions and methods useful in the treatment and/or prevention of viral infections such as, for example, Influenza type A, Influenza type B, as well as other viruses, for example, HIV, as well as methods of making and using these compounds are disclosed. These compounds block the hemagglutinin binding and/or fusion process involved in viral infection. Further described are compositions that are effective as a treatment against influenza virus infection, for example, as a method for inoculating a subject against influenza virus infection.

The compounds described herein have the formula:

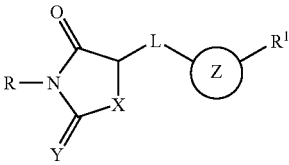

or a pharmaceutically acceptable salt or prodrug thereof, wherein R is selected from a substituted or unsubstituted cycloalkyl ring having from 3 to 14 carbon ring atoms;

X is S or NH;

Y is O or S;

Z is selected from:

i) a substituted or unsubstituted 5-member heteroaryl ring;

ii) a substituted or unsubstituted 6-member heteroaryl ring; or iii) a substituted or unsubstituted phenyl;

$R^1$ is selected from a substituted or unsubstituted aryl or heteroaryl ring; and L is a direct bond or a substituted or unsubstituted linking unit, the linking unit having 1 to 4 carbon atoms and up to 2 heteroatoms selected from oxygen, nitrogen, and sulfur.

One category of the compounds described herein relates to 3-N-cycloalkyl-5-substituted-2-thioxothiazolidin-4-ones having the formula:

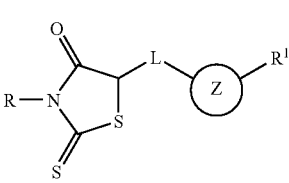

A first aspect of this category of the compounds described herein relates to Z rings that are 5-member ring heteroaryl rings having the formula:

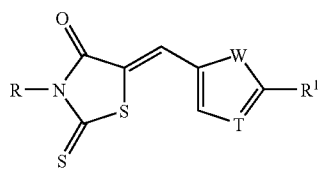

wherein W is O, S, or NH; T is CH or N.

One iteration of this aspect relates to Z rings comprising a single heteroatom chosen from O or S, the compounds having the formula:

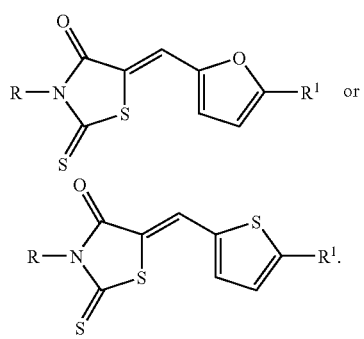

Another iteration of this aspect of the compounds described herein relates to compounds having the formula:

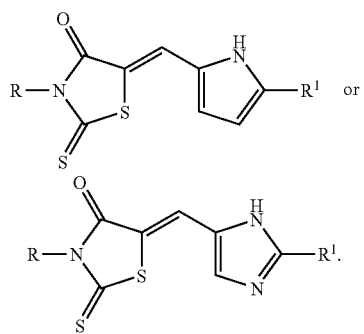

A yet further iteration of this aspect of the compounds described herein relates to compounds having the formula:

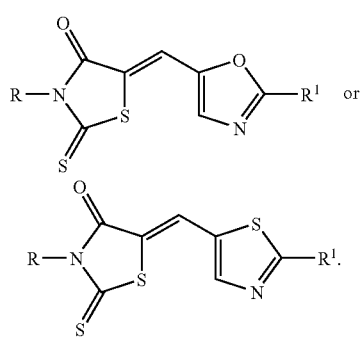

Another aspect of this category relates to Z rings that are 6-member heteroaryl rings having the formula:

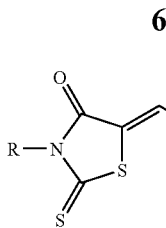

wherein $A^1$, $A^2$, $A^3$, $A^4$, and $A^5$ are each independently CH or N, such that at least one of $A^1$, $A^2$, $A^3$, $A^4$, and $A^5$ is a N.

One iteration of this aspect relates to compounds having the formula:

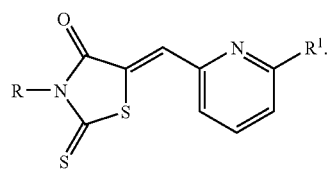

Another iteration of this aspect relates to compounds having the formula:

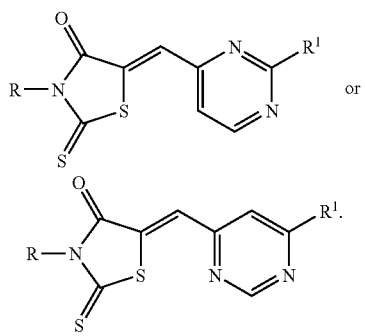

A further iteration of this aspect relates to compounds having the formula:

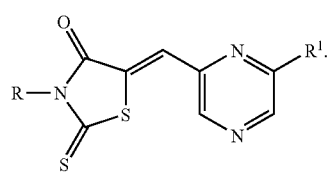

A further aspect of this category relates to Z rings that are phenyl rings having the formula:

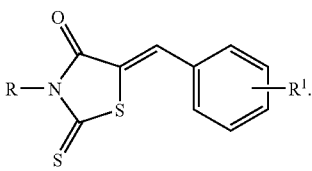

Another category of the compounds described herein relates to 3-N-cycloalkyl-5-substituted-thiazolidine-2,4-diones having the formula:

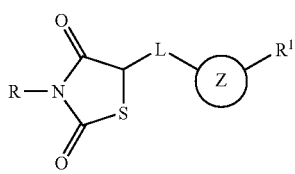

A first aspect of this category of the compounds described herein relates to Z rings that are 5-member ring heteroaryl rings having the formula:

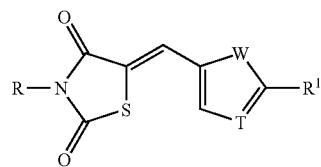

wherein W is O, S, or NH; T is CH or N.

One iteration of this aspect relates to Z rings comprising a single heteroatom chosen from O or S, the compounds having the formula:

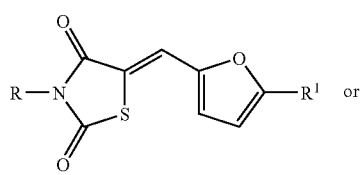

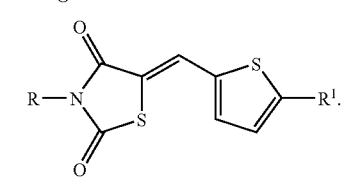

Another iteration of this aspect of the compounds described herein relates to compounds having the formula:

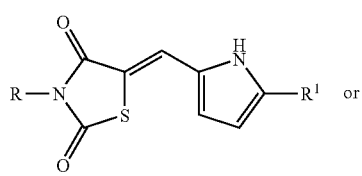

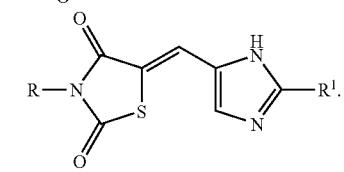

A yet further iteration of this aspect of the compounds described herein relates to compounds having the formula:

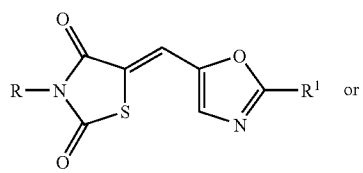

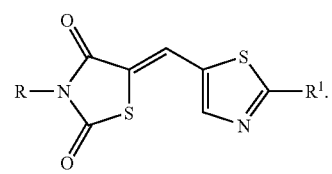

Another aspect of this category relates to Z rings that are 6-member ring heteroaryl rings having the formula:

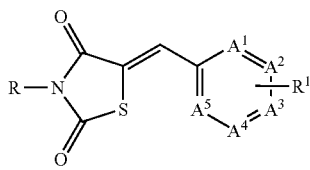

wherein $A^1$, $A^2$, $A^3$, $A^4$, and $A^5$ are each independently CH or N, such that at least one of $A^1$, $A^2$, $A^3$, $A^4$, and $A^5$ is a N.

One iteration of this aspect relates to compounds having the formula:

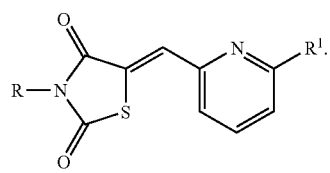

Another iteration of this aspect relates to compounds having the formula:

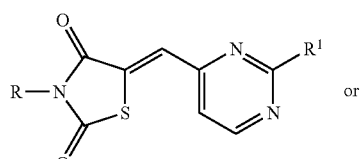

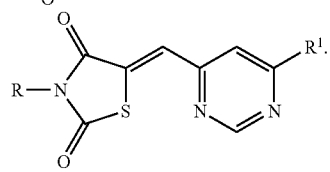

A further iteration of this aspect relates to compounds having the formula:

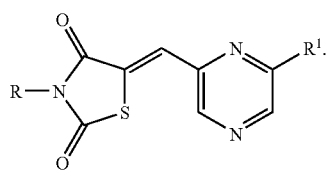

A further aspect of this category relates to Z rings that are phenyl rings having the formula:

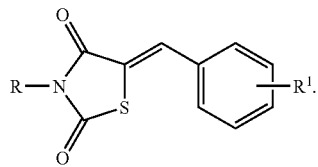

A further category of the compounds described herein relates to 3-N-cycloalkyl-5-substituted-2-thioxoimidazolidin-4-ones having the formula:

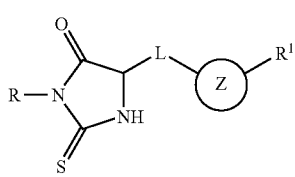

A first aspect of this category of the compounds described herein relates to Z rings that are 5-member ring heteroaryl rings having the formula:

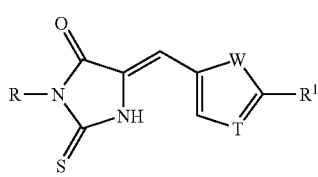

wherein W is O, S, or NH; T is CH or N.

One iteration of this aspect relates to Z rings comprising a single heteroatom chosen from O or S, the compounds having the formula:

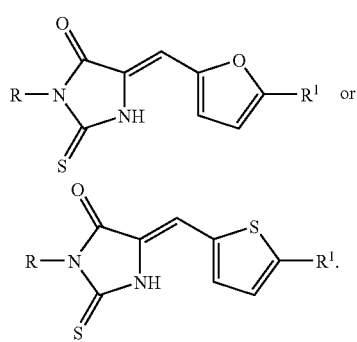

Another iteration of this aspect of the compounds described herein relates to compounds having the formula:

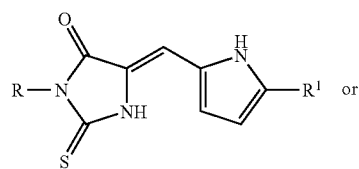

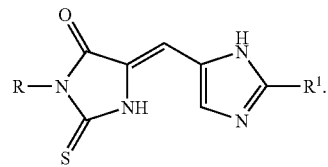

A yet further iteration of this aspect of the compounds described herein relates to compounds having the formula:

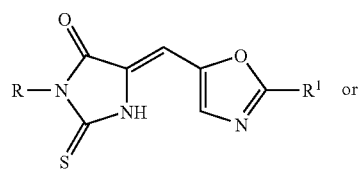

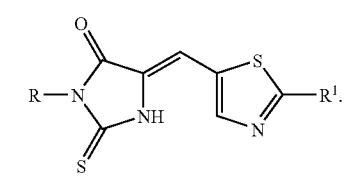

Another aspect of this category relates to Z rings that are 6-member ring heteroaryl rings having the formula:

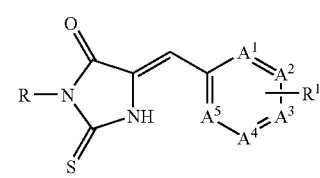

wherein $A^1$, $A^2$, $A^3$, $A^4$, and $A^5$ are each independently CH or N, such that at least one of $A^1$, $A^2$, $A^3$, $A^4$, and $A^5$ is a N.

One iteration of this aspect relates to compounds having the formula:

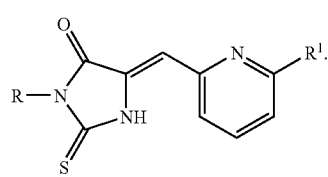

Another iteration of this aspect relates to compounds having the formula:

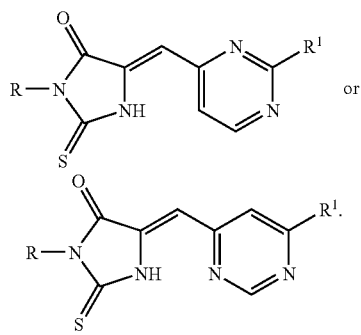

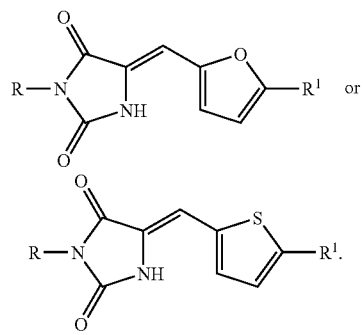

A further iteration of this aspect relates to compounds having the formula:

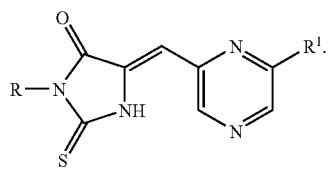

A further aspect of this category relates to Z rings that are phenyl rings having the formula:

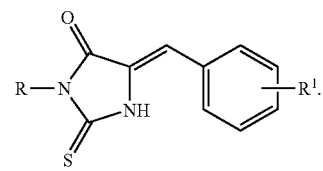

A still further category of the compounds described herein relates to 3-N-cycloalkyl-5-substituted-imidazolidine-2,4-diones having the formula:

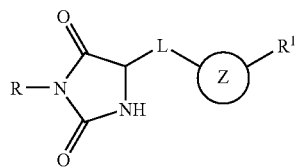

A first aspect of this category of the compounds described herein relates to Z rings that are 5-member ring heteroaryl rings having the formula:

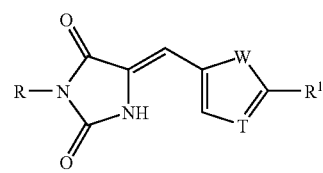

wherein W is O, S, or NH; T is CH or N.

One iteration of this aspect relates to Z rings comprising a single heteroatom chosen from O or S, the compounds having the formula:

Another iteration of this aspect of the compounds described herein relates to compounds having the formula:

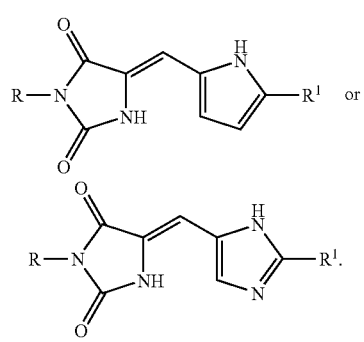

A yet further iteration of this aspect of the compounds described herein relates to compounds having the formula:

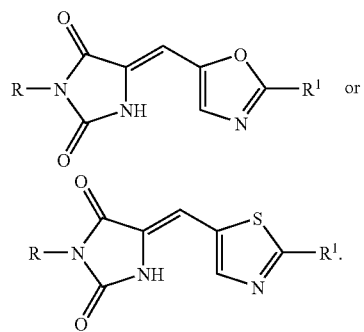

Another aspect of this category relates to Z rings that are 6-member ring heteroaryl rings having the formula:

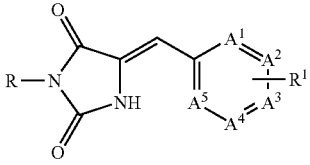

wherein $A^1$, $A^2$, $A^3$, $A^4$, and $A^5$ are each independently CH or N, such that at least one of $A^1$, $A^2$, $A^3$, $A^4$, and $A^5$ is a N.

One iteration of this aspect relates to compounds having the formula:

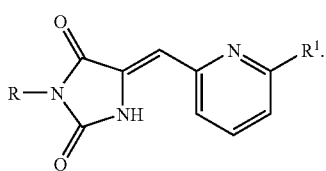

Another iteration of this aspect relates to compounds having the formula:

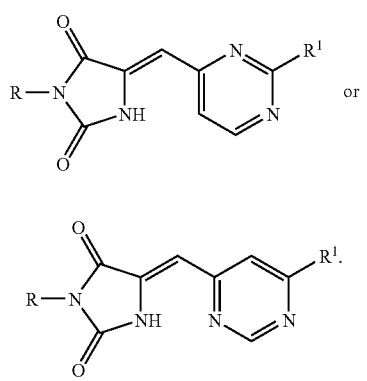

or

A further iteration of this aspect relates to compounds having the formula:

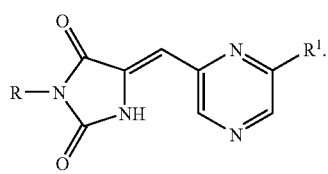

A further aspect of this category relates to Z rings that are phenyl rings having the formula:

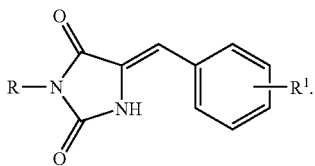

R Units

R units useful with the compounds described herein include substituted or unsubstituted cycloalkyl rings having from 3 to 14 carbon ring atoms. Examples of R units include rings comprising from 3 to 5 carbon atoms: cyclopropyl ($C_3$), cyclobutyl ($C_4$), and cyclopentyl ($C_5$). Compounds described herein comprising these rings have the formulae:

i)

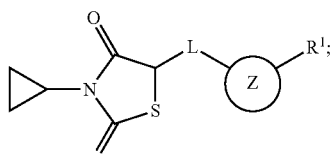

ii)

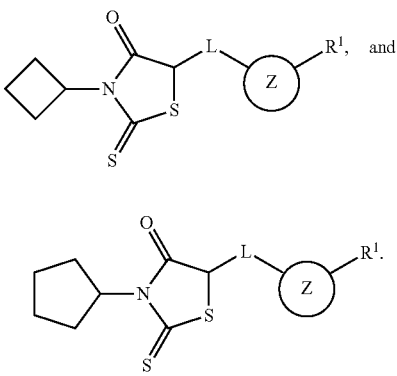

iii)

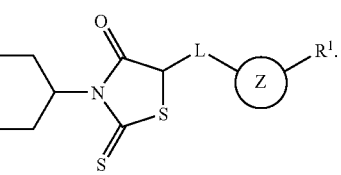

Another example includes compounds wherein R is a cyclohexyl ($C_6$) ring, e.g., wherein the compounds described herein have the formula:

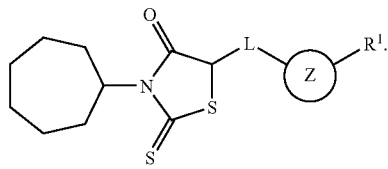

A further example relates to compounds wherein R is a cycloheptyl ($C_7$) ring, e.g., wherein the compounds described herein have the formula:

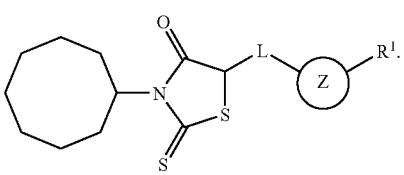

A yet another example relates to compounds wherein R is a cyclooctyl ($C_8$) ring, e.g., wherein the compounds described herein have the formula:

Still further examples of R relates to rings comprising from 9 to 11 carbon atoms, e.g., cyclononyl ($C_9$), cyclodecyl ($C_{10}$), and cycloundecyl ($C_{11}$). Examples of the compounds described herein comprising these rings have the formulae:

i)

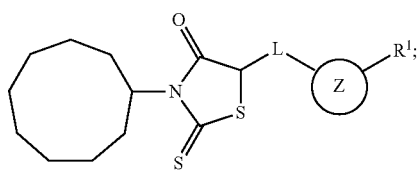

ii)

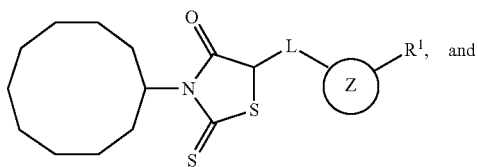

iii)

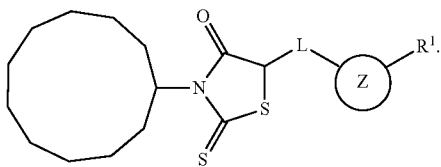

A yet further example relates to compounds wherein R is a cyclododecyl (C$_{12}$) ring, e.g., wherein the compounds described herein having this ring have the formula:

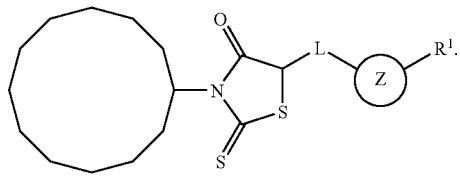

Another aspect of R units relates to fused ring R units. Non-limiting examples of fused R units include octahydropentalenyl, octahydro-1H-indenyl, decahydronaphthalenyl, decahydro-azulenyl, and decahydro-1H-benzo[7]annulenyl. An example of compounds described herein includes octahydropentalenyl (C$_8$) fused ring R units have the formula:

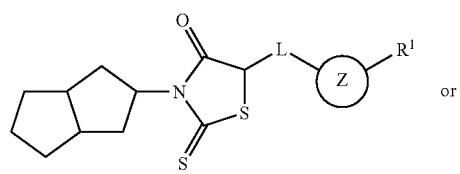

or

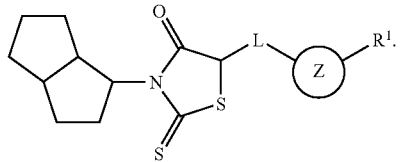

Another example comprises octahydro-1H-indenyl (C$_9$) R units, one example of which has the formula:

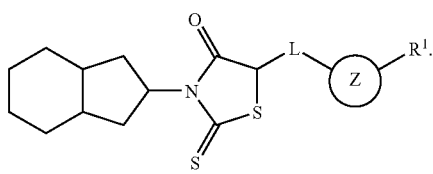

A further example comprises decahydronaphthalenyl (C$_{10}$) R units, one example of which has the formula:

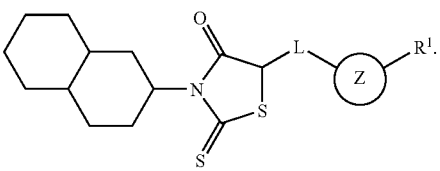

A still further example comprises decahydroazulenyl (C$_{10}$) R units, one example of which has the formula:

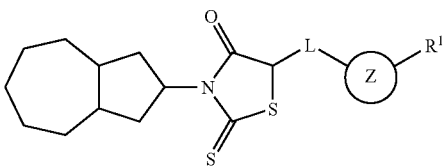

A yet further example comprises decahydro-1H-benzo[7]annulenyl (C$_{11}$) R units, one example of which has the formula:

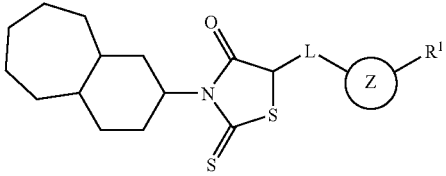

A further aspect of R units relates to bicyclic ring R units. Non-limiting examples of bicyclic R units include bicyclo[1.1.0]butanyl, bicyclo[1.1.1]pentanyl, bicyclo[2.1.1]-hexanyl, bicyclo[2.2.1]heptanyl, bicyclo[3.1.1]heptanyl, bicyclo[2.2.2]octanyl, bicyclo-[3.2.1]octanyl, bicyclo[3.3.2]decanyl, and adamantyl.

The following are a non-limiting examples of this aspect:

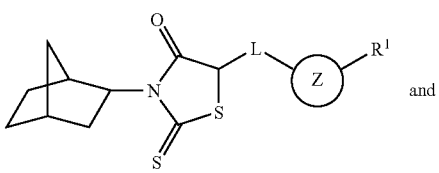 and

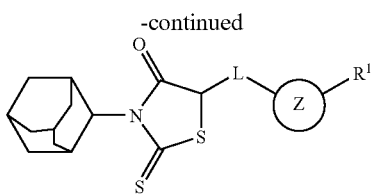

R[1] Units

R[1] units are aryl or heteroaryl rings that can have from 1 to 5 of the ring hydrogen atoms substituted by an organic radical. An example of R[1] relates to phenyl or substituted phenyl having the formula:

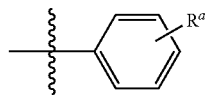

wherein R[a] represents from 1 to 5 (e.g., up to 5) substitutions for a ring hydrogen atom. Compounds described herein comprising a substituted phenyl ring for R[1] have the following formula:

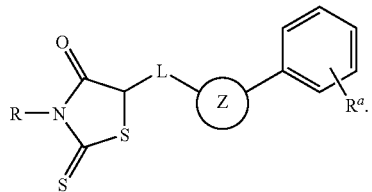

A further example of R[1] relates to heteroaryl units having the formula:

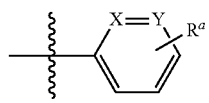

wherein X and Y are each independently chosen from:
i) —CH—; or
ii) —N—; and
R[a] represents from 1 to 5 substitutions (e.g., up to 5) for a ring hydrogen atom.

A first example relates to the compounds described herein having the formula:

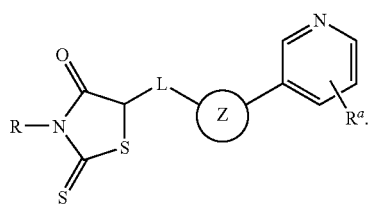

Another example relates to the compounds described herein having the formula

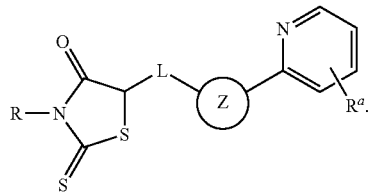

A further example of R[1] relates to heteroaryl units having the formula:

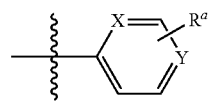

wherein X is chosen from:
i) —CH—; or
ii) —N—;
Y is —N—, and R[a] represents from 1 to 4 (e.g., up to 4) substitutions for a ring hydrogen atom. An example encompasses compounds having the formula:

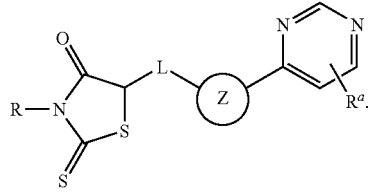

The compounds described herein can be organized into several categories for the strictly non-limiting purpose of describing alternatives for synthetic strategies for the preparation of subgenera of compounds within the scope of the disclosure that are not expressly exemplified herein. This mental organization into categories does not imply anything with respect to increased or decreased biological efficacy with respect to any of the compounds or compositions of matter described herein.

R[1] units can be substituted by from 1 to 5 R[a] units wherein in each R[a] unit is independently chosen from
  i) $C_1$-$C_{12}$ substituted or unsubstituted linear, branched, or cyclic alkyl;
  ii) $C_2$-$C_{12}$ substituted or unsubstituted linear, branched, or cyclic alkenyl;
  iii) $C_2$-$C_{12}$ substituted or unsubstituted linear or branched alkynyl;
  iv) $C_5$-$C_{10}$ substituted or unsubstituted aryl;
  v) $C_1$-$C_9$ substituted or unsubstituted heterocyclic;
  vi) $C_1$-$C_{11}$ substituted or unsubstituted heteroaryl;
  vii) —[C(R[2a])(R[2b])]$_y$OR[3];
    a) wherein R[3] is chosen from:
    b) —H;
    c) $C_1$-$C_{12}$ substituted or unsubstituted linear, branched, or cyclic alkyl;
    d) $C_5$-$C_{10}$ substituted or unsubstituted aryl or alkylenearyl;
    e) $C_1$-$C_9$ substituted or unsubstituted heterocyclic;
    f) $C_1$-$C_{11}$ substituted or unsubstituted heteroaryl;
  viii) —[C(R[2a])(R[2b])]$_y$N(R[4a])(R[4b]);
    a) wherein R[4a] and R[4b] are each independently chosen from:

i) —H;
ii) —OR$^5$;
R$^5$ is hydrogen or C$_1$-C4 linear alkyl;
b) C$_1$-C$_{12}$ substituted or unsubstituted linear, branched, or cyclic alkyl;
c) C$_5$-C$_{10}$ substituted or unsubstituted aryl;
d) C$_1$-C$_9$ substituted or unsubstituted heterocyclic;
e) C$_1$-C$_{11}$ substituted or unsubstituted heteroaryl; or
f) R$^{4a}$ and R$^{4b}$ can be taken together to form a substituted or unsubstituted ring having from 3 to 10 carbon atoms and from 0 to 3 heteroatoms chosen from oxygen, nitrogen, and sulfur;
ix) —[C(R$^{2a}$)(R$^{2b}$)]$_y$C(O)R$^6$;
a) wherein R$^6$ is chosen from:
i) C$_1$-C$_{12}$ substituted or unsubstituted linear, branched, or cyclic alkyl;
ii) —OR$^7$;
R$^7$ is hydrogen, substituted or unsubstituted C$_1$-C$_4$ linear alkyl, C$_5$-C$_{10}$ substituted or unsubstituted aryl, C$_1$-C$_9$ substituted or unsubstituted heterocyclic, C$_1$-C$_{11}$ substituted or unsubstituted heteroaryl;
b) —N(R$^{8a}$)(R$^{8b}$); and
R$^{8a}$ and R$^{8b}$ are each independently hydrogen, C$_1$-C$_{12}$ substituted or unsubstituted linear, branched, or cyclic alkyl; C$_5$-C$_{10}$ substituted or unsubstituted aryl; C$_1$-C$_9$ substituted or unsubstituted heterocyclic; C$_1$-C$_{11}$ substituted or unsubstituted heteroaryl; or R$^{8a}$ and R$^{8b}$ can be taken together to form a substituted or unsubstituted ring having from 3 to 10 carbon atoms and from 0 to 3 heteroatoms chosen from oxygen, nitrogen, and sulfur;
x) —[C(R$^{2a}$)(R$^{2b}$)]$_y$OC(O)R$^9$;
wherein R$^9$ is chosen from:
a) C$_1$-C$_{12}$ substituted or unsubstituted linear, branched, or cyclic alkyl;
b) —N(R$^{10a}$)(R$^{10b}$); and
R$^{10a}$ and R$^{10b}$ are each independently hydrogen, C$_1$-C$_{12}$ substituted or unsubstituted linear, branched, or cyclic alkyl; C$_5$-C$_{10}$ substituted or unsubstituted aryl; C$_1$-C$_9$ substituted or unsubstituted heterocyclic; C$_1$-C$_{11}$ substituted or unsubstituted heteroaryl; or R$^{15a}$ and R$^{10b}$ can be taken together to form a substituted or unsubstituted ring having from 3 to 10 carbon atoms and from 0 to 3 heteroatoms chosen from oxygen, nitrogen, and sulfur;
xi) —[C(R$^{2a}$)(R$^{2b}$)]$_y$NR$^{11}$C(O)R$^{12}$;
wherein R$^{11}$ is chosen from:
a) —H; and
b) C$_1$-C$_4$ substituted or unsubstituted linear, branched, or cyclic alkyl;
c) wherein R$^{12}$ is chosen from:
i) C$_1$-C$_{12}$ substituted or unsubstituted linear, branched, or cyclic alkyl; and
ii) —N(R$^{13a}$)(R$^{13b}$);
R$^{13a}$ and R$^{13b}$ are each independently hydrogen, C$_1$-C$_{12}$ substituted or unsubstituted linear, branched, or cyclic alkyl; C$_5$-C$_{10}$ substituted or unsubstituted aryl; C$_1$-C$_9$ substituted or unsubstituted heterocyclic; C$_1$-C$_{11}$ substituted or unsubstituted heteroaryl; or R$^{13a}$ and R$^{13b}$ can be taken together to form a substituted or unsubstituted ring having from 3 to 10 carbon atoms and from 0 to 3 heteroatoms chosen from oxygen, nitrogen, and sulfur;
xii) —[C(R$^{2a}$)(R$^{2b}$)]$_y$CN;
xiii) —[C(R$^{2a}$)(R$^{2b}$)]$_y$NO$_2$;
xiv) —[C(R$^{2a}$)(R$^{2b}$)]$_y$SO$_2$R$^{14}$;

wherein R$^{14}$ is hydrogen, hydroxyl, substituted or unsubstituted C$_1$-C$_4$ linear or branched alkyl; substituted or unsubstituted C$_5$-C$_{10}$, or C$_{1-4}$ aryl; C$_7$-C$_{15}$ alkylenearyl; C$_1$-C$_9$ substituted or unsubstituted heterocyclic; or C$_1$-C$_{11}$ substituted or unsubstituted heteroaryl;
xv) halogen;
R$^{2a}$ and R$^{2b}$ are each independently hydrogen or C$_1$-C$_4$ alkyl; and
the index y is from 0 to 5.

One aspect of R$^a$ units relates to a R$^1$ unit that is a phenyl ring and wherein the phenyl ring is substituted by one or more units chosen from:
i) C$_1$-C$_4$ linear, branched, or cyclic alkyl, alkenyl, and alkynyl;
ii) C$_1$-C$_4$ linear or branched haloalkyl;
iii) C$_1$-C$_4$ linear or branched alkoxy;
iv) —F, —Cl, —Br, or —I;
v) —CN; or
vi) —NO$_2$.

Non-limiting examples of this aspect include R$^1$ units that are 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2,3,4-trifluorophenyl, 2,3,5-trifluorophenyl, 2,3,6-trifluorophenyl, 2,4,6-trifluorophenyl, 2,3,4,5-tetrafluorophenyl, 2,3,4,6-tetrafluorophenyl, 2,3,4,5,6-pentafluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3,4-trichlorophenyl, 2,3,5-trichlorophenyl, 2,3,6-trichlorophenyl, 2,4,6-trichlorophenyl, 2,3,4,5-tetrachlorophenyl, 2,3,4,6-tetrachlorophenyl, 2,3,4,5,6-pentachlorophenyl, 2-nitrophenyl, 3-nitrophenyl, 4-nitrophenyl, 2,3-dinitrophenyl, 2,4-dinitrophenyl, 2,5-dinitrophenyl, 2,6-dinitrophenyl, 3,4-dinitrophenyl, 3,5-dinitrophenyl, 2,3,4-trinitrophenyl, 2,3,5-trinitrophenyl, 2,3,6-trinitrophenyl, 2,4,6-trinitrophenyl, 2,3,4,5-tetranitrophenyl, 2,3,4,6-tetranitrophenyl, 2,3,4,5,6-pentanitrophenyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2,3,4,5-tetramethylphenyl, 2,3,4,6-tetramethylphenyl, 2,3,4,5,6-pentamethylphenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3,4-trimethoxyphenyl, 2,3,5-trimethoxyphenyl, 2,3,6-trimethoxyphenyl, 2,4,6-trimethoxyphenyl, 2,3,4,5-tetramethoxyphenyl, 2,3,4,6-tetramethoxyphenyl, and 2,3,4,5,6-pentamethoxyphenyl.

Another aspect of R$^a$ units relates to a R$^1$ unit that is a pyridin-3-yl ring and wherein the pyridine-3-yl ring is substituted by one or more units chosen from:
i) C$_1$-C$_4$ linear, branched, or cyclic alkyl, alkenyl, and alkynyl;
ii) C$_1$-C$_4$ linear or branched haloalkyl;
iii) C$_1$-C$_4$ linear or branched alkoxy;
iv) —F, —Cl, —Br, or —I;
v) —CN; or
vi) —NO$_2$.

Non-limiting examples of this aspect include R$^1$ units that are 2-fluoropyridin-3-yl, 4-fluoropyridin-3-yl, 2,4-difluoropyridin-3-yl, 2,5-difluoropyridin-3-yl, 2,6-difluoropyridin-3-yl, 2,4,6-trifluoropyridin-3-yl, 2-chloropyridin-3-yl, 4-chloropyridin-3-yl, 2,4-dichloropyridin-3-yl, 2,5-dichloropyridin-3-yl, 2,6-dichloropyridin-3-yl, 2,4,6-trichloropyridin-3-yl, 2-nitropyridin-3-yl, 4-nitropyridin-3-yl, 2,4-dinitropyridin-3-yl, 2,5-dinitropyridin-3-yl, 2,6-dinitropyridin-3-yl, 2,4,6-trinitropyridin-3-yl, 2-methylpyridin-3-yl, 4-methylpyridin-3-yl, 2,4-dimethylpyridin-3-yl, 2,5-dimethylpyridin-3-yl, 2,6-dimethylpyridin-3-yl, 2,4,6-trimethylpyridin-3-yl, 2-methoxypyridin-3-yl, 4-methoxypyridin-3-yl, 2,4-dimethoxypyridin-3-yl, 2,5-dimethoxypyridin-3-yl, and 2,6-dimethoxypyridin-3-yl.

Stated another way, $R^1$ units can be substituted by from 1 to 5 organic radicals independently selected from halogen; substituted or unsubstituted haloalkyl; substituted or unsubstituted $C_1$-$C_{12}$ alkyl; substituted or unsubstituted $C_2$-$C_{12}$ alkenyl; substituted or unsubstituted $C_2$-$C_{12}$ alkynyl; substituted or unsubstituted $C_5$-$C_{10}$ aryl; substituted or unsubstituted $C_1$-$C_{12}$ heteroalkyl, substituted or unsubstituted $C_1$-$C_{12}$ heteroalkenyl, substituted or unsubstituted $C_2$-$C_{12}$ heteroalkynyl; $C_1$-$C_9$ substituted or unsubstituted heterocyclic; $C_1$-$C_{11}$ substituted or unsubstituted heteroaryl; substituted or unsubstituted $C_1$-$C_5$ alkoxyalkyl; substituted or unsubstituted $C_2$-$C_5$ alkoxyalkenyl; substituted or unsubstituted $C_2$-$C_5$ alkoxyalkynyl; substituted or unsubstituted $C_1$-$C_5$ aminoalkyl; substituted or unsubstituted $C_2$-$C_5$ aminoalkenyl; substituted or unsubstituted $C_2$-$C_5$ aminoalkynyl; substituted or unsubstituted $C_1$-$C_5$ carboxyalkyl; substituted or unsubstituted $C_2$-$C_5$ carboxyalkenyl; substituted or unsubstituted $C_2$-$C_5$ carboxyalkynyl; substituted or unsubstituted $C_1$-$C_5$ amidoalkyl; substituted or unsubstituted $C_2$-$C_5$ amidoalkenyl; substituted or unsubstituted $C_2$-$C_5$ amidoalkynyl; substituted or unsubstituted $C_1$-$C_5$ cyanoalkyl; substituted or unsubstituted $C_2$-$C_5$ cyanoalkenyl; substituted or unsubstituted $C_2$-$C_5$ cyanoalkynyl; substituted or unsubstituted $C_1$-$C_5$ nitroalkyl; substituted or unsubstituted $C_2$-$C_5$ nitroalkenyl; substituted or unsubstituted $C_2$-$C_5$ nitroalkynyl; substituted or unsubstituted $C_1$-$C_5$ sulfonylalkyl; substituted or unsubstituted $C_2$-$C_5$ sulfonylalkenyl; substituted or unsubstituted $C_2$-$C_5$ sulfonylalkynyl; or substituted or unsubstituted amino.

As indicated above, L is a direct bond or a substituted or unsubstituted linking unit. As used herein, the term direct bond indicates a covalent bond between the carbon on the five-member ring structure to which L is shown to be attached and a ring atom of Z, i.e., a ring atom of a substituted or unsubstituted 5-member heteroaryl ring; a substituted or unsubstituted 6-member heteroaryl ring; or a phenyl ring. When L is a substituted or unsubstituted linking unit, it is a linking unit having 1 to 4 carbon atoms and up to 2 heteroatoms (e.g., oxygen, nitrogen, or sulfur). Examples of L as a substituted or unsubstituted linking unit include substituted or unsubstituted alkyl groups (e.g., methyl; ethyl; propyl; butyl; —C(O)—; —CH$_2$(O)—; or —C(O)CH$_2$—), substituted or unsubstituted alkenyl groups (e.g., =CH—; =CHCH$_2$—; =CHCH$_2$CH$_2$—; or =CHCH$_2$CH$_2$CH$_2$—), substituted or unsubstituted alkynyl groups, substituted or unsubstituted heteroalkyl groups with up to 2 heteroatoms (e.g., —NH—; —CH$_2$NH—; —NHCH$_2$—; —NHC(O)—; —C(O)NH—; —CH$_2$NHC(O)—; —CH$_2$C(O)NH—; —NHC(O)CH$_2$—; or —C(O)NHCH$_2$—), substituted or unsubstituted heteroalkenyl groups with up to 2 heteroatoms (e.g., =N— or —N=), and substituted or unsubstituted heteroalkynyl groups with up to 2 heteroatoms.

The term organic unit, or organic radical, as described herein refers to groups or moieties that comprise one or more carbon atoms and which form a portion of one of the compounds or pharmaceutically acceptable salts thereof. For example, many of the substituent units referred to elsewhere herein are organic units. In order to effectively function in the context of their presence in the compounds and/or salts described herein, the organic units should often have variable ranges of restricted size and/or molecular weight, so as to provide desired binding to the target enzymes, solubility, bioabsorption characteristics. An organic unit can have, for example, 1-26 carbon atoms, 1-18 carbon atoms, 1-12 carbon atoms, 1-8 carbon atoms, or 1-4 carbon atoms. Organic units often have hydrogen bound to at least some of the carbon atoms of the organic units, and can optionally contain the common heteroatoms found in substituted organic compounds, such as oxygen, nitrogen, sulfur, and the like, or inorganic atoms such as halogens, phosphorus, and the like. One example of an organic radical that comprises no inorganic atoms is a 5,6,7,8-tetrahydro-2-naphthyl radical. Some organic radicals can contain 1-10 inorganic heteroatoms bound thereto or therein, including halogens, oxygen, sulfur, nitrogen, phosphorus, and the like. Examples of an organic radical include, but are not limited to alkyl, substituted alkyl, cycloalkyl, substituted cycloalkyl, mono-substituted amino, di-substituted amino, acyloxy, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals, and the like.

As used herein, the term substituted includes the addition of an organic unit or inorganic unit (as described herein) to a position attached to the main chain of the organic unit or inorganic unit, e.g., the replacement of a hydrogen by one of these molecules. Examples of substitution groups include, but are not limited to, hydroxyl, halogen (e.g., F, Br, Cl, or I), and carboxyl groups. Conversely, as used herein, the term unsubstituted indicates the hydrocarbon, hetero-hydrocarbon, aryl, or heteroaryl group has a full compliment of hydrogens, i.e., commensurate with its saturation level, with no substitutions, e.g., linear decane (—(CH$_2$)$_9$—CH$_3$).

Substituted and unsubstituted linear, branched, or cyclic alkyl units include the following non-limiting examples: methyl ($C_1$), ethyl ($C_2$), n-propyl ($C_3$), iso-propyl ($C_3$), cyclopropyl ($C_3$), n-butyl ($C_4$), sec-butyl ($C_4$), iso-butyl ($C_4$), tert-butyl ($C_4$), cyclobutyl ($C_4$), cyclopentyl ($C_5$), cyclohexyl ($C_6$), and the like; whereas substituted linear, branched, or cyclic alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 2,2,2-trifluoroethyl ($C_3$), 3-carboxypropyl ($C_3$), 2,3-dihydroxycyclobutyl ($C_4$), and the like.

Substituted and unsubstituted linear, branched, or cyclic alkenyl include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.

Substituted and unsubstituted linear or branched alkynyl include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

Substituted and unsubstituted alkoxy as used herein denotes a unit having the general formula —OR$^{100}$ wherein $R^{100}$ is an alkyl, alkylenyl, or alkynyl unit as defined herein above, for example, methoxy, methoxymethyl, methoxymethyl.

Substituted and unsubstituted haloalkyl are used herein denotes an alkyl unit having a hydrogen atom substituted by one or more halogen atoms, for example, trifluoromethyl, 1,2-dichloroethyl, and 3,3,3-trifluoropropyl.

The term aryl as used herein denotes cyclic organic units that comprise at least one benzene ring having a conjugated and aromatic six-membered ring, non-limiting examples of which include phenyl ($C_6$), naphthylen-1-yl ($C_{10}$), naphthylen-2-yl ($C_{10}$). Aryl rings can have one or more hydrogen atoms substituted by another organic or inorganic radical. Non-limiting examples of substituted aryl rings include: 4-fluorophenyl ($C_6$), 2-hydroxyphenyl ($C_6$), 3-methylphenyl ($C_6$), 2-amino-4-fluorophenyl ($C_6$), 2-(N,N-diethylamino) phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyanonaphthylen-1-yl ($C_{10}$).

The term heteroaryl denotes an organic unit comprising a five or six member conjugated and aromatic ring wherein at least one of the ring atoms is a heteroatom selected from nitrogen, oxygen, or sulfur. The heteroaryl rings can comprise a single ring, for example, a ring having 5 or 6 atoms wherein at least one ring atom is a heteroatom not limited to nitrogen, oxygen, or sulfur, such as a pyridine ring, a furan ring, or thiofuran ring. A heteroaryl can also be a fused multicyclic and heteroaromatic ring system having wherein at least one of the rings is an aromatic ring and at least one atom of the aromatic ring is a heteroatom including nitrogen, oxygen, or sulfur.

The following are non-limiting examples of heteroaryl rings according to the present disclosure:

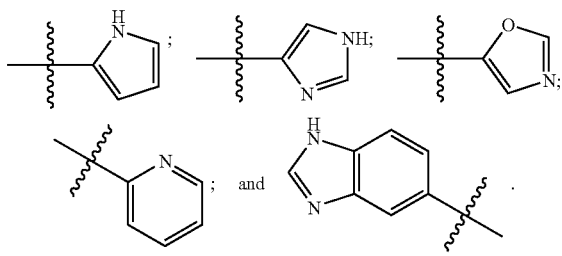

The term heterocyclic denotes a ring system having from 3 to 10 atoms wherein at least one of the ring atoms is a heteroatom not limited to nitrogen, oxygen, or sulfur. The rings can be single rings, fused rings, or bicyclic rings. Non-limiting examples of heterocyclic rings include:

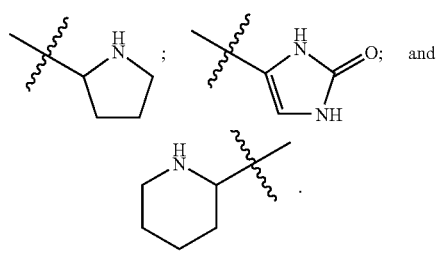

All of the aforementioned heteroaryl or heterocyclic rings can be optionally substituted with one or more substitutes for hydrogen as described herein further.

Throughout the description of the present disclosure the terms having the spelling thiophene-2-yl and thiophene-3-yl are used to describe the heteroaryl units having the respective formulae:

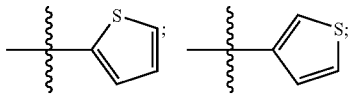

whereas in naming the compounds of the present disclosure, the chemical nomenclature for these moieties are typically spelled thiophen-2-yl and thiophen-3-yl respectively. Herein the terms thiophene-2-yl and thiophene-3-yl are used when describing these rings as units or moieties which make up the compounds of the present disclosure solely to make it unambiguous to the artisan of ordinary skill which rings are referred to herein.

For the purposes of the present disclosure the terms compound, analog, and composition of matter stand equally well for the chemical entities described herein, including all enantiomeric forms, diastereomeric forms, salts, and the like, and the terms compound, analog, and composition of matter are used interchangeably throughout the present specification.

Ranges can be expressed herein as from about one particular value, and/or to about another particular value. When such a range is expressed, another aspect includes from the one particular value and/or to the other particular value. Similarly, when values are expressed as approximations, by use of the antecedent about, it will be understood that the particular value forms another aspect. It will be further understood that the endpoints of each of the ranges are significant both in relation to the other endpoint, and independently of the other endpoint. It is also understood that there are a number of values described herein, and that each value is also herein described as about that particular value in addition to the value itself. For example, if the value 10 is described, then about 10 is also described. It is also understood that when a value is described, then less than or equal to the value, greater than or equal to the value, and possible ranges between values are also described, as appropriately understood by the skilled artisan. For example, if the value 10 is described, then less than or equal to 10 as well as greater than or equal to 10 is also described. It is also understood that throughout the application data are provided in a number of different formats and that this data represent endpoints and starting points and ranges for any combination of the data points. For example, if a particular data point 10 and a particular data point 15 are described, it is understood that greater than, greater than or equal to, less than, less than or equal to, and equal to 10 and 15 are considered described as well as between 10 and 15. It is also understood that each unit between two particular units are also described. For example, if 10 and 15 are described, then 11, 12, 13, and 14 are also described.

Optional or optionally means that the subsequently described event or circumstance can or cannot occur, and that the description includes instances where the event or circumstance occurs and instances where it does not.

As used herein, the phrase up to a certain number includes the recited number in addition to all integers preceeding in numerical order. For example, "up to 5" includes 0, 1, 2, 3, 4, and 5.

The term pharmaceutically acceptable is a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

The compounds described herein can also be in the form of a pharmaceutically acceptable salt comprising one or more anions or cations. The following are non-limiting examples of anions chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, and citrate. The following are non-limiting examples of cations sodium, lithium, potassium, calcium, magnesium, and bismuth.

The compounds described herein can also be in the form of prodrugs. As used herein, the term prodrug refers to a precursor or derivative form of a compound that a medical or other practitioner may wish to deliver to a subject in an inactive form that can be activated subsequent to administration. Such a prodrug may include a property, such as, for example, lower toxicity, increased solubility, or improved transfer rate, as compared to the parent compound.

One category of the compounds described herein relates to 3-N-cycloalkyl-5-substituted-2-thioxothiazolidin-4-ones having the formula:

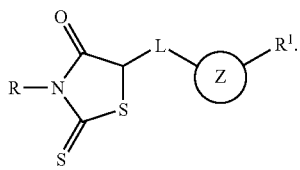

An example of compounds within this category includes compounds wherein Z is a 5-member heteroaryl ring, the compounds having the formula:

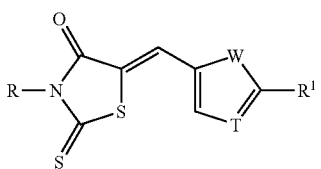

wherein W is O, S, or NH; T is CH or N.

The compounds described herein within this category wherein T is CH can be prepared according to the synthesis outlined herein below in Scheme I and described in Example 1.

Scheme I

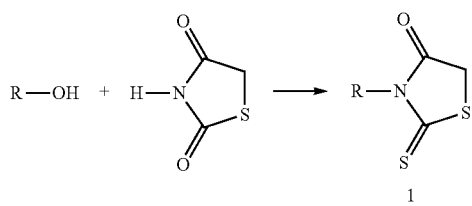

Reagents and conditions: (a) PPh$_3$, DIAD, THF; -78° C. to rt.

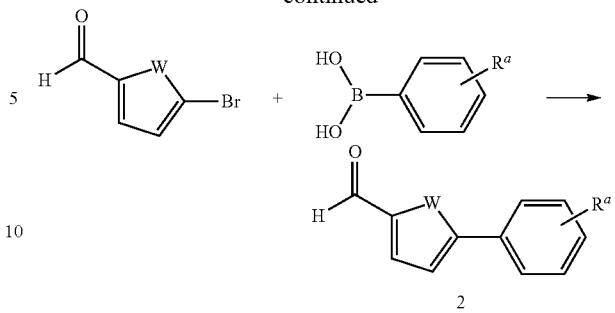

Reagents and conditions: (b) Pd(PPh$_3$)$_4$, toluene, EtOH, Na$_2$CO$_3$; reflux.

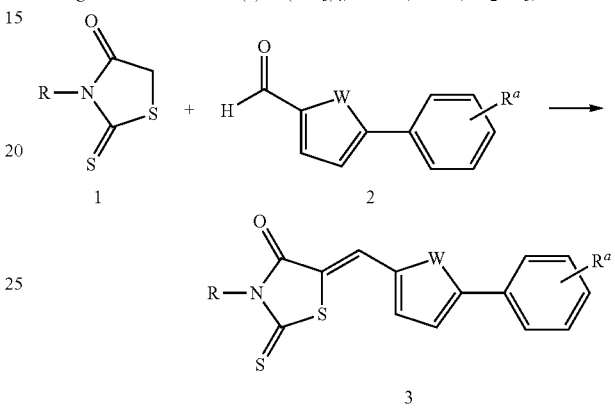

Reagents and conditions: (c) NaOAc, HOAc, HOAc; reflux.

Examples of compounds as described herein wherein T is CH are listed below in Table I.

TABLE I

| No. | R | W | R$^1$ |
|---|---|---|---|
| 1 | cyclohexyl | O | phenyl |
| 2 | cyclohexyl | O | 3-methylphenyl |
| 3 | cyclohexyl | O | 4-methylphenyl |
| 4 | cyclohexyl | O | 3,4-dimethylphenyl |
| 5 | cyclohexyl | O | 3-methoxyphenyl |
| 6 | cyclohexyl | O | 4-methoxyphenyl |
| 7 | cyclohexyl | O | 3,4-dimethoxyphenyl |
| 8 | cyclohexyl | O | 3-fluorophenyl |
| 9 | cyclohexyl | O | 4-fluorophenyl |
| 10 | cyclohexyl | O | 3,4-difluorophenyl |
| 11 | cyclohexyl | O | 3-chlorophenyl |
| 12 | cyclohexyl | O | 4-chlorophenyl |
| 13 | cyclohexyl | O | 3,4-dichlorophenyl |
| 14 | cyclohexyl | O | 3-nitrophenyl |
| 15 | cyclohexyl | O | 4-nitrophenyl |
| 16 | cyclohexyl | O | 3,4-dinitrophenyl |
| 17 | cyclohexyl | S | phenyl |
| 18 | cyclohexyl | S | 3-methylphenyl |
| 19 | cyclohexyl | S | 4-methylphenyl |
| 20 | cyclohexyl | S | 3,4-dimethylphenyl |
| 21 | cyclohexyl | S | 3-methoxyphenyl |
| 22 | cyclohexyl | S | 4-methoxyphenyl |
| 23 | cyclohexyl | S | 3,4-dimethoxyphenyl |
| 24 | cyclohexyl | S | 3-fluorophenyl |
| 25 | cyclohexyl | S | 4-fluorophenyl |
| 26 | cyclohexyl | S | 3,4-difluorophenyl |
| 27 | cyclohexyl | S | 3-chlorophenyl |
| 28 | cyclohexyl | S | 4-chlorophenyl |
| 29 | cyclohexyl | S | 3,4-dichlorophenyl |
| 30 | cyclohexyl | S | 3-nitrophenyl |
| 31 | cyclohexyl | S | 4-nitrophenyl |
| 32 | cyclohexyl | S | 3,4-dinitrophenyl |
| 33 | cycloheptyl | O | phenyl |
| 34 | cycloheptyl | O | 3-methylphenyl |

TABLE I-continued

| No. | R | W | R¹ |
|---|---|---|---|
| 35 | cycloheptyl | O | 4-methylphenyl |
| 36 | cycloheptyl | O | 3,4-dimethylphenyl |
| 37 | cycloheptyl | O | 3-methoxyphenyl |
| 38 | cycloheptyl | O | 4-methoxyphenyl |
| 39 | cycloheptyl | O | 3,4-dimethoxyphenyl |
| 40 | cycloheptyl | O | 3-fluorophenyl |
| 41 | cycloheptyl | O | 4-fluorophenyl |
| 42 | cycloheptyl | O | 3,4-difluorophenyl |
| 43 | cycloheptyl | O | 3-chlorophenyl |
| 44 | cycloheptyl | O | 4-chlorophenyl |
| 45 | cycloheptyl | O | 3,4-dichlorophenyl |
| 46 | cycloheptyl | O | 3-nitrophenyl |
| 47 | cycloheptyl | O | 4-nitrophenyl |
| 48 | cycloheptyl | O | 3,4-dinitrophenyl |
| 49 | cycloheptyl | S | phenyl |
| 50 | cycloheptyl | S | 3-methylphenyl |
| 51 | cycloheptyl | S | 4-methylphenyl |
| 52 | cycloheptyl | S | 3,4-dimethylphenyl |
| 53 | cycloheptyl | S | 3-methoxyphenyl |
| 54 | cycloheptyl | S | 4-methoxyphenyl |
| 55 | cycloheptyl | S | 3,4-dimethoxyphenyl |
| 56 | cycloheptyl | S | 3-fluorophenyl |
| 57 | cycloheptyl | S | 4-fluorophenyl |
| 58 | cycloheptyl | S | 3,4-difluorophenyl |
| 59 | cycloheptyl | S | 3-chlorophenyl |
| 60 | cycloheptyl | S | 4-chlorophenyl |
| 61 | cycloheptyl | S | 3,4-dichlorophenyl |
| 62 | cycloheptyl | S | 3-nitrophenyl |
| 63 | cycloheptyl | S | 4-nitrophenyl |
| 64 | cycloheptyl | S | 3,4-dinitrophenyl |
| 65 | cyclooctyl | O | phenyl |
| 66 | cyclooctyl | O | 3-methylphenyl |
| 67 | cyclooctyl | O | 4-methylphenyl |
| 68 | cyclooctyl | O | 3,4-dimethylphenyl |
| 69 | cyclooctyl | O | 3-methoxyphenyl |
| 70 | cyclooctyl | O | 4-methoxyphenyl |
| 71 | cyclooctyl | O | 3,4-dimethoxyphenyl |
| 72 | cyclooctyl | O | 3-fluorophenyl |
| 73 | cyclooctyl | O | 4-fluorophenyl |
| 74 | cyclooctyl | O | 3,4-difluorophenyl |
| 75 | cyclooctyl | O | 3-chlorophenyl |
| 76 | cyclooctyl | O | 4-chlorophenyl |
| 77 | cyclooctyl | O | 3,4-dichlorophenyl |
| 78 | cyclooctyl | O | 3-nitrophenyl |
| 79 | cyclooctyl | O | 4-nitrophenyl |
| 80 | cyclooctyl | O | 3,4-dinitrophenyl |
| 81 | cyclooctyl | S | phenyl |
| 82 | cyclooctyl | S | 3-methylphenyl |
| 83 | cyclooctyl | S | 4-methylphenyl |
| 84 | cyclooctyl | S | 3,4-dimethylphenyl |
| 85 | cyclooctyl | S | 3-methoxyphenyl |
| 86 | cyclooctyl | S | 4-methoxyphenyl |
| 87 | cyclooctyl | S | 3,4-dimethoxyphenyl |
| 88 | cyclooctyl | S | 3-fluorophenyl |
| 89 | cyclooctyl | S | 4-fluorophenyl |
| 90 | cyclooctyl | S | 3,4-difluorophenyl |
| 91 | cyclooctyl | S | 3-chlorophenyl |
| 92 | cyclooctyl | S | 4-chlorophenyl |
| 93 | cyclooctyl | S | 3,4-dichlorophenyl |
| 94 | cyclooctyl | S | 3-nitrophenyl |
| 95 | cyclooctyl | S | 4-nitrophenyl |
| 96 | cyclooctyl | S | 3,4-dinitrophenyl |
| 97 | cyclododecyl | O | phenyl |
| 98 | cyclododecyl | O | 3-methylphenyl |
| 99 | cyclododecyl | O | 4-methylphenyl |
| 100 | cyclododecyl | O | 3,4-dimethylphenyl |
| 101 | cyclododecyl | O | 3-methoxyphenyl |
| 102 | cyclododecyl | O | 4-methoxyphenyl |
| 103 | cyclododecyl | O | 3,4-dimethoxyphenyl |
| 104 | cyclododecyl | O | 3-fluorophenyl |
| 105 | cyclododecyl | O | 4-fluorophenyl |
| 106 | cyclododecyl | O | 3,4-difluorophenyl |
| 107 | cyclododecyl | O | 3-chlorophenyl |
| 108 | cyclododecyl | O | 4-chlorophenyl |
| 109 | cyclododecyl | O | 3,4-dichlorophenyl |
| 110 | cyclododecyl | O | 3-nitrophenyl |
| 111 | cyclododecyl | O | 4-nitrophenyl |
| 112 | cyclododecyl | O | 3,4-dinitrophenyl |
| 113 | cyclododecyl | S | phenyl |
| 114 | cyclododecyl | S | 3-methylphenyl |
| 115 | cyclododecyl | S | 4-methylphenyl |
| 116 | cyclododecyl | S | 3,4-dimethylphenyl |
| 117 | cyclododecyl | S | 3-methoxyphenyl |
| 118 | cyclododecyl | S | 4-methoxyphenyl |
| 119 | cyclododecyl | S | 3,4-dimethoxyphenyl |
| 120 | cyclododecyl | S | 3-fluorophenyl |
| 121 | cyclododecyl | S | 4-fluorophenyl |
| 122 | cyclododecyl | S | 3,4-difluorophenyl |
| 123 | cyclododecyl | S | 3-chlorophenyl |
| 124 | cyclododecyl | S | 4-chlorophenyl |
| 125 | cyclododecyl | S | 3,4-dichlorophenyl |
| 126 | cyclododecyl | S | 3-nitrophenyl |
| 127 | cyclododecyl | S | 4-nitrophenyl |
| 128 | cyclododecyl | S | 3,4-dinitrophenyl |

Further examples of these compounds wherein T is CH and R is a bicyclic alkyl unit are listed in Table II. The compounds listed in Table II and additional compounds wherein T is CH and R is a bicyclic alkyl unit can be prepared by the procedure outlined in Scheme I and described in Example 1 by substituting the bicyclic alcohol for the cycloalkyl alcohol.

TABLE II

| No. | R | W | R¹ |
|---|---|---|---|
| 129 | bicyclo[2.2.1]heptan-2-yl | O | phenyl |
| 130 | bicyclo[2.2.1]heptan-2-yl | O | 3-methylphenyl |
| 131 | bicyclo[2.2.1]heptan-2-yl | O | 4-methylphenyl |
| 132 | bicyclo[2.2.1]heptan-2-yl | O | 3,4-dimethylphenyl |
| 133 | bicyclo[2.2.1]heptan-2-yl | O | 3-methoxyphenyl |
| 134 | bicyclo[2.2.1]heptan-2-yl | O | 4-methoxyphenyl |
| 135 | bicyclo[2.2.1]heptan-2-yl | O | 3,4-dimethoxyphenyl |
| 136 | bicyclo[2.2.1]heptan-2-yl | O | 3-fluorophenyl |
| 137 | bicyclo[2.2.1]heptan-2-yl | O | 4-fluorophenyl |
| 138 | bicyclo[2.2.1]heptan-2-yl | O | 3,4-difluorophenyl |
| 139 | bicyclo[2.2.1]heptan-2-yl | O | 3-chlorophenyl |
| 140 | bicyclo[2.2.1]heptan-2-yl | O | 4-chlorophenyl |
| 141 | bicyclo[2.2.1]heptan-2-yl | O | 3,4-dichlorophenyl |
| 142 | bicyclo[2.2.1]heptan-2-yl | O | 3-nitrophenyl |
| 143 | bicyclo[2.2.1]heptan-2-yl | O | 4-nitrophenyl |
| 144 | bicyclo[2.2.1]heptan-2-yl | O | 3,4-dinitrophenyl |
| 145 | bicyclo[2.2.1]heptan-2-yl | S | phenyl |
| 146 | bicyclo[2.2.1]heptan-2-yl | S | 3-methylphenyl |
| 147 | bicyclo[2.2.1]heptan-2-yl | S | 4-methylphenyl |
| 148 | bicyclo[2.2.1]heptan-2-yl | S | 3,4-dimethylphenyl |
| 149 | bicyclo[2.2.1]heptan-2-yl | S | 3-methoxyphenyl |
| 150 | bicyclo[2.2.1]heptan-2-yl | S | 4-methoxyphenyl |
| 151 | bicyclo[2.2.1]heptan-2-yl | S | 3,4-dimethoxyphenyl |
| 152 | bicyclo[2.2.1]heptan-2-yl | S | 3-fluorophenyl |
| 153 | bicyclo[2.2.1]heptan-2-yl | S | 4-fluorophenyl |
| 154 | bicyclo[2.2.1]heptan-2-yl | S | 3,4-difluorophenyl |
| 155 | bicyclo[2.2.1]heptan-2-yl | S | 3-chlorophenyl |
| 156 | bicyclo[2.2.1]heptan-2-yl | S | 4-chlorophenyl |
| 157 | bicyclo[2.2.1]heptan-2-yl | S | 3,4-dichlorophenyl |
| 158 | bicyclo[2.2.1]heptan-2-yl | S | 3-nitrophenyl |
| 159 | bicyclo[2.2.1]heptan-2-yl | S | 4-nitrophenyl |
| 160 | bicyclo[2.2.1]heptan-2-yl | S | 3,4-dinitrophenyl |
| 161 | adamantyl | O | phenyl |
| 162 | adamantyl | O | 3-methylphenyl |
| 163 | adamantyl | O | 4-methylphenyl |
| 164 | adamantyl | O | 3,4-dimethylphenyl |
| 165 | adamantyl | O | 3-methoxyphenyl |
| 166 | adamantyl | O | 4-methoxyphenyl |
| 167 | adamantyl | O | 3,4-dimethoxyphenyl |
| 168 | adamantyl | O | 3-fluorophenyl |
| 169 | adamantyl | O | 4-fluorophenyl |
| 170 | adamantyl | O | 3,4-difluorophenyl |
| 171 | adamantyl | O | 3-chlorophenyl |
| 172 | adamantyl | O | 4-chlorophenyl |
| 173 | adamantyl | O | 3,4-dichlorophenyl |
| 174 | adamantyl | O | 3-nitrophenyl |
| 175 | adamantyl | O | 4-nitrophenyl |

TABLE II-continued

| No. | R | W | R¹ |
|---|---|---|---|
| 176 | adamantyl | O | 3,4-dinitrophenyl |
| 177 | adamantyl | S | phenyl |
| 178 | adamantyl | S | 3-methylphenyl |
| 179 | adamantyl | S | 4-methylphenyl |
| 180 | adamantyl | S | 3,4-dimethylphenyl |
| 181 | adamantyl | S | 3-methoxyphenyl |
| 182 | adamantyl | S | 4-methoxyphenyl |
| 183 | adamantyl | S | 3,4-dimethoxyphenyl |
| 184 | adamantyl | S | 3-fluorophenyl |
| 185 | adamantyl | S | 4-fluorophenyl |
| 186 | adamantyl | S | 3,4-difluorophenyl |
| 187 | adamantyl | S | 3-chlorophenyl |
| 188 | adamantyl | S | 4-chlorophenyl |
| 189 | adamantyl | S | 3,4-dichlorophenyl |
| 190 | adamantyl | S | 3-nitrophenyl |
| 191 | adamantyl | S | 4-nitrophenyl |
| 192 | adamantyl | S | 3,4-dinitrophenyl |

Further examples of compounds as described herein include those wherein Z is an aryl ring as shown by the following formula:

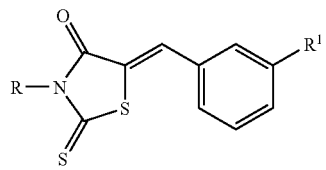

The compounds described herein wherein Z is an aryl ring can be prepared according to the synthesis outlined herein below in Scheme II and described in Example 2.

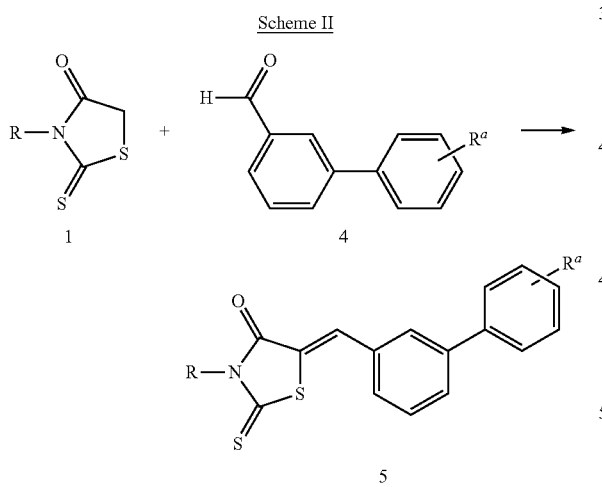

Scheme II

Reagents and conditions: (a) NaOAc, HOAc; reflux.
Reagents and conditions: (c) NaOAc, HOAc; reflux.

Examples of such compounds as described herein wherein Z is an aryl ring are listed below in Table III.

TABLE III

| No. | R | R¹ |
|---|---|---|
| 193 | cyclopentyl | phenyl |
| 194 | cyclopentyl | 2-fluorophenyl |
| 195 | cyclopentyl | 3-fluorophenyl |
| 196 | cyclopentyl | 4-fluorophenyl |
| 197 | cyclopentyl | 2-methylphenyl |
| 198 | cyclopentyl | 3-methylphenyl |
| 199 | cyclopentyl | 4-methylphenyl |
| 200 | cyclopentyl | 2-methoxyphenyl |
| 201 | cyclopentyl | 3-methoxyphenyl |
| 202 | cyclopentyl | 4-methoxyphenyl |
| 203 | cyclopentyl | 2-nitrophenyl |
| 204 | cyclopentyl | 3-nitrophenyl |
| 205 | cyclopentyl | 4-nitrophenyl |
| 206 | cyclohexyl | phenyl |
| 207 | cyclohexyl | 2-fluorophenyl |
| 208 | cyclohexyl | 3-fluorophenyl |
| 209 | cyclohexyl | 4-fluorophenyl |
| 210 | cyclohexyl | 2-methylphenyl |
| 211 | cyclohexyl | 3-methylphenyl |
| 212 | cyclohexyl | 4-methylphenyl |
| 213 | cyclohexyl | 2-methoxyphenyl |
| 214 | cyclohexyl | 3-methoxyphenyl |
| 215 | cyclohexyl | 4-methoxyphenyl |
| 216 | cyclohexyl | 2-nitrophenyl |
| 217 | cyclohexyl | 3-nitrophenyl |
| 218 | cyclohexyl | 4-nitrophenyl |
| 219 | cycloheptyl | phenyl |
| 220 | cycloheptyl | 2-fluorophenyl |
| 221 | cycloheptyl | 3-fluorophenyl |
| 222 | cycloheptyl | 4-fluorophenyl |
| 223 | cycloheptyl | 2-methylphenyl |
| 224 | cycloheptyl | 3-methylphenyl |
| 225 | cycloheptyl | 4-methylphenyl |
| 226 | cycloheptyl | 2-methoxyphenyl |
| 227 | cycloheptyl | 3-methoxyphenyl |
| 228 | cycloheptyl | 4-methoxyphenyl |
| 229 | cycloheptyl | 2-nitrophenyl |
| 230 | cycloheptyl | 3-nitrophenyl |
| 231 | cycloheptyl | 4-nitrophenyl |
| 232 | cyclooctyl | phenyl |
| 233 | cyclooctyl | 2-fluorophenyl |
| 234 | cyclooctyl | 3-fluorophenyl |
| 235 | cyclooctyl | 4-fluorophenyl |
| 236 | cyclooctyl | 2-methylphenyl |
| 237 | cyclooctyl | 3-methylphenyl |
| 238 | cyclooctyl | 4-methylphenyl |
| 239 | cyclooctyl | 2-methoxyphenyl |
| 240 | cyclooctyl | 3-methoxyphenyl |
| 241 | cyclooctyl | 4-methoxyphenyl |
| 242 | cyclooctyl | 2-nitrophenyl |
| 243 | cyclooctyl | 3-nitrophenyl |
| 244 | cyclooctyl | 4-nitrophenyl |
| 245 | cyclododecyl | phenyl |
| 246 | cyclododecyl | 2-fluorophenyl |
| 247 | cyclododecyl | 3-fluorophenyl |
| 248 | cyclododecyl | 4-fluorophenyl |
| 249 | cyclododecyl | 2-methylphenyl |
| 250 | cyclododecyl | 3-methylphenyl |
| 251 | cyclododecyl | 4-methylphenyl |
| 252 | cyclododecyl | 2-methoxyphenyl |
| 253 | cyclododecyl | 3-methoxyphenyl |
| 254 | cyclododecyl | 4-methoxyphenyl |
| 255 | cyclododecyl | 2-nitrophenyl |
| 256 | cyclododecyl | 3-nitrophenyl |
| 257 | cyclododecyl | 4-nitrophenyl |

Another category of the compounds described herein relates to 3-N-cycloalkyl-5-substituted-2-thioxothiazolidin-4-ones having the formula:

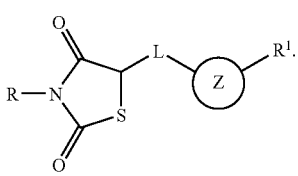

An example of compounds within this category includes compounds wherein Z is a 5-member heteroaryl ring, the compounds having the formula:

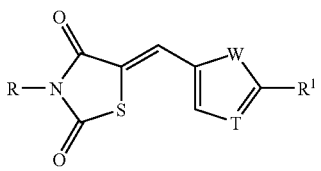

wherein W is O, S, or NH; T is CH or N.

The compounds described herein within this category can be prepared according to the synthesis outlined herein below in Scheme III and described in Example 3.

Scheme III

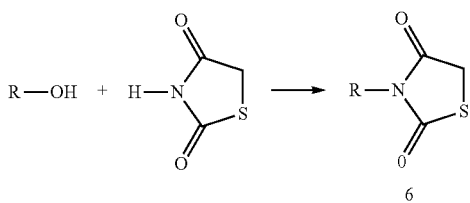

Reagents and conditions: (a) PPh$_3$, DIAD, THF; -78° C. to rt.

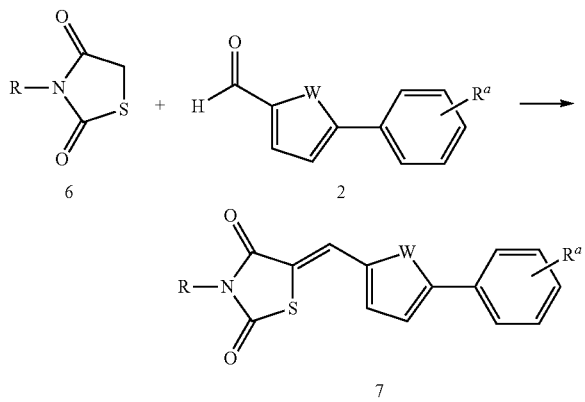

Reagents and conditions: (b) NaOAc, HOAc; reflux.

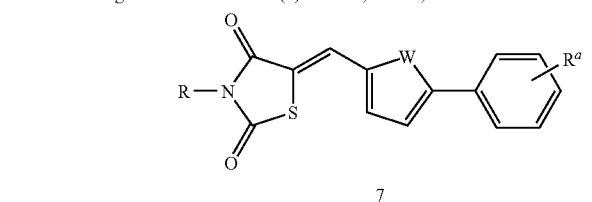

Reagents and conditions: (c) NaOAc, HOAc; reflux.

Examples of compounds as described herein wherein W is O or S and T is CH are listed below in Table III.

TABLE III

| No. | R | W | R$^1$ |
|---|---|---|---|
| 258 | cyclohexyl | O | phenyl |
| 259 | cyclohexyl | O | 3-methylphenyl |
| 260 | cyclohexyl | O | 4-methylphenyl |
| 261 | cyclohexyl | O | 3,4-dimethylphenyl |
| 262 | cyclohexyl | O | 3-methoxyphenyl |
| 263 | cyclohexyl | O | 4-methoxyphenyl |
| 264 | cyclohexyl | O | 3,4-dimethoxyphenyl |
| 265 | cyclohexyl | O | 3-fluorophenyl |
| 266 | cyclohexyl | O | 4-fluorophenyl |
| 267 | cyclohexyl | O | 3,4-difluorophenyl |
| 268 | cyclohexyl | O | 3-chlorophenyl |
| 269 | cyclohexyl | O | 4-chlorophenyl |
| 270 | cyclohexyl | O | 3,4-dichlorophenyl |
| 271 | cyclohexyl | O | 3-nitrophenyl |
| 272 | cyclohexyl | O | 4-nitrophenyl |
| 273 | cyclohexyl | O | 3,4-dinitrophenyl |
| 274 | cyclohexyl | S | phenyl |
| 275 | cyclohexyl | S | 3-methylphenyl |
| 276 | cyclohexyl | S | 4-methylphenyl |
| 277 | cyclohexyl | S | 3,4-dimethylphenyl |
| 278 | cyclohexyl | S | 3-methoxyphenyl |
| 279 | cyclohexyl | S | 4-methoxyphenyl |
| 280 | cyclohexyl | S | 3,4-dimethoxyphenyl |
| 281 | cyclohexyl | S | 3-fluorophenyl |
| 282 | cyclohexyl | S | 4-fluorophenyl |
| 283 | cyclohexyl | S | 3,4-difluorophenyl |
| 284 | cyclohexyl | S | 3-chlorophenyl |
| 285 | cyclohexyl | S | 4-chlorophenyl |
| 286 | cyclohexyl | S | 3,4-dichlorophenyl |
| 287 | cyclohexyl | S | 3-nitrophenyl |
| 288 | cyclohexyl | S | 4-nitrophenyl |
| 289 | cyclohexyl | S | 3,4-dinitrophenyl |
| 290 | cycloheptyl | O | phenyl |
| 291 | cycloheptyl | O | 3-methylphenyl |
| 292 | cycloheptyl | O | 4-methylphenyl |
| 293 | cycloheptyl | O | 3,4-dimethylphenyl |
| 294 | cycloheptyl | O | 3-methoxyphenyl |
| 295 | cycloheptyl | O | 4-methoxyphenyl |
| 296 | cycloheptyl | O | 3,4-dimethoxyphenyl |
| 297 | cycloheptyl | O | 3-fluorophenyl |
| 298 | cycloheptyl | O | 4-fluorophenyl |
| 299 | cycloheptyl | O | 3,4-difluorophenyl |
| 300 | cycloheptyl | O | 3-chlorophenyl |
| 301 | cycloheptyl | O | 4-chlorophenyl |
| 302 | cycloheptyl | O | 3,4-dichlorophenyl |
| 303 | cycloheptyl | O | 3-nitrophenyl |
| 304 | cycloheptyl | O | 4-nitrophenyl |
| 305 | cycloheptyl | O | 3,4-dinitrophenyl |
| 306 | cycloheptyl | S | phenyl |
| 307 | cycloheptyl | S | 3-methylphenyl |
| 308 | cycloheptyl | S | 4-methylphenyl |
| 309 | cycloheptyl | S | 3,4-dimethylphenyl |
| 310 | cycloheptyl | S | 3-methoxyphenyl |
| 311 | cycloheptyl | S | 4-methoxyphenyl |
| 312 | cycloheptyl | S | 3,4-dimethoxyphenyl |
| 313 | cycloheptyl | S | 3-fluorophenyl |
| 314 | cycloheptyl | S | 4-fluorophenyl |
| 315 | cycloheptyl | S | 3,4-difluorophenyl |
| 316 | cycloheptyl | S | 3-chlorophenyl |
| 317 | cycloheptyl | S | 4-chlorophenyl |
| 318 | cycloheptyl | S | 3,4-dichlorophenyl |
| 319 | cycloheptyl | S | 3-nitrophenyl |
| 320 | cycloheptyl | S | 4-nitrophenyl |
| 321 | cycloheptyl | S | 3,4-dinitrophenyl |
| 322 | cyclooctyl | O | phenyl |
| 323 | cyclooctyl | O | 3-methylphenyl |
| 324 | cyclooctyl | O | 4-methylphenyl |
| 325 | cyclooctyl | O | 3,4-dimethylphenyl |
| 326 | cyclooctyl | O | 3-methoxyphenyl |
| 327 | cyclooctyl | O | 4-methoxyphenyl |
| 328 | cyclooctyl | O | 3,4-dimethoxyphenyl |
| 329 | cyclooctyl | O | 3-fluorophenyl |
| 330 | cyclooctyl | O | 4-fluorophenyl |
| 331 | cyclooctyl | O | 3,4-difluorophenyl |
| 332 | cyclooctyl | O | 3-chlorophenyl |
| 333 | cyclooctyl | O | 4-chlorophenyl |
| 334 | cyclooctyl | O | 3,4-dichlorophenyl |
| 335 | cyclooctyl | O | 3-nitrophenyl |

TABLE III-continued

| No. | R | W | R¹ |
|---|---|---|---|
| 336 | cyclooctyl | O | 4-nitrophenyl |
| 337 | cyclooctyl | O | 3,4-dinitrophenyl |
| 338 | cyclooctyl | S | phenyl |
| 339 | cyclooctyl | S | 3-methylphenyl |
| 340 | cyclooctyl | S | 4-methylphenyl |
| 341 | cyclooctyl | S | 3,4-dimethylphenyl |
| 342 | cyclooctyl | S | 3-methoxyphenyl |
| 343 | cyclooctyl | S | 4-methoxyphenyl |
| 344 | cyclooctyl | S | 3,4-dimethoxyphenyl |
| 345 | cyclooctyl | S | 3-fluorophenyl |
| 346 | cyclooctyl | S | 4-fluorophenyl |
| 347 | cyclooctyl | S | 3,4-difluorophenyl |
| 348 | cyclooctyl | S | 3-chlorophenyl |
| 349 | cyclooctyl | S | 4-chlorophenyl |
| 350 | cyclooctyl | S | 3,4-dichlorophenyl |
| 351 | cyclooctyl | S | 3-nitrophenyl |
| 352 | cyclooctyl | S | 4-nitrophenyl |
| 353 | cyclooctyl | S | 3,4-dinitrophenyl |
| 354 | cyclododecyl | O | phenyl |
| 355 | cyclododecyl | O | 3-methylphenyl |
| 356 | cyclododecyl | O | 4-methylphenyl |
| 357 | cyclododecyl | O | 3,4-dimethylphenyl |
| 358 | cyclododecyl | O | 3-methoxyphenyl |
| 359 | cyclododecyl | O | 4-methoxyphenyl |
| 360 | cyclododecyl | O | 3,4-dimethoxyphenyl |
| 361 | cyclododecyl | O | 3-fluorophenyl |
| 362 | cyclododecyl | O | 4-fluorophenyl |
| 363 | cyclododecyl | O | 3,4-difluorophenyl |
| 364 | cyclododecyl | O | 3-chlorophenyl |
| 365 | cyclododecyl | O | 4-chlorophenyl |
| 366 | cyclododecyl | O | 3,4-dichlorophenyl |
| 367 | cyclododecyl | O | 3-nitrophenyl |
| 368 | cyclododecyl | O | 4-nitrophenyl |
| 369 | cyclododecyl | O | 3,4-dinitrophenyl |
| 370 | cyclododecyl | S | phenyl |
| 371 | cyclododecyl | S | 3-methylphenyl |
| 372 | cyclododecyl | S | 4-methylphenyl |
| 373 | cyclododecyl | S | 3,4-dimethylphenyl |
| 374 | cyclododecyl | S | 3-methoxyphenyl |
| 375 | cyclododecyl | S | 4-methoxyphenyl |
| 376 | cyclododecyl | S | 3,4-dimethoxyphenyl |
| 377 | cyclododecyl | S | 3-fluorophenyl |
| 378 | cyclododecyl | S | 4-fluorophenyl |
| 379 | cyclododecyl | S | 3,4-difluorophenyl |
| 380 | cyclododecyl | S | 3-chlorophenyl |
| 381 | cyclododecyl | S | 4-chlorophenyl |
| 382 | cyclododecyl | S | 3,4-dichlorophenyl |
| 383 | cyclododecyl | S | 3-nitrophenyl |
| 384 | cyclododecyl | S | 4-nitrophenyl |
| 385 | cyclododecyl | S | 3,4-dinitrophenyl |

A further category of the compounds described herein relates to 3-N-cycloalkyl-5-substituted-2-thioxothiazolidin-4-ones having the formula:

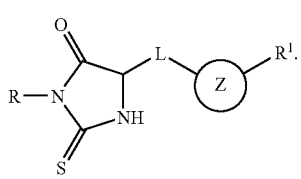

An example of compounds within this category includes compounds wherein Z is a 5-member heteroaryl ring, the compounds having the formula:

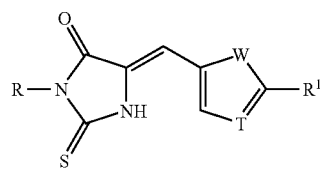

wherein W is O, S, or NH; T is CH or N.

The compounds described herein within this category wherein T is CH can be prepared according to the synthesis outlined herein below in Scheme IV and described in Example 4.

Scheme IV

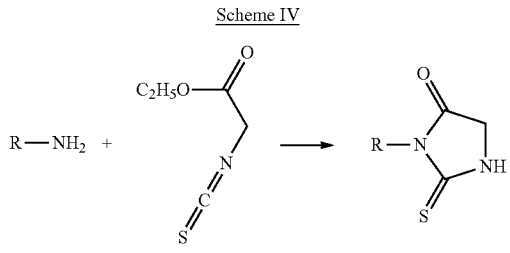

Reagents and conditions: (a) (1) CHCl₃, reflux; (2) EtOH, HCl, reflux.

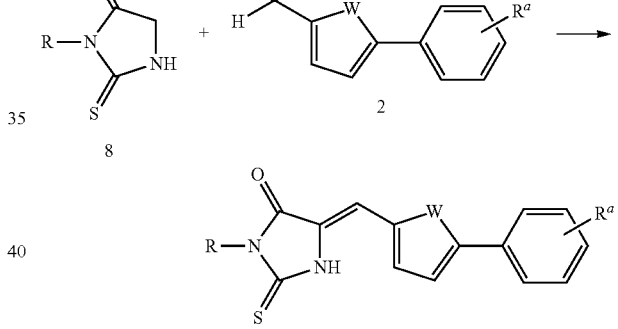

Reagents and conditions: (b) tert-BuOK, THF.

Examples of compounds as described herein wherein T is CH are listed below in Table IV.

TABLE IV

| No. | R | W | R¹ |
|---|---|---|---|
| 386 | cyclohexyl | O | phenyl |
| 387 | cyclohexyl | O | 3-methylphenyl |
| 388 | cyclohexyl | O | 4-methylphenyl |
| 389 | cyclohexyl | O | 3,4-dimethylphenyl |
| 390 | cyclohexyl | O | 3-methoxyphenyl |
| 391 | cyclohexyl | O | 4-methoxyphenyl |
| 392 | cyclohexyl | O | 3,4-dimethoxyphenyl |
| 393 | cyclohexyl | O | 3-fluorophenyl |
| 394 | cyclohexyl | O | 4-fluorophenyl |
| 395 | cyclohexyl | O | 3,4-difluorophenyl |
| 396 | cyclohexyl | O | 3-chlorophenyl |
| 397 | cyclohexyl | O | 4-chlorophenyl |
| 398 | cyclohexyl | O | 3,4-dichlorophenyl |
| 399 | cyclohexyl | O | 3-nitrophenyl |
| 400 | cyclohexyl | O | 4-nitrophenyl |
| 401 | cyclohexyl | O | 3,4-dinitrophenyl |

TABLE IV-continued

| No. | R | W | R¹ |
|---|---|---|---|
| 402 | cyclohexyl | S | phenyl |
| 403 | cyclohexyl | S | 3-methylphenyl |
| 404 | cyclohexyl | S | 4-methylphenyl |
| 405 | cyclohexyl | S | 3,4-dimethylphenyl |
| 406 | cyclohexyl | S | 3-methoxyphenyl |
| 407 | cyclohexyl | S | 4-methoxyphenyl |
| 408 | cyclohexyl | S | 3,4-dimethoxyphenyl |
| 409 | cyclohexyl | S | 3-fluorophenyl |
| 410 | cyclohexyl | S | 4-fluorophenyl |
| 411 | cyclohexyl | S | 3,4-difluorophenyl |
| 412 | cyclohexyl | S | 3-chlorophenyl |
| 413 | cyclohexyl | S | 4-chlorophenyl |
| 414 | cyclohexyl | S | 3,4-dichlorophenyl |
| 415 | cyclohexyl | S | 3-nitrophenyl |
| 416 | cyclohexyl | S | 4-nitrophenyl |
| 417 | cyclohexyl | S | 3,4-dinitrophenyl |
| 418 | cycloheptyl | O | phenyl |
| 419 | cycloheptyl | O | 3-methylphenyl |
| 420 | cycloheptyl | O | 4-methylphenyl |
| 421 | cycloheptyl | O | 3,4-dimethylphenyl |
| 422 | cycloheptyl | O | 3-methoxyphenyl |
| 423 | cycloheptyl | O | 4-methoxyphenyl |
| 424 | cycloheptyl | O | 3,4-dimethoxyphenyl |
| 425 | cycloheptyl | O | 3-fluorophenyl |
| 426 | cycloheptyl | O | 4-fluorophenyl |
| 427 | cycloheptyl | O | 3,4-difluorophenyl |
| 428 | cycloheptyl | O | 3-chlorophenyl |
| 429 | cycloheptyl | O | 4-chlorophenyl |
| 430 | cycloheptyl | O | 3,4-dichlorophenyl |
| 431 | cycloheptyl | O | 3-nitrophenyl |
| 432 | cycloheptyl | O | 4-nitrophenyl |
| 433 | cycloheptyl | O | 3,4-dinitrophenyl |
| 434 | cycloheptyl | S | phenyl |
| 435 | cycloheptyl | S | 3-methylphenyl |
| 436 | cycloheptyl | S | 4-methylphenyl |
| 437 | cycloheptyl | S | 3,4-dimethylphenyl |
| 438 | cycloheptyl | S | 3-methoxyphenyl |
| 439 | cycloheptyl | S | 4-methoxyphenyl |
| 440 | cycloheptyl | S | 3,4-dimethoxyphenyl |
| 441 | cycloheptyl | S | 3-fluorophenyl |
| 442 | cycloheptyl | S | 4-fluorophenyl |
| 443 | cycloheptyl | S | 3,4-difluorophenyl |
| 444 | cycloheptyl | S | 3-chlorophenyl |
| 445 | cycloheptyl | S | 4-chlorophenyl |
| 446 | cycloheptyl | S | 3,4-dichlorophenyl |
| 447 | cycloheptyl | S | 3-nitrophenyl |
| 448 | cycloheptyl | S | 4-nitrophenyl |
| 449 | cycloheptyl | S | 3,4-dinitrophenyl |
| 450 | cyclooctyl | O | phenyl |
| 451 | cyclooctyl | O | 3-methylphenyl |
| 452 | cyclooctyl | O | 4-methylphenyl |
| 453 | cyclooctyl | O | 3,4-dimethylphenyl |
| 454 | cyclooctyl | O | 3-methoxyphenyl |
| 455 | cyclooctyl | O | 4-methoxyphenyl |
| 456 | cyclooctyl | O | 3,4-dimethoxyphenyl |
| 457 | cyclooctyl | O | 3-fluorophenyl |
| 458 | cyclooctyl | O | 4-fluorophenyl |
| 459 | cyclooctyl | O | 3,4-difluorophenyl |
| 460 | cyclooctyl | O | 3-chlorophenyl |
| 461 | cyclooctyl | O | 4-chlorophenyl |
| 462 | cyclooctyl | O | 3,4-dichlorophenyl |
| 463 | cyclooctyl | O | 3-nitrophenyl |
| 464 | cyclooctyl | O | 4-nitrophenyl |
| 465 | cyclooctyl | O | 3,4-dinitrophenyl |
| 466 | cyclooctyl | S | phenyl |
| 467 | cyclooctyl | S | 3-methylphenyl |
| 468 | cyclooctyl | S | 4-methylphenyl |
| 469 | cyclooctyl | S | 3,4-dimethylphenyl |
| 470 | cyclooctyl | S | 3-methoxyphenyl |
| 471 | cyclooctyl | S | 4-methoxyphenyl |
| 472 | cyclooctyl | S | 3,4-dimethoxyphenyl |
| 473 | cyclooctyl | S | 3-fluorophenyl |
| 474 | cyclooctyl | S | 4-fluorophenyl |
| 475 | cyclooctyl | S | 3,4-difluorophenyl |
| 476 | cyclooctyl | S | 3-chlorophenyl |
| 477 | cyclooctyl | S | 4-chlorophenyl |
| 478 | cyclooctyl | S | 3,4-dichlorophenyl |
| 479 | cyclooctyl | S | 3-nitrophenyl |
| 480 | cyclooctyl | S | 4-nitrophenyl |
| 481 | cyclooctyl | S | 3,4-dinitrophenyl |
| 482 | cyclododecyl | O | phenyl |
| 483 | cyclododecyl | O | 3-methylphenyl |
| 484 | cyclododecyl | O | 4-methylphenyl |
| 485 | cyclododecyl | O | 3,4-dimethylphenyl |
| 486 | cyclododecyl | O | 3-methoxyphenyl |
| 487 | cyclododecyl | O | 4-methoxyphenyl |
| 488 | cyclododecyl | O | 3,4-dimethoxyphenyl |
| 489 | cyclododecyl | O | 3-fluorophenyl |
| 490 | cyclododecyl | O | 4-fluorophenyl |
| 491 | cyclododecyl | O | 3,4-difluorophenyl |
| 492 | cyclododecyl | O | 3-chlorophenyl |
| 493 | cyclododecyl | O | 4-chlorophenyl |
| 494 | cyclododecyl | O | 3,4-dichlorophenyl |
| 495 | cyclododecyl | O | 3-nitrophenyl |
| 496 | cyclododecyl | O | 4-nitrophenyl |
| 497 | cyclododecyl | O | 3,4-dinitrophenyl |
| 498 | cyclododecyl | S | phenyl |
| 499 | cyclododecyl | S | 3-methylphenyl |
| 500 | cyclododecyl | S | 4-methylphenyl |
| 501 | cyclododecyl | S | 3,4-dimethylphenyl |
| 502 | cyclododecyl | S | 3-methoxyphenyl |
| 503 | cyclododecyl | S | 4-methoxyphenyl |
| 504 | cyclododecyl | S | 3,4-dimethoxyphenyl |
| 505 | cyclododecyl | S | 3-fluorophenyl |
| 506 | cyclododecyl | S | 4-fluorophenyl |
| 507 | cyclododecyl | S | 3,4-difluorophenyl |
| 508 | cyclododecyl | S | 3-chlorophenyl |
| 509 | cyclododecyl | S | 4-chlorophenyl |
| 510 | cyclododecyl | S | 3,4-dichlorophenyl |
| 511 | cyclododecyl | S | 3-nitrophenyl |
| 512 | cyclododecyl | S | 4-nitrophenyl |
| 513 | cyclododecyl | S | 3,4-dinitrophenyl |

Another category of the compounds described herein relates to 3-N-cycloalkyl-5-substituted-2-thioxothiazolidin-4-ones having the formula:

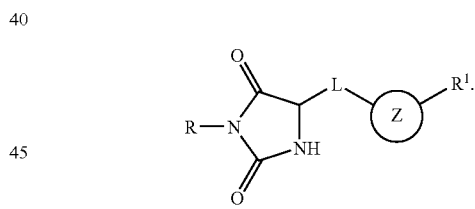

An example of compounds within this category includes compounds wherein Z is a 5-member heteroaryl ring, the compounds having the formula:

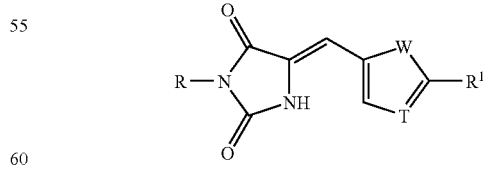

wherein W is O, S, or NH; T is CH or N.

The compounds described herein encompassed within this category wherein T is CH can be prepared according to the synthesis outlined herein below in Scheme V and described in Example 5.

Scheme V

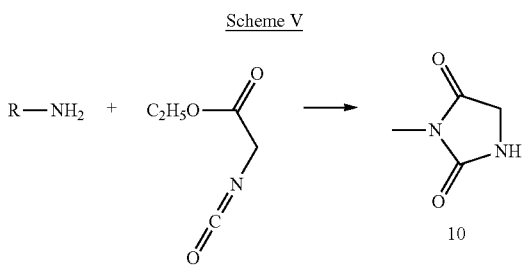

Reagents and conditions: (a)(1) CHCl$_3$, reflux; (2) EtOH, HCl, reflux.

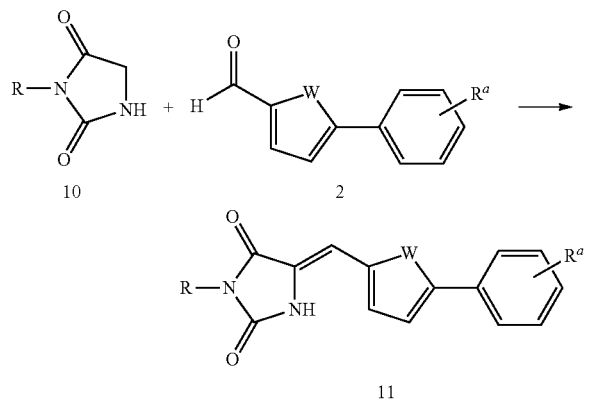

Reagents and conditions: (b) tert-BuOK, THF.

Examples of compounds as described herein wherein T is CH are listed below in Table V.

TABLE V

| No. | R | W | R$^1$ |
| --- | --- | --- | --- |
| 514 | cyclohexyl | O | phenyl |
| 515 | cyclohexyl | O | 3-methylphenyl |
| 516 | cyclohexyl | O | 4-methylphenyl |
| 517 | cyclohexyl | O | 3,4-dimethylphenyl |
| 518 | cyclohexyl | O | 3-methoxyphenyl |
| 519 | cyclohexyl | O | 4-methoxyphenyl |
| 520 | cyclohexyl | O | 3,4-dimethoxyphenyl |
| 521 | cyclohexyl | O | 3-fluorophenyl |
| 522 | cyclohexyl | O | 4-fluorophenyl |
| 523 | cyclohexyl | O | 3,4-difluorophenyl |
| 524 | cyclohexyl | O | 3-chlorophenyl |
| 525 | cyclohexyl | O | 4-chlorophenyl |
| 526 | cyclohexyl | O | 3,4-dichlorophenyl |
| 527 | cyclohexyl | O | 3-nitrophenyl |
| 528 | cyclohexyl | O | 4-nitrophenyl |
| 529 | cyclohexyl | O | 3,4-dinitrophenyl |
| 530 | cyclohexyl | S | phenyl |
| 531 | cyclohexyl | S | 3-methylphenyl |
| 532 | cyclohexyl | S | 4-methylphenyl |
| 533 | cyclohexyl | S | 3,4-dimethylphenyl |
| 534 | cyclohexyl | S | 3-methoxyphenyl |
| 535 | cyclohexyl | S | 4-methoxyphenyl |
| 536 | cyclohexyl | S | 3,4-dimethoxyphenyl |
| 537 | cyclohexyl | S | 3-fluorophenyl |
| 538 | cyclohexyl | S | 4-fluorophenyl |
| 539 | cyclohexyl | S | 3,4-difluorophenyl |
| 540 | cyclohexyl | S | 3-chlorophenyl |
| 541 | cyclohexyl | S | 4-chlorophenyl |
| 542 | cyclohexyl | S | 3,4-dichlorophenyl |
| 543 | cyclohexyl | S | 3-nitrophenyl |
| 544 | cyclohexyl | S | 4-nitrophenyl |
| 545 | cyclohexyl | S | 3,4-dinitrophenyl |
| 546 | cycloheptyl | O | phenyl |
| 547 | cycloheptyl | O | 3-methylphenyl |
| 548 | cycloheptyl | O | 4-methylphenyl |
| 549 | cycloheptyl | O | 3,4-dimethylphenyl |
| 550 | cycloheptyl | O | 3-methoxyphenyl |
| 551 | cycloheptyl | O | 4-methoxyphenyl |
| 552 | cycloheptyl | O | 3,4-dimethoxyphenyl |
| 553 | cycloheptyl | O | 3-fluorophenyl |
| 554 | cycloheptyl | O | 4-fluorophenyl |
| 555 | cycloheptyl | O | 3,4-difluorophenyl |
| 556 | cycloheptyl | O | 3-chlorophenyl |
| 557 | cycloheptyl | O | 4-chlorophenyl |
| 558 | cycloheptyl | O | 3,4-dichlorophenyl |
| 559 | cycloheptyl | O | 3-nitrophenyl |
| 560 | cycloheptyl | O | 4-nitrophenyl |
| 561 | cycloheptyl | O | 3,4-dinitrophenyl |
| 562 | cycloheptyl | S | phenyl |
| 563 | cycloheptyl | S | 3-methylphenyl |
| 564 | cycloheptyl | S | 4-methylphenyl |
| 565 | cycloheptyl | S | 3,4-dimethylphenyl |
| 566 | cycloheptyl | S | 3-methoxyphenyl |
| 567 | cycloheptyl | S | 4-methoxyphenyl |
| 568 | cycloheptyl | S | 3,4-dimethoxyphenyl |
| 569 | cycloheptyl | S | 3-fluorophenyl |
| 570 | cycloheptyl | S | 4-fluorophenyl |
| 571 | cycloheptyl | S | 3,4-difluorophenyl |
| 572 | cycloheptyl | S | 3-chlorophenyl |
| 573 | cycloheptyl | S | 4-chlorophenyl |
| 574 | cycloheptyl | S | 3,4-dichlorophenyl |
| 575 | cycloheptyl | S | 3-nitrophenyl |
| 576 | cycloheptyl | S | 4-nitrophenyl |
| 577 | cycloheptyl | S | 3,4-dinitrophenyl |
| 578 | cyclooctyl | O | phenyl |
| 579 | cyclooctyl | O | 3-methylphenyl |
| 580 | cyclooctyl | O | 4-methylphenyl |
| 581 | cyclooctyl | O | 3,4-dimethylphenyl |
| 582 | cyclooctyl | O | 3-methoxyphenyl |
| 583 | cyclooctyl | O | 4-methoxyphenyl |
| 584 | cyclooctyl | O | 3,4-dimethoxyphenyl |
| 585 | cyclooctyl | O | 3-fluorophenyl |
| 586 | cyclooctyl | O | 4-fluorophenyl |
| 587 | cyclooctyl | O | 3,4-difluorophenyl |
| 588 | cyclooctyl | O | 3-chlorophenyl |
| 589 | cyclooctyl | O | 4-chlorophenyl |
| 590 | cyclooctyl | O | 3,4-dichlorophenyl |
| 591 | cyclooctyl | O | 3-nitrophenyl |
| 592 | cyclooctyl | O | 4-nitrophenyl |
| 593 | cyclooctyl | O | 3,4-dinitrophenyl |
| 594 | cyclooctyl | S | phenyl |
| 595 | cyclooctyl | S | 3-methylphenyl |
| 596 | cyclooctyl | S | 4-methylphenyl |
| 597 | cyclooctyl | S | 3,4-dimethylphenyl |
| 598 | cyclooctyl | S | 3-methoxyphenyl |
| 599 | cyclooctyl | S | 4-methoxyphenyl |
| 600 | cyclooctyl | S | 3,4-dimethoxyphenyl |
| 601 | cyclooctyl | S | 3-fluorophenyl |
| 602 | cyclooctyl | S | 4-fluorophenyl |
| 603 | cyclooctyl | S | 3,4-difluorophenyl |
| 604 | cyclooctyl | S | 3-chlorophenyl |
| 605 | cyclooctyl | S | 4-chlorophenyl |
| 606 | cyclooctyl | S | 3,4-dichlorophenyl |
| 607 | cyclooctyl | S | 3-nitrophenyl |
| 608 | cyclooctyl | S | 4-nitrophenyl |
| 609 | cyclooctyl | S | 3,4-dinitrophenyl |
| 610 | cyclododecyl | O | phenyl |
| 611 | cyclododecyl | O | 3-methylphenyl |
| 612 | cyclododecyl | O | 4-methylphenyl |
| 613 | cyclododecyl | O | 3,4-dimethylphenyl |
| 614 | cyclododecyl | O | 3-methoxyphenyl |
| 615 | cyclododecyl | O | 4-methoxyphenyl |
| 616 | cyclododecyl | O | 3,4-dimethoxyphenyl |
| 617 | cyclododecyl | O | 3-fluorophenyl |
| 618 | cyclododecyl | O | 4-fluorophenyl |
| 619 | cyclododecyl | O | 3,4-difluorophenyl |
| 620 | cyclododecyl | O | 3-chlorophenyl |
| 621 | cyclododecyl | O | 4-chlorophenyl |
| 622 | cyclododecyl | O | 3,4-dichlorophenyl |
| 623 | cyclododecyl | O | 3-nitrophenyl |
| 624 | cyclododecyl | O | 4-nitrophenyl |
| 625 | cyclododecyl | O | 3,4-dinitrophenyl |
| 626 | cyclododecyl | S | phenyl |
| 627 | cyclododecyl | S | 3-methylphenyl |

TABLE V-continued

| No. | R | W | R¹ |
|---|---|---|---|
| 628 | cyclododecyl | S | 4-methylphenyl |
| 629 | cyclododecyl | S | 3,4-dimethylphenyl |
| 630 | cyclododecyl | S | 3-methoxyphenyl |
| 631 | cyclododecyl | S | 4-methoxyphenyl |
| 632 | cyclododecyl | S | 3,4-dimethoxyphenyl |
| 633 | cyclododecyl | S | 3-fluorophenyl |
| 634 | cyclododecyl | S | 4-fluorophenyl |
| 635 | cyclododecyl | S | 3,4-difluorophenyl |
| 636 | cyclododecyl | S | 3-chlorophenyl |
| 637 | cyclododecyl | S | 4-chlorophenyl |
| 638 | cyclododecyl | S | 3,4-dichlorophenyl |
| 639 | cyclododecyl | S | 3-nitrophenyl |
| 640 | cyclododecyl | S | 4-nitrophenyl |
| 641 | cyclododecyl | S | 3,4-dinitrophenyl |

Methods

The compounds described herein can be used for a variety of purposes, including, but not limited to, treating or preventing a viral infection in a subject, inhibiting viral entry into a cell, inhibiting viral mediated membrane fusion, and destabilizing a viral fusion protein. The compounds described herein inhibit at least one (and, optionally, more than one) of the roles of HA, i.e., binding to sialic acid or acting as a membrane fusogen. For example, the compounds described herein can bind or otherwise inhibit the activity of hemagglutinin and/or can inhibit the docking and/or fusion of the virus with the host cell. Further, the compounds described herein can have good efficacy against mutated viruses.

For example, described herein are methods for treating or preventing a viral infection in a subject, the method comprising administering to the subject an effective amount of one or more of the compounds or compositions described herein. As used herein the terms treating or preventing and treating and/or preventing include prevention; delay in onset; diminution, eradication, or delay in exacerbation of signs or symptoms after onset; and prevention of relapse.

Also described herein are methods of inhibiting viral entry into a cell, the method comprising administering to the cell an effective amount of one or more of the compounds or compositions described herein.

Also described herein are methods of inhibiting viral mediated membrane fusion, the method comprising administering to the cell an effective amount of one or more of the compounds or compositions described herein.

Also described herein are methods of destabilizing a viral fusion protein, the method comprising administering to a virally infected cell an effective amount of one or more of the compounds or compositions described herein. By destabilizing a fusion protein, the compounds or compositions described herein can prevent viral mediated membrane fusion and in turn prevent viral infection.

The compounds described herein can be administered to a subject before or after a viral, e.g., influenza, infection has taken place. As shown in the examples, the compounds described herein can both at least partially inhibit the binding of virions to target cells as well as at least partially inhibit viral replication after infection has occurred. Also, the effect of the compounds described herein on virions appears to be irreversible, and thus dilution of the compounds described herein bound to virions is not likely to lower the compounds efficacy against a viral infection. In addition, the compounds described herein can be administered in low concentrations (e.g., as low as 0.4 nM).

Other antiviral approaches have been employed to target other possible targets for viral inhibition. Other compositions used as antivirals or antiretrovirals are broadly classified by the phase of the virus or retrovirus life-cycle that the drug inhibits. For example, other compounds that have been used as viral inhibitors include, but are not limited to, a nucleoside or nucleotide reverse transcriptase inhibitor, a non-nucleoside reverse transcriptase inhibitor, a protease inhibitor, an integrase inhibitor, an RNA polymerase inhibitor, a DNA polymerase inhibitor, a kinase inhibitor, an enzyme inhibitor, an entry inhibitor, an assembly inhibitor, a maturation inhibitor, a M2 inhibitor, or a neuraminidase inhibitor.

Nucleoside and nucleotide reverse transcriptase inhibitors (NRTI) inhibit reverse transcription by being incorporated into the newly synthesized viral DNA and preventing its further elongation. Non-nucleoside and nucleotide reverse transcriptase inhibitors (nNRTI) inhibit reverse transcriptase directly by binding to the enzyme and interfering with its function. Protease inhibitors (PIs) target viral assembly by inhibiting the activity of protease, an enzyme used by HIV to cleave nascent proteins for final assembly of new virons. Integrase inhibitors inhibit the enzyme integrase, which is responsible for integration of viral DNA into the DNA of the infected cell. There are several integrase inhibitors currently under clinical trial, and raltegravir became the first to receive FDA approval in October 2007. Entry inhibitors (or fusion inhibitors) interfere with binding, fusion, and entry of HIV-1 to the host cell by blocking one of several targets. Maraviroc and enfuviritide are the two currently available agents in this class. Maturation inhibitors inhibit the last step in gag processing in which the viral capsid polyprotein is cleaved, thereby blocking the conversion of the polyprotein into the mature capsid protein (p24). Because these viral particles have a defective core, the virions released consist mainly of non-infectious particles. There are no drugs in this class currently available, though two are under investigation, bevirimat and Vivecon™

In any of the methods described herein, the compounds described herein can be administered alone or in combination with one or more second compounds. For example, the compounds described herein can be administered in combination with one or more additional antiviral compounds. Antiviral compounds that can be used in combination with the compounds described herein include, but are not limited to, nucleoside or nucleotide reverse transcriptase inhibitors, non-nucleoside reverse transcriptase inhibitors, protease inhibitors, integrase inhibitors, RNA polymerase inhibitors, DNA polymerase inhibitors, kinase inhibitors, enzyme inhibitors, entry inhibitors, assembly inhibitors, maturation inhibitors, M2 inhibitors, and neuraminidase inhibitors. Examples of such additional antiviral compounds include, but are not limited to amantadine, rimantadine, oseltamivir (Tamilfu®, Roche Laboratories, Nutley, N.J.), zanamivir (Relenza®, GlaxoSmithKline, Philadelphia, Pa.), peramivir, raltegravir, Maraviros, enfuviritide, bevirimat, Vivecon™ (Myriad Genetics, Salt Lake City, Utah), Combivir® (zidovudine+lamivudine, AZT+3TC) (GlaxoSmithKline, Philadelphia, Pa.), Emtriva® (emtricitabine, FTC) (Gilead Sciences, Foster City, Calif.), Epivir® (lamivudine, 3TC) (GlaxoSmithKline, Philadelphia, Pa.), Epzicom® (Kivexa, abacavir+lamivudine, ABC+3TC) (GlaxoSmithKline, Philadelphia, Pa.), Retrovir® (zidovudine, AZT, ZDV) (GlaxoSmithKline, Philadelphia, Pa.), Trizivir® (abacavir+zidovudine+lamivudine, ABC+AZT+3TC) (GlaxoSmithKline, Philadelphia, Pa.), Truvada® (tenofovir DF+emtricitabine, TDF+FTC) (Gilead Sciences, Foster City, Calif.), Videx® & Videx EC® (didanosine, ddI) (Bristol-Myers Squibb, Princeton, N.J.), Viread® (tenofovir disoproxil fumarate, TDF) (Gilead Sciences, Foster City, Calif.), Zerit® (stavudine, d4T) (Bristol-Myers Squibb, Princeton, N.J.), Ziagen® (abacavir, ABC) (GlaxoSmithKline, Philadelphia, Pa.), Racivir™ (RCV) (Pharmasset, Princeton, N.J.), Amdoxovir™ (AMDX, DAPD) (RFS Pharma, Tucker, Ga.), apricitabine (SPD754, AVX754), elvucitabine (ACH-126,443, Beta-L-Fd4C), Immunitin® (HE2000, alpha-epibromide) (Hollis-Eden Pharmaceuticals, San Diego, Calif.), Proleukin® (aldesleukin, Interleukin-2, IL-2) (Chiron Corporation, Emeryville, Calif.), Remune® (HIV-1 Immunogen, Salk vaccine) (Orchestra Therapeutics, Carlsbad, Calif.), BAY 50-4798, IR103, Intelence™ (etravirine, TMC-125) (Tibotec Therapeutics, Irvine, Calif.), Rescriptor® (delavirdine, DLV) (Pfizer, New York, N.Y.), Sustiva® (Stocrin, efavirenz, EFV) (Bristol-Myers Squibb, Princeton, N.J.), Viramune® (nevirapine, NVP) (Boehringer Ingelheim, Ridgefield, Conn.), rilpivirine (TMC-278), Agenerase® (amprenavir, APV) (GlaxoSmithKline, Philadelphia, Pa.), Aptivus® (tipranavir, TPV) (Boehringer Ingelheim, Ridgefield, Conn.), Crixivan® (indinavir, IDV) (Merck, Whitehouse Station, N.J.), Invirase® (saquinavir, SQV) (Roche Laboratories, Nutley, N.J.), Kaletra® (Aluvia®, lopinavir/ritonavir, LPV/r) (Abbott Laboratories, Abbott Park, Ill.), Lexiva® (Telzir®, fosamprenavir, FPV) (GlaxoSmithKline, Philadelphia, Pa.), Norvir® (ritonavir, RTV) (Abbott Laboratories, Abbott Park, Ill.), Prezista® (darunavir, DRV) (Tibotec Therapeutics, Irvine, Calif.), Reyataz® (atazanavir, ATV) (Bristol-Myers Squibb, Princeton, N.J.), Viracept® (nelfinavir, NFV) (Pfizer, Inc., New York, N.Y.), Fuzeon® (enfuvirtide, ENF, T-20) (Roche Laboratories, Inc., Nutley, N.J.), Selzentry® (Celsentri®, maraviroc, UK-427,857) (Pfizer, Inc., New York, N.Y.), Vicriviroc® (SCH-417690, SCH-D) (Schering-Plough, Kenilworth, N.J.), PRO140 (Progenics Pharmaceuticals, Tarrytown, N.Y.), TNX-355 (Tanox, Inc., Houston, Tex.), Isentress® (raltegravir, MK-0518) (Merck, Whitehouse Station, N.J.), Elvitegravir™ (GS-9137) (Gilead Sciences, Foster City, Calif.), Bevirimat™ (PA-457) (Panacos Pharmaceuticals, Inc., Watertown, Mass.), and Droxia® or Hydrea® (hydroxyurea, HU) (Bristol-Myers Squibb, Princeton, N.J.).

The compounds described herein can provide inoculation against viruses prior to attack or the compounds described herein can be used to stop further replication of the invading virus once viral replication has begun. The present compounds, therefore, provide both a method for preventing viral replication in a host cell or host organism, as well as provide a method of treating a host organism (e.g., a subject that has been inoculated or otherwise exposed to an influenza strain, especially sub types of Influenza A or Influenza B, inter alia, A/Udorn/72, X-31, A/PR/8/34, A/NWS/G70C, A/Aich/68, and B/Lee/40).

Also described are methods for treating or preventing viral infection in cells comprising contacting the cells with an effective amount of one or more compounds described herein. The present disclosure further provides a method for treating or preventing a viral infection in a mammal comprising administering to a mammal an effective amount of one or more of the compounds described herein. The present disclosure yet further provides a method for treating or preventing a viral infection in a subject by inhibiting hemagglutinin and/or hemagglutinin having mutations wherein the mutations are based on conservative amino acid substitutions, comprising contacting hemagglutinin with an effective amount of one or more of the compounds described herein. The present disclosure still further provides a method for stopping virus replication in the presence of a host cell in vivo, in vitro, and ex vivo. For example, the present disclosure provides a method for treating or preventing Influenza A or Influenza B viral infection in a subject (e.g., a human) by administering to the subject an effective amount of one or more of the compounds described herein.

The present disclosure provides a method for treating or preventing a viral infection in a cell comprising providing to cells an effective amount of one or more of the compounds described herein or other compounds to destabilize the surface fusion protein on a virus. The present disclosure further provides a method for treating or preventing a viral infection in a mammal comprising administering to the mammal an effective amount of one or more of the compounds described herein or other compounds that destabilize the surface fusion protein on a virus. The present disclosure yet further provides a method for treating a subject by inhibiting a fusion protein and/or a fusion protein having mutations wherein the mutations are based on conservative amino acid substitutions, comprising contacting a fusion protein with an effective amount of one or more of the compounds described herein or other compounds that destabilize the fusion protein. The present disclosure still further provides a method for stopping virus replication in the presence of a host cell in vivo, in vitro, and ex vivo. The present disclosure also provides a method for treating or preventing a viral infection in a human by administering to the human an effective amount of one or more of the compounds described herein or other compounds that destabilize the surface fusion protein on the virion. The present disclosure further relates to the use of one or more of the compounds described herein or other compounds that destabilize the surface fusion protein on the virion for the making of a medicament for treating or preventing a viral infection (for example, an Influenza A or Influenza B viral infection) in a mammal (for example, a human). The present disclosure further relates to the use of the compounds described herein or other compounds that destabilize the surface fusion protein on the virion for the making of a medicament for inhibiting viral fusion protein in the presence of a potential host cell whether in vivo, in vitro, or ex vivo.

As used throughout, a subject is meant an individual. Thus, the subject can include mammals, including humans, primates, domesticated animals (e.g., cats, dogs, etc.), livestock (e.g., cattle, horses, pigs, sheep, goats, etc.), and laboratory animals (e.g., mouse, rabbit, rat, guinea pig, etc.), and birds.

Formulations

The present disclosure also relates to compositions or formulations which comprise the compounds according to the present disclosure. The compositions of the present disclosure comprise an effective amount (e.g., from about 0.001 mg to about 1000 mg, from about 0.01 mg to about 100 mg, and from about 0.1 mg to about 10 mg) of one or more viral inhibitors according to the present disclosure, and one or more excipients.

Excipients are used primarily to serve in delivering a safe, stable, and functional pharmaceutical composition, serving not only as part of the overall vehicle for delivery, but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The compounds of the present disclosure have improved cellular potency, pharmacokinetic properties, as well as improved oral bioavailability.

The term effective amount as used herein refers to an amount of one or more viral inhibitors, effective at dosages and for periods of time necessary to achieve the desired or therapeutic result. Effective dosages and schedules for administering the compositions may be determined empirically, and making such determination is within the skill in the art. The dosage ranges for the administration of the compositions are those large enough to produce the desired effect in which the symptoms of disorder are effected. The dosage should not be so large as to cause adverse side effects, such as unwanted cross-reactions, anaphylactic reactions, and the like. Generally, the dosage will vary with the age, condition, sex and extent of the disease in the subject, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. A typical daily dosage of the compounds described herein used alone might range from about 0.1 mg/kg to up to 10 mg/kg of body weight or more per day, depending on the factors mentioned above.

Following administration of one or more of the compounds described herein, for treating or preventing a viral invention in a subject, preventing viral infection in a subject, inhibiting viral entry into a cell, inhibiting viral mediated membrane fusion, or destabilizing a viral fusion protein, the efficacy of the compound can be assessed in various ways, some of which are known to the skilled practitioner.

The pharmaceutical compositions may be manufactured using any suitable means, e.g., by means of conventional mixing, dissolving, granulating, dragee-making, levigating, emulsifying, encapsulating, entrapping or lyophilizing processes.

Pharmaceutical compositions for use in accordance with the present disclosure thus may be formulated in a conventional manner using one or more physiologically or pharmaceutically acceptable carriers (vehicles, or diluents) comprising excipients and auxiliaries which facilitate processing of the active compounds into preparations which can be used pharmaceutically. Proper formulation is dependent upon the route of administration chosen.

Any suitable method of administering a pharmaceutical composition to a subject may be used in the methods of treatment as described herein, including injection, transmucosal, oral, inhalation, ocular, rectal, long acting implantation, liposomes, emulsion, or sustained release means.

For injection, the agents described herein may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art. For ocular administration, suspensions in an appropriate saline solution are used as is well known in the art.

For oral administration, the compounds can be formulated readily by combining the active compounds with pharmaceutically acceptable carriers well known in the art. Such carriers enable the compounds described herein to be formulated as tablets, pills, dragees, capsules, liquids, gels, syrups, slurries, suspensions and the like, for oral ingestion by a subject to be treated. Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, such as sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

One type of pharmaceutical carrier for hydrophobic compounds described herein is a cosolvent system comprising benzyl alcohol, a nonpolar surfactant, a water-miscible organic polymer, and an aqueous phase.

The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may be substituted for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed.

Additionally, the compounds may be delivered using any suitable sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a prolonged period of time. Depending on the chemical nature and the biological stability of the therapeutic reagent, additional strategies for protein stabilization may be employed.

The pharmaceutical compositions may also comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the agents described herein may be provided as salts with pharmaceutically acceptable counterions. Salts tend to be more soluble in aqueous or other protonic solvents than are the corresponding free base forms.

Other aspects described herein include methods of treating a condition or a disease in a mammal comprising administering to said mammal a pharmaceutical composition described herein.

EXAMPLES

Example 1

Preparation of 3-N-cycloalkyl-5-[(phenyl or substituted phenyl)furan-2-yl]methylene-2-thioxothiazolidin-4-ones or 3-N-cycloalkyl-5-[(phenyl or substituted phenyl)thiophen-2-yl]methylene-2-thioxothiazolidin-4-ones Preparation of 3-cycloalkylrhodanines (1): To a solution of triphenylphosphine (PPh) (6.3 g, 24 mmol) in THF (150 mL) was added DIAD (5.2 g, 24 mmol) at −78° C. within 2 minutes, and the formed mixture was stirred at the same temperature for 10 minutes followed by the addition of the corresponding cycloalkyl alcohol (30 mmol) at the same temperature. After stirring for 10 minutes, rhodanine (2.7 g, 20 mmol) was added to the above solution at −78° C., and the formed mixture was first stirred at −78° C. for 10 minutes, then allowed to warm to room temperature and stir overnight. The reaction was worked up by addition of water (30 mL) and the solid that formed was filtered off, and the aqueous phase extracted with ethyl acetate (3×30 mL). The combined organic phases were washed with brine (20 mL) and dried over anhydrous $Na_2SO_4$. After removal of the solvent under reduced pressure, the crude product was purified by column chromatography on silica gel (ethyl acetate-hexane) to afford the desired compounds.

Preparation of 5-(substituted or unsubstituted)furans or 5-(substituted or unsubstituted)thiophenes (2): To a solution of 5-bromofuran-2-carbaldehyde (1.5 g, 8.57 mmol), the appropriate phenylboronic acid (9 mmol) in toluene (30 mL), ethanol (15 mL) and saturated aqueous $Na_2CO_3$ (30 mL) was added $Pd(PPh_3)_4$ (104 mg, 0.09 mmol) at room temperature, and the reaction mixture was refluxed for 10 hours. After cooling to room temperature, the mixture was concentrated, and the residue was extracted with dichloromethane (3×50 mL). The combined organic phase was first washed with brine (2×10 mL), and then dried over anhydrous $Na_2SO_4$. After removing the solvent, the residue was purified by flash chromatography ($CH_2Cl_2$) to afford the desired products.

Preparation of analogs (3): To a solution of 3-N-cycloalkyl-2-thioxothiazolidin-4-one (0.5 mmol) and 5-aryl or 5-substituted aryl furan-2-yl carboxaldehyde, 5-aryl or 5-substituted aryl thiophene-2-yl carboxaldehyde (0.5 mmol) in AcOH (5 mL) was added anhydrous AcONa (123 mg, 1.5 mmol) at room temperature, and the mixture was refluxed for 16 h. After cooling to room temperature, the mixture was diluted with ethyl acetate (50 mL), and the organic phase was washed with water (3×10 mL), and then dried over anhydrous $Na_2SO_4$. The solvent was removed under vacuum, and the residue was recrystallized from ethyl acetate-hexane to give the desired product.

The following are non-limiting examples of compounds prepared using Scheme I and the procedures of Example 1.

(Z)-3-cyclohexyl-5-{[(3,4-difluorophenyl)furan-2-yl]methylene}-2-thioxothiazolidin-4-one (A37)

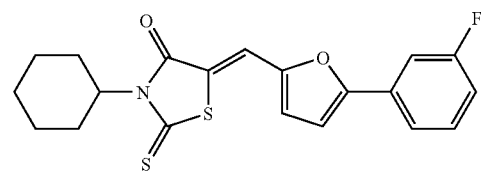 [SMILES: O=C1/C(=C/c2ccc(-c3cccc(F)c3)o2)SC(=S)N1C1CCCCC1]

¹H-NMR (500 MHz, C₆D₆): δ 7.31 (s, 1H), 7.17-7.14 (m, 2H), 6.68-6.63 (m, 1H), 6.15 (d, J=3.6 Hz, 1H), 6.03 (d, J=3.6 Hz, 1H), 5.37-5.32 (m, 1H), 2.70-2.68 (m, 2H), 1.76-1.73 (m, 4H), 1.30-1.16 (m, 4H).

(Z)-3-cyclohexyl-5-{[(4-methylphenyl)furan-2-yl]methylene}-2-thioxothiazolidin-4-one (A3)

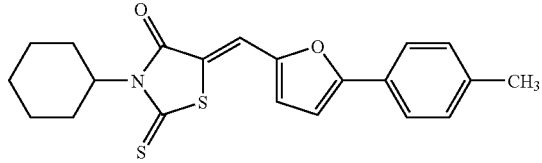

¹H-NMR (500 MHz, C₆D₆): δ 7.66-7.65 (m, 2H), 7.36 (s, 1H), 7.01-6.99 (m, 2H), 6.32 (d, J=3.6 Hz, 1H), 6.24 (d, J=3.6 Hz, 1H), 5.39-5.34 (m, 1H), 2.72-2.70 (m, 2H), 2.18 (s, 3H), 1.75-1.73 (m, 4H), 1.54-1.52 (m, 1H), 1.30-1.16 (m, 4H).

(Z)-3-cyclohexyl-5-{[(4-methoxyphenyl)furan-2-yl]methylene}-2-thioxothiazolidin-4-one (A4)

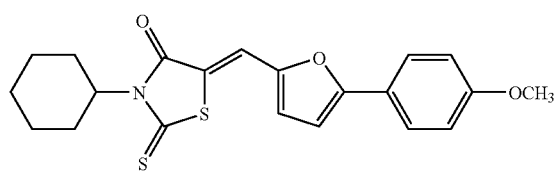 [SMILES: COc1ccc(-c2ccc(/C=C3\SC(=S)N(C4CCCCC4)C3=O)o2)cc1]

¹H-NMR (500 MHz, C₆D₆): δ 7.65-7.63 (m, 2H), 7.37 (s, 1H), 6.76-6.74 (m, 2H), 6.25 (d, J=3.6 Hz, 1H), 6.24 (d, J=3.6 Hz, 1H), 5.41-5.36 (m, 1H), 3.38 (m, 3H), 2.74-2.72 (m, 2H), 1.76-1.74 (m, 4H), 1.55-1.52 (m, 1H), 1.31-1.23 (m, 4H).

(Z)-3-cyclohexyl-5-{[(4-methoxyphenyl)furan-2-yl]methylene}-2-thioxothiazolidin-4-one (A5)

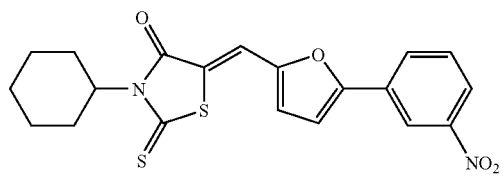

¹H-NMR (500 MHz, C₆D₆): δ 7.65-7.63 (m, 2H), 7.37 (s, 1H), 6.76-6.74 (m, 2H), 6.25 (d, J=3.6 Hz, 1H), 6.24 (d, J=3.6 Hz, 1H), 5.41-5.36 (m, 1H), 3.38 (m, 3H), 2.74-2.72 (m, 2H), 1.76-1.74 (m, 4H), 1.55-1.52 (m, 1H), 1.31-1.23 (m, 4H).

(Z)-3-cyclohexyl-5-{[(4-fluorophenyl)thiophen-2-yl]methylene}-2-thioxothiazolidin-4-one (A6)

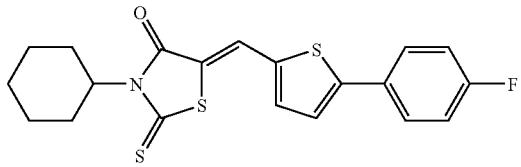 [SMILES: O=C1/C(=C/c2ccc(-c3ccc(F)cc3)s2)SC(=S)N1C1CCCCC1]

¹H-NMR (500 MHz, C₆D₆): δ 7.77 (s, 1H), 7.19-7.16 (m, 2H), 6.84-6.80 (m, 2H), 6.76-6.74 (m, 2H), 5.34-5.29 (m, 1H), 2.70-2.67 (m, 2H), 1.76-1.73 (m, 4H), 1.54-1.48 (m, 1H), 1.30-1.16 (m, 3H).

(Z)-3-cyclooctyl-5-[(5-phenylfuran-2-yl)methylene]-2-thioxothiazolidin-4-one (A8)

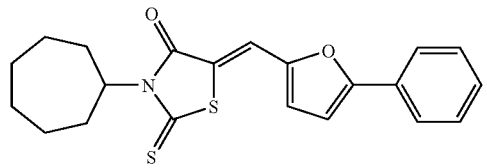 [SMILES: O=C1/C(=C/c2ccc(-c3ccccc3)o2)SC(=S)N1C1CCCCCC1]

¹H-NMR (500 MHz, C₆D₆): δ 7.70 (m, 2H), 7.37 (s, 1H), 7.19-7.16 (m, 2H), 7.13-7.10 (m, 1H), 6.31 (d, J=3.6 Hz, 1H), 6.22 (d, J=3.6 Hz, 1H), 5.70 (br, 1H), 2.64 (br, 2H), 1.81-1.52 (m, 12H).

(Z)-3-cyclooctyl-5-{[(4-fluorophenyl)furan-2-yl]methylene}-2-thioxothiazolidin-4-one (A11)

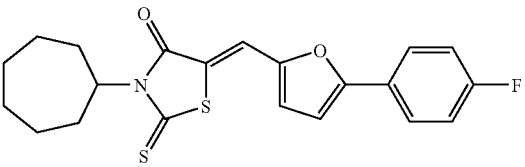 [SMILES: O=C1/C(=C/c2ccc(-c3ccc(F)cc3)o2)SC(=S)N1C1CCCCCC1]

¹H-NMR (500 MHz, C₆D₆): δ 7.44-7.42 (m, 2H), 7.37 (s, 1H), 6.80-6.77 (m, 2H), 6.22 (m, 1H), 6.17 (m, 1H), 5.70 (br, 1H), 2.64 (br, 2H), 2.16 (s, 3H), 1.82-1.47 (m, 12H).

(Z)-3-cyclooctyl-5-{[(3-nitrophenyl)furan-2-yl]methylene}-2-thioxothiazolidin-4-one (A12)

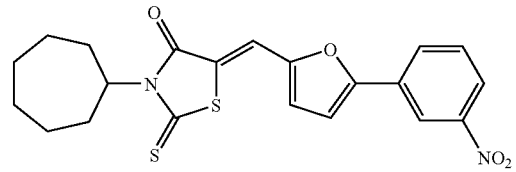 [SMILES: O=C1/C(=C/c2ccc(-c3cccc([N+](=O)[O-])c3)o2)SC(=S)N1C1CCCCCC1]

¹H-1-NMR (500 MHz, C₆D₆): δ 8.24-8.23 (m, 1H), 7.77-7.75 (m, 1H), 7.68-7.67 (m, 1H), 7.33 (s, 1H), 6.80-6.76 (m, 1H), 5.68 (br, 1H), 2.64 (br, 2H), 1.81-1.53 (m, 12H).

(Z)-3-cyclooctyl-5-(5-(4-methoxyphenyl)furan-2-yl)methylene)-2-thioxothiazolidin-4-one (A20)

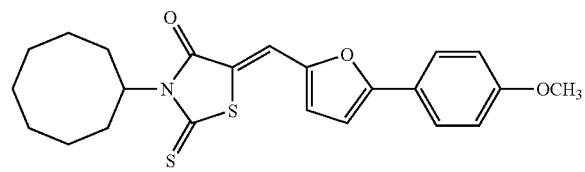 [SMILES: COc1ccc(-c2ccc(/C=C3\SC(=S)N(C4CCCCCCC4)C3=O)o2)cc1]

¹H-NMR (500 MHz, C₆D₆): δ 7.64 (s, 1H), 7.62 (s, 1H), 7.39 (s, 1H), 6.75 (s, 1H), 6.74 (s, 1H), 6.27 (d, J=3.4 Hz, 1H), 6.24 (d, J=3.4 Hz, 1H), 5.72 (br, 1H), 3.38 (s, 3H) 1.83-1.53 (m, 14H); ¹³C-NMR (125 MHz, C₆D₆): δ 194.2, 167.3, 160.6, 158.8, 149.2, 126.3, 122.1, 120.5, 116.8, 114.7, 107.1, 58.1, 54.7, 30.7, 26.4, 26.3, 25.6.

(Z)-3-cycloheptyl-5-((5-(3,4-difluorophenyl)furan-2-yl)methylene)-2-thioxothiazolidin-4-one (A9)

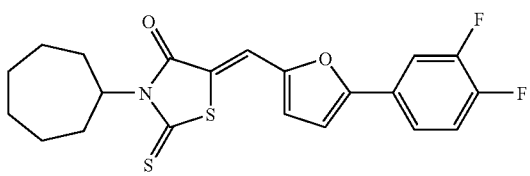 [SMILES: O=C1/C(=C/c2ccc(-c3ccc(F)c(F)c3)o2)SC(=S)N1C1CCCCCC1]

¹H-NMR (500 MHz, C₆D₆): δ 7.33 (s, 1H), 7.19-7.15 (m, 2H), 6.70-6.65 (m, 1H), 6.18 (d, J=3.7 Hz, 1H), 6.06 (d, J=3.7 Hz, 1H), 5.45 (br, 1H), 1.85-1.46 (m, 12H); ¹³C NMR (125 MHz, C₆D₆): δ 193.7, 167.2, 155.6, 151.6, 150.1, 149.8, 149.6, 149.5, 126.3, 126.2, 120.8, 120.7, 119.6, 118.1, 116.2, 113.3, 109.0, 59.6, 30.8, 27.7, 26.0.

(Z)-3-cycloheptyl-2-thioxo-5-((5-p-tolylfuran-2-yl)methylene)thiazolidin-4-one (A10)

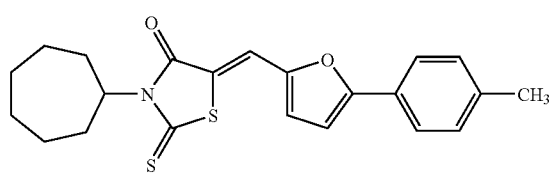 [SMILES: Cc1ccc(-c2ccc(/C=C3\SC(=S)N(C4CCCCCC4)C3=O)o2)cc1]

¹H-NMR (500 MHz, C₆D₆): δ 7.66 (s, 1H), 7.65 (s, 1H), 7.38 (s, 1H), 7.01 (s, 1H), 7.00 (s, 1H), 6.32 (d, J=3.7 Hz, 1H), 6.25 (d, J=3.7 Hz, 1H), 5.48 (Br, 1H), 2.16 (s, 3H), 1.84-1.45 (m, 12H); ¹³C NMR (125 MHz, C₆D₆) δ 194.2, 167.3, 158.7, 149.5, 139.0, 129.8, 126.7, 124.6, 120.2, 116.7, 107.9, 59.5, 30.9, 27.7, 26.0, 21.0.

(Z)-3-cycloheptyl-5-((5-(4-fluorophenyl)furan-2-yl)methylene)-2-thioxothiazolidin-4-one (A11)

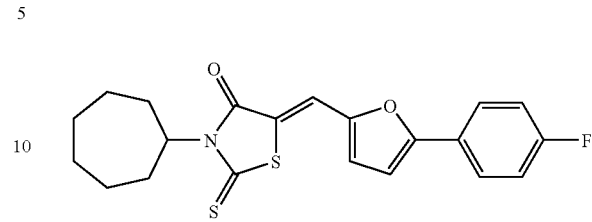

¹H-NMR (500 MHz, C₆D₆): δ 7.44 (d, J=5.4 Hz, 1H), 7.42 (d, J=5.4 Hz, 1H), 7.35 (s, 1H), 6.79 (d, J=8.5 Hz, 1H), 6.77 (d, J=8.5 Hz, 1H), 6.23 (d, J=3.5 Hz, 1H), 6.18 (d, J=3.5 Hz, 1H), 5.46 (Br, 1H), 1.84-1.46 (m, 12H); ¹³C NMR (125 MHz, C₆D₆): δ 193.9, 167.3, 164.1, 162.1, 157.2, 149.8, 126.5, 126.4, 125.5, 119.9, 116.5, 116.2, 116.0, 108.1, 59.5, 30.8, 27.7, 26.0.

(Z)-3-cycloheptyl-5-((5-phenylfuran-2-yl)methylene)-2-thioxothiazolidin-4-one (A8)

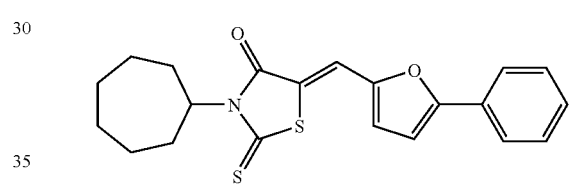

¹H-NMR (500 MHz, C₆D₆): δ 7.70-7.68 (m, 2H), 7.36 (s, 1H), 7.18-7.16 (m, 2H), 7.13-7.11 (m, 1H), 6.32 (d, J=3.6 Hz, 1H), 6.23 (d, J=3.6 Hz, 1H), 5.47 (br, 1H), 1.83-1.46 (m, 12H); ¹³C NMR (125 MHz, C₆D₆): δ 194.1, 167.3, 158.3, 149.8, 129.3, 129.0, 128.8, 124.6, 120.0, 116.7, 108.5, 59.5, 30.9, 27.7, 26.0.

(Z)-3-cyclododecyl-5-((5-phenylfuran-2-yl)methylene)-2-thioxothiazolidin-4-one (A23)

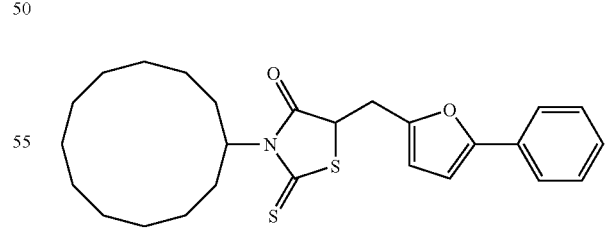

¹H-NMR (500 MHz, C₆D₆): δ 7.70-7.68 (m, 2H), 7.35 (s, 1H), 7.19-7.16 (m, 2H), 7.12-7.09 (m, 1H), 6.31 (d, J=3.6 Hz, 1H), 6.22 (d, J=3.6 Hz, 1H), 5.77 (br, 1H), 2.11 (br, 2H), 1.93 (br, 2H), 1.76 (br, 2H), 1.43 (br, 16H); ¹³C-NMR (125 MHz, C₆D₆): δ 195.5, 167.5, 158.3, 149.8, 129.2, 129.0, 128.8, 124.6, 120.1, 116.7 108.5, 54.1, 27.3, 24.6, 24.3, 23.0, 22.9, 22.4.

(Z)-3-cycloheptyl-5-((5-(3-nitrophenyl)furan-2-yl)methylene)-2-thioxo-thiazolidin-4-one (A12)

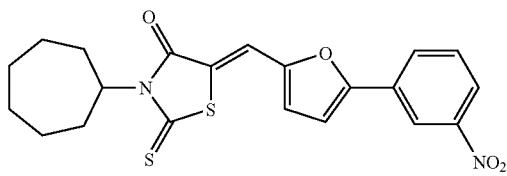

$^1$H-NMR (500 MHz, C$_6$D$_6$): δ 8.25 (s, 1H), 7.77-7.15 (m, 1H), 7.68-7.66 (m, 1H), 7.32 (s, 1H), 6.80-6.76 (m 1H), 6.14 (d, J=3.7 Hz, 1H), 6.08 (d, J=3.7 Hz, 1H), 5.45 (br, 1H), 1.85-1.44 (m, 12H); $^{13}$C NMR (125 MHz, C$_6$D$_6$): δ 193.6, 167.1, 155.1, 150.5, 148.8, 130.3, 129.9, 128.9, 122.6, 119.4, 119.0, 116.1, 110.2, 29.6, 30.9, 27.7, 25.9.

(Z)-3-cyclooctyl-5-((5-(4-fluorophenyl)thiophen-2-yl)methylene)-2-thioxo-thiazolidin-4-one (A21)

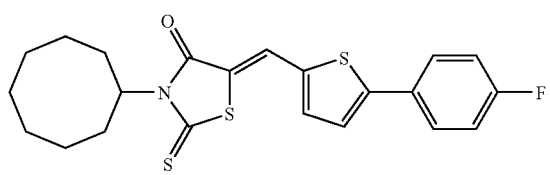 [SMILES: O=C1/C(=C/c2ccc(-c3ccc(F)cc3)s2)SC(=S)N1C1CCCCCCC1]

$^1$H-NMR (500 MHz, C$_6$D$_6$): δ 7.79 (s, 1H), 7.20 (d, J=5.4 Hz, 1H), 7.18 (d, J=5.4 Hz, 1H), 6.83 (d, J=8.5 Hz, 1H), 6.81 (d, J=8.5 Hz, 1H), 6.77 (s, 2H), 5.64 (br, 1H), 1.75-1.52 (m, 14H); $^{13}$C NMR (125 MHz, C$_6$D$_6$) δ 192.1, 167.2, 164.1, 162.1, 150.2, 137.6, 134.5, 129.5, 129.5, 124.4, 123.9, 116.1, 115.9, 58.4, 30.7, 26.4, 26.2, 25.6.

(Z)-3-cyclododecyl-5-((5-(3,4-difluorophenyl)furan-2-yl)methylene)-2-thioxo-thiazolidin-4-one (A241

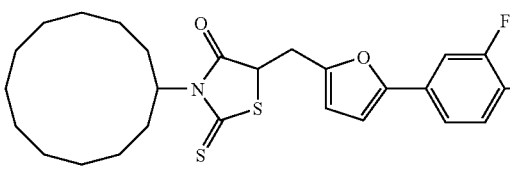

$^1$H-NMR (500 MHz, C$_6$D$_6$): δ 7.31 (s, 1H), 7.19-7.15 (m, 2H), 6.71-6.67 (m, 1H), 6.19 (d, J=3.7 Hz, 1H) 6.08 (d, J=3.7 Hz, 1H) 5.74 (Br, 1H) 2.10 (br, 2H), 1.91 (br, 2H), 1.74 (br, 2H), 1.43 (br, 16H). $^{13}$C-NMR (125 MHz, C$_6$D$_6$): δ 195.0, 167.4, 155.7, 151.8, 151.7, 151.6, 151.5, 150.1, 149.8, 149.7, 149.6, 149.5, 126.3, 126.3, 126.2, 120.8, 120.7, 120.7, 120.7, 119.6, 118.1, 118.0, 116.3, 113.4, 113.3, 109.0, 54.3, 53.0, 27.3, 24.5, 24.3, 23.0, 22.9, 22.4.

(Z)-3-cyclododecyl-2-thioxo-5-((5-p-tolylfuran-2-yl)methylene)thiazolidin-4-one (A25)

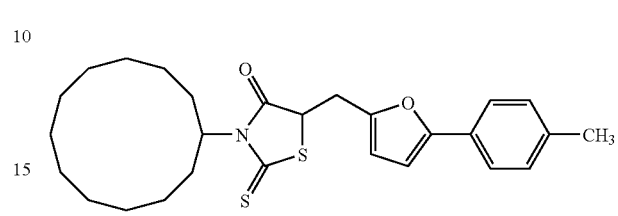

$^1$H-NMR (500 MHz, C$_6$D$_6$): δ 7.65 (s, 1H), 7.64 (s, 1H), 7.36 (s, 1H), 7.01 (s, 1H), 7.00 (s, 1H), 6.32 (d, J=3.6 Hz, 1H), 6.25 (d, J=3.6 Hz, 1H), 5.77 (Br, 1H) 2.16 (s, 3H), 2.13 (br, 2H), 1.94 (br, 2H), 1.77 (br, 2H), 1.43 (br, 16H); $^{13}$C-NMR (125 MHz, C$_6$D$_6$) δ 195.5, 167.5, 158.7, 149.5, 139.0, 129.8, 127.2, 124.5, 119.7, 106.6, 54.1, 53.1, 24.1, 22.7, 22.6, 21.0.

(Z)-3-cyclododecyl-5-((5-(3-nitrophenyl)furan-2-yl)methylene)-2-thioxo-thiazolidin-4-one (A27)

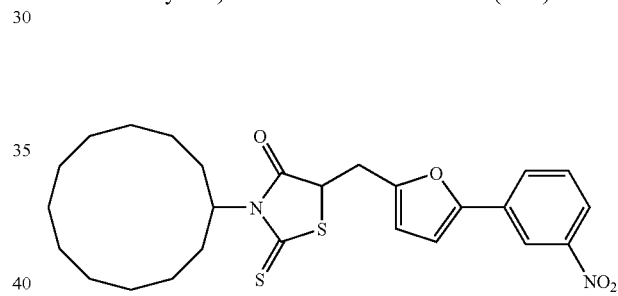

$^1$H-NMR (500 MHz, C$_6$D$_6$) δ 8.24 (s, 1H), 7.76 (d, J=7.6 Hz, 1H), 7.67 (d, J=7.6 Hz, 1H), 7.32 (s, 1H), 6.81-6.78 (m, 1H), 6.13 (d, J=3.7 Hz, 1H), 6.09 (d, J=3.7 Hz, 1H), 5.75 (br, 1H), 2.10 (br, 2H), 1.92 (br, 2H), 1.75 (br, 2H), 1.43 (br, 16H).

(Z)-3-cyclododecyl-5-((5-(4-fluorophenyl)furan-2-yl)methylene)-2-thioxo-thiazolidin-4-one (A26)

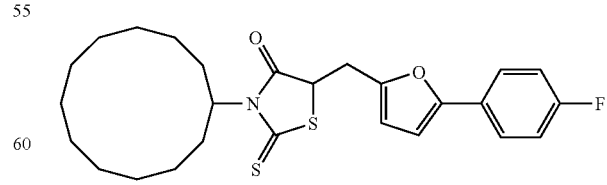

$^1$H-NMR (500 MHz, C$_6$D$_6$) δ 7.78 (s, 1H), 7.19 (d, J=5.3 Hz, 1H), 7.17 (d, J=5.3 Hz, 1H), 6.83 (d, J=8.5 Hz, 1H), 6.81 (d, J=8.5 Hz, 1H), 6.76 (s, 2H), 5.72 (Br, 1H), 2.09 (br, 2H), 1.91 (br, 2H), 1.73 (br, 2H), 1.43 (br, 16H); $^{13}$C-NMR (125

MHz, C₆D₆) M93.4, 167.5, 164.1, 162.1, 150.3, 137.5, 134.6, 129.5, 129.4, 124.4, 124.1, 116.1, 115.9, 54.4, 27.3, 24.5, 24.3, 23.0, 22.9, 22.4.

(Z)-3-cyclododecyl-5-(5-(4-fluorophenyl)thiophen-2-yl)methylene)-2-thioxo-thiazolidin-4-one (A29)

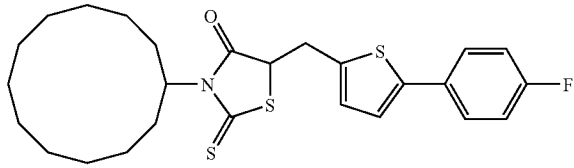 [SMILES: O=C1C(Cc2ccc(-c3ccc(F)cc3)s2)SC(=S)N1C1CCCCCCCCCCC1]

¹H-NMR (500 MHz, C₆D₆): δ 7.78 (s, 1H), 7.19 (d, J=5.3 Hz, 1H), 7.17 (d, J=5.3 Hz, 1H), 6.83 (d, J=8.5 Hz, 1H), 6.81 (d, J=8.5 Hz, 1H), 6.76 (s, 2H), 5.72 (Br, 1H), 2.09 (br, 2H), 1.91 (br, 2H), 1.74 (br, 2H), 1.42 (br, 16H); ¹³C NMR (125 MHz, C₆D₆): δ 193.4, 167.5, 164.1, 162.1, 150.3, 137.5, 134.6, 129.5, 129.4, 124.4, 124.1, 116.1, 115.9, 54.4, 27.3, 24.5, 24.3, 23.0, 22.9, 22.4.

(Z)-3-(bicyclo[2.2.1]heptan-2-yl)-2-thioxo-5-((5-p-tolylfuran-2-yl)methylene)-thiazolidin-4-one (A30)

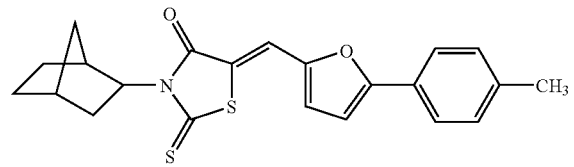 [SMILES: Cc1ccc(-c2ccc(/C=C3\SC(=S)N(C4CC5CCC4C5)C3=O)o2)cc1]

¹H-NMR (500 MHz, C₆D₆): δ 7.66 (s, 1H), 7.65 (s, 1H), 7.35 (s, 1H), 7.01 (s, 1H), 7.00 (s, 1H), 6.32 (d, J=3.5 Hz, 1H), 6.24 (d, J=3.5 Hz, 1H), 5.16 (m, 1H) 2.66-2.55 (m, 3H), 2.38 (s, 1H), 2.16 (s, 3H), 1.76-1.70 (m, 1H), 1.48-1.28 (m, 4H), 1.13-1.11 (m, 1H); ¹³C-NMR (125 MHz, C₆D₆): δ 196.3, 167.5, 158.6, 149.6, 139.0, 129.8, 126.7, 124.6, 120.0, 116.7, 107.9, 62.8, 41.7, 38.0, 36.7, 35.2, 29.4, 28.1, 21.0.

(Z)-3-(bicyclo[2.2.1]heptan-2-yl)-5-((5-(4-methoxyphenyl)furan-2-yl)methylene)-2-thioxothiazolidin-4-one (A31)

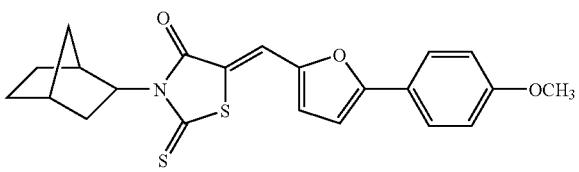 [SMILES: COc1ccc(-c2ccc(/C=C3\SC(=S)N(C4CC5CCC4C5)C3=O)o2)cc1]

¹H-NMR (500 MHz, C₆D₆): δ 7.64 (s, 1H), 7.62 (s, 1H), 7.36 (s, 1H), 6.76 (s, 1H), 6.74 (s, 1H), 6.27 (d, J=3.3 Hz, 1H), 6.25 (d, J=3.3 Hz, 1H), 5.17 (m, 1H), 3.39 (s, 1H), 2.67-2.57 (m, 3H), 2.39 (s, 1H), 2.16 (s, 3H), 1.77-1.72 (m, 1H), 1.52-1.29 (m, 4H), 1.13-1.11 (m, 1H); ¹³C-NMR (125 MHz, C₆D₆): δ 196.3, 167.5, 160.6, 158.7, 149.3, 126.2, 122.1, 120.4, 119.4, 116.8, 114.7, 107.1, 62.8, 54.7, 41.7, 38.0, 36.7, 35.2, 29.4, 28.1.

(Z)-3-(bicyclo[2.2.1]heptan-2-yl)-5-((5-(3,4-difluorophenyl)furan-2-yl)methylene)-2-thioxothiazolidin-4-one (A32)

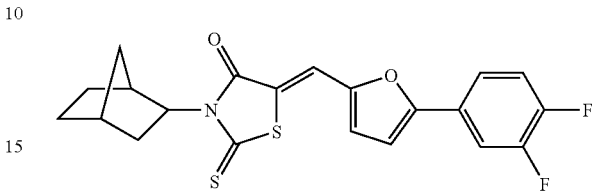

¹H-NMR (500 MHz, C₆D₆): δ 7.30 (s, 1H), 7.18-7.15 (m, 2H), 6.69-6.64 (m, 1H), 6.15 (d, J=3.7 Hz, 1H), 6.04 (d, J=3.7 Hz, 1H), 5.13 (m, 1H), 2.63-2.53 (m, 3H), 2.38 (s, 1H), 1.76-1.70 (m, 1H), 1.51-1.28 (m, 4H), 1.13-1.10 (m, 1H); ¹³C-NMR (125 MHz, C₆D₆): δ 195.8, 167.4, 155.6, 151.8, 151.7, 151.6, 151.5, 150.2, 149.8, 149.7, 149.5, 121.1, 120.8, 120.7, 120.7, 120.7, 119.4, 118.1, 118.0, 116.2, 113.4, 113.3, 109.0, 62.9, 41.7, 38.0, 36.7, 35.2, 29.3, 28.1.

(Z)-3-(bicyclo[2.2.1]heptan-2-yl)-5-((5-(4-fluorophenyl)furan-2-yl)methylene)-2-thioxothiazolidin-4-one (A33)

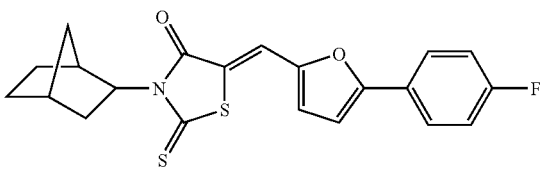 [SMILES: O=C1/C(=C/c2ccc(-c3ccc(F)cc3)o2)SC(=S)N1C1CC2CCC1C2]

¹H-NMR (500 MHz, C₆D₆): δ 7.44 (d, J=5.3 Hz, 1H), 7.42 (d, J=5.3 Hz, 1H), 7.42 (s, 1H), 6.79 (d, J=8.5 Hz, 1H), 6.77 (d, J=8.5 Hz, 1H), 6.21 (d, J=3.6 Hz, 1H), 6.17 (d, J=3.6 Hz, 1H), 5.14 (m, 1H), 2.64-2.54 (m, 3H), 2.38 (s, 1H), 1.77-1.71 (m, 1H), 1.52-1.29 (m, 4H), 1.14-1.11 (m, 1H); ¹³C-NMR (125 MHz, C₆D₆): δ 196.1, 167.5, 164.0, 162.1, 157.2, 149.8, 126.5, 126.4, 125.5, 120.4, 119.8, 116.5, 116.2, 116.0, 108.1, 62.9, 41.7, 38.0, 36.7, 35.2, 29.4, 28.1.

(Z)-3-(bicyclo[2.2.1]heptan-2-yl)-5-((5-(2-fluoropyridin-3-yl)furan-2-yl)methylene)-2-thioxothiazolidin-4-one (A34)

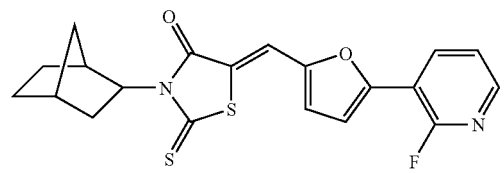 [SMILES: O=C1/C(=C/c2ccc(-c3cccnc3F)o2)SC(=S)N1C1CC2CCC1C2]

¹H-NMR (500 MHz, C₅D₅N): δ 8.11 (m, 1H), 8.00 (d, J=3.6 Hz, 1H), 7.62 (s, 1H), 7.07 (d, J=3.6 Hz, 1H), 6.27 (d, J=6.7 Hz, 1H), 6.25 (d, J=6.7 Hz, 1H), 5.06 (m, 1H), 2.58 (s, 1H), 2.51-2.47 (m, 2H), 2.31 (s, 1H), 1.74-1.69 (m, 1H), 1.47-1.08 (m, 5H); $^{13}$C-NMR (125 MHz, C$_5$D$_5$N): δ 195.7, 166.6, 159.0, 154.5, 134.5, 120.9, 119.1, 118.5, 116.4, 113.5, 104.6, 62.0, 40.7, 37.0, 35.7, 34.2, 28.4, 27.2.

(Z)-3-(bicyclo[2.2.1]heptan-2-yl)-5-((5-(3-nitrophenyl)furan-2-yl)methylene)-2-thioxothiazolidin-4-one (A35)

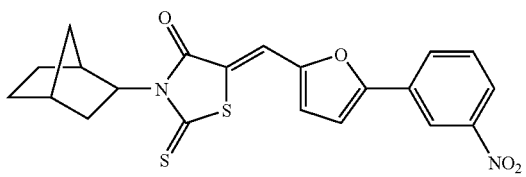 [SMILES: O=C1/C(=C/c2ccc(-c3cccc([N+](=O)[O-])c3)o2)SC(=S)N1C1CC2CCC1C2]

$^1$H-NMR (500 MHz, C$_6$D$_6$): δ 8.24 (s, 1H), 7.75 (d, J=7.7 Hz, 1H), 7.67 (d, J=7.7 Hz, 1H), 7.29 (s, 1H), 6.78-6.74 (m, 1H), 6.10 (d, J=3.7 Hz, 1H), 6.05 (d, J=3.7 Hz, 1H), 5.12 (m, 1H), 2.62-2.52 (m, 3H), 2.38 (s, 1H), 1.76-1.70 (m, 1H), 1.50-1.29 (m, 4H), 1.13-1.11 (m, 1H).

(Z)-3-(bicyclo[2.2.1]heptan-2-yl)-5-((5-(3-nitrophenyl)furan-2-yl)methylene)-2-thioxothiazolidin-4-one (A36)

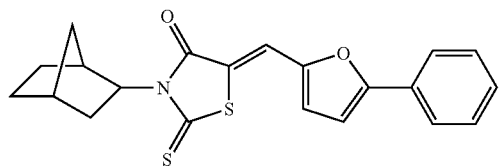

$^1$H-NMR (500 MHz, C$_6$D$_6$): δ 7.70-7.68 (m, 2H), 7.33 (s, 1H), 7.19-7.16 (m, 2H), 7.13-7.11 (m, 1H), 6.32 (d, J=3.6 Hz, 1H), 6.23 (d, J=3.6 Hz, 1H), 5.14 (m, 1H), 2.64-2.54 (m, 3H), 2.38 (s, 1H), 1.77-1.70 (m, 1H), 1.48-1.28 (m, 4H), 1.14-1.11 (m, 1H); $^{13}$C-NMR (125 MHz, C$_6$D$_6$): δ 196.2, 167.5, 158.2, 149.9, 129.3, 129.0, 128.8, 124.5, 120.4, 119.9, 116.6, 108.5, 62.8, 41.7, 38.0, 36.7, 35.2, 29.4, 28.1.

Example 2

Preparation of 3-N-cycloalkyl-5-(Substituted or Unsubstituted Biphenyl-3-yl)methylene-2-thioxothiazolidin-4-ones Preparation of analogs (5): To a solution of 3-N-cycloalkyl-2-thioxothiazolidin-4-one (0.5 mmol) and substituted or unsubstituted biphenyl-3-carboxaldehyde (0.5 mmol) in AcOH (5 mL) was added anhydrous AcONa (123 mg, 1.5 mmol) at room temperature, and the mixture was refluxed for 16 h. After cooling to room temperature, the mixture was diluted with ethyl acetate (50 mL), and the organic phase was washed with water (3×10 mL), and then dried over anhydrous Na$_2$SO$_4$. The solvent was removed under vacuum, and the residue was recrystallized from ethyl acetate-hexane to give the product.

The following are non-limiting examples of compounds prepared using Scheme II and the procedures of Example 2.

(Z)-3-cyclohexyl-5-[(4'-fluorobiphenyl-4-yl)methylene]-2-thioxothiazolidin-4-one (F1)

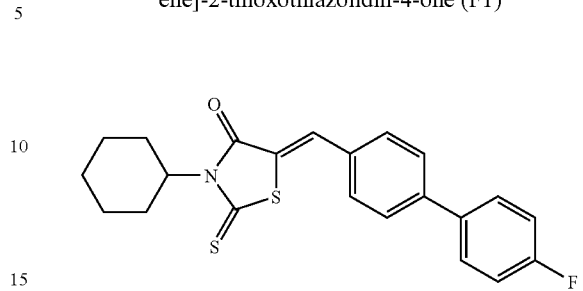

$^1$H-NMR (500 MHz, CDCl$_3$): δ 7.66-7.54 (m, 7H), 7.17-7.14 (m, 2H), 5.05-5.00 (m, 2H), 2.45-2.42 (m, 2H), 1.91-1.89 (m, 2H), 1.73-1.70 (m, 3H), 1.44-1.27 (m, 3H).

(Z)-3-cyclooctyl-5-[(3'-fluorobiphenyl-3-yl)methylene]-2-thioxothiazolidin-4-one (F2)

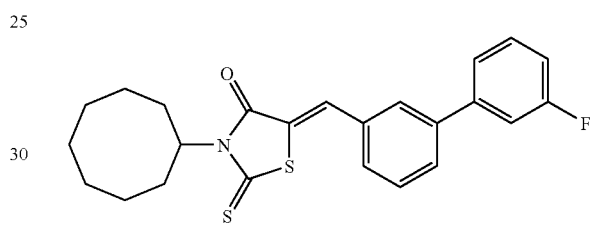

$^1$H-NMR (500 MHz, CDCl$_3$): δ 7.68-7.08 (m, 9H), 5.38-5.35 (m, 1H), 2.40 (m, 2H), 1.84-1.67 (m, 12H).

(Z)-3-cycloheptyl-5-[(3'-fluorobiphenyl-3-yl)methylene]-2-thioxothiazolidin-4-one (F3)

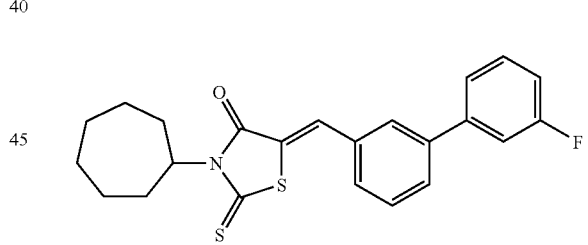

$^1$H-NMR (500 MHz, CDCl$_3$): δ 7.68-7.08 (m, 9H), 5.38-5.35 (m, 1H), 2.40 (m, 2H), 1.84-1.67 (m, 12H).

(Z)-3-cycloheptyl-5-[(3'-fluorobiphenyl-3-yl)methylene]-2-thioxothiazolidin-4-one (F4)

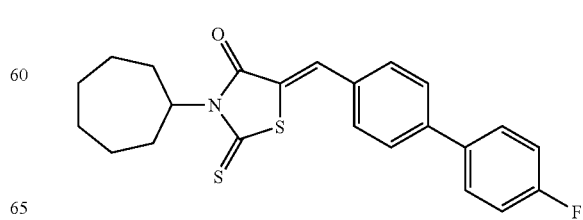

¹H-NMR (500 MHz, CDCl₃): δ 7.66-7.54 (m, 7H), 7.18-7.14 (m, 2H), 5.16 (br, 1H), 2.40-2.39 (m, 2H), 1.83-1.54 (m, 12H).

(Z)-3-cyclooctyl-5-[(4'-fluorobiphenyl-4-yl)methylene]-2-thioxothiazolidin-4-one (F5)

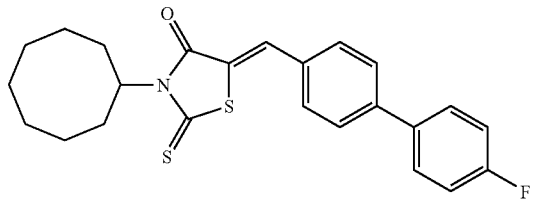 [SMILES: O=C1/C(=C/c2ccc(-c3ccc(F)cc3)cc2)SC(=S)N1C1CCCCCCC1]

¹H-NMR (500 MHz, CDCl₃): δ 7.66-7.54 (m, 8H), 7.18-7.14 (m, 2H), 5.37 (br, 1H), 2.40-2.39 (m, 2H), 1.84-1.57 (m, 14H).

(Z)-3-cyclopentyl-5-[(4'-fluorobiphenyl-4-yl)methylene]-2-thioxothiazolidin-4-one (F6)

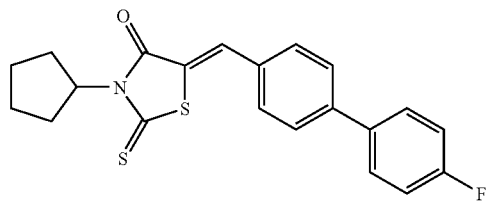 [SMILES: O=C1/C(=C/c2ccc(-c3ccc(F)cc3)cc2)SC(=S)N1C1CCCC1]

¹H-NMR (500 MHz, CDCl₃): δ 7.67-7.54 (m, 7H), 7.18-7.15 (m, 2H), 5.54-5.47 (m, 1H), 2.27-1.66 (m, 8H).

(Z)-3-adamantane-5-[(3'-fluorobiphenyl-3-yl)methylene]-2-thioxothiazolidin-4-one (F7)

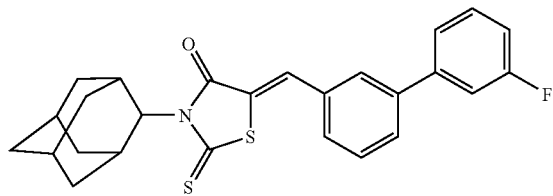 [SMILES: O=C1/C(=C/c2cccc(-c3cccc(F)c3)c2)SC(=S)N1C1C2CC3CC(C2)CC1C3]

¹H-NMR (500 MHz, CDCl₃): δ 7.68-7.08 (m, 7H), 5.15 (s, 1H), 2.52-2.44 (m, 4H), 2.00-1.73 (m, 10H).

Example 3

Preparation of 3-N-cycloalkyl-5-[(Phenyl or Substituted Phenyl)furan-2-yl]methylene-thiazolidine-2,4-diones or 3-N-cycloalkyl-5-[(Phenyl or Substituted Phenyl)thiophen-2-yl]methylenethiazolidine-2,4-diones Preparation of 3-cycloalkylthiazolidine-2,4-diones (6): To a solution of triphenylphosphine (PPh₃) (6.3 g, 24 mmol) in THF (150 mL) was added DIAD (5.2 g, 24 mmol) at −78° C. within 2 minutes, and the formed mixture was stirred at the same temperature for 10 minutes followed by the addition of the corresponding cycloalkyl alcohol (30 mmol) at the same temperature. After stirring for 10 minutes, thiazolidine-2,4-dione (2.3 g, 20 mmol) was added to the above solution at −78° C., and the formed mixture was first stirred at −78° C. for 10 minutes then allowed to warm to room temperature and stir overnight. The reaction was worked up by addition of water (30 mL) and the solid that formed was filtered off, and the aqueous phase extracted with ethyl acetate (3×30 mL). The combined organic phases were washed with brine (20 mL) and dried over anhydrous Na₂SO₄. After removal of the solvent under reduced pressure, the crude product was purified by column chromatography on silica gel (ethyl acetate-hexane) to afford the desired compounds.

Preparation of analogs thiazolidine-2,4-dione analogs (7): To a solution of 3-N-cycloalkyl-thiazolidine-2,4-dione (0.5 mmol) and 5-aryl or 5-substituted aryl furan-2-yl carboxaldehyde, 5-aryl or 5-substituted aryl thiophene-2-yl carboxaldehyde, (0.5 mmol) in AcOH (5 mL) was added anhydrous AcONa (123 mg, 1.5 mmol) at room temperature, and the mixture was refluxed for 16 h. After cooling to room temperature, the mixture was diluted with ethyl acetate (50 mL), and the organic phase was washed with water (3×10 mL), and then dried over anhydrous Na₂SO₄. The solvent was removed under vacuum, and the residue was recrystallized from ethyl acetate-hexane to give the desired product.

The following are non-limiting examples of compounds prepared using Scheme III and the procedures of Example 3.

(Z)-3-cyclohexyl-5-{[(3-nitrophenyl)furan-2-yl]methylene}thiazolidine-2,4-dione (B1)

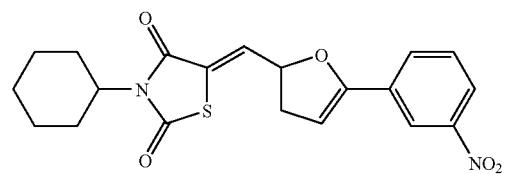 [SMILES: O=C1S/C(=C\C2CC=C(c3cccc([N+](=O)[O-])c3)O2)C(=O)N1C1CCCCC1]

¹H-NMR (500 MHz, C₆D₆): δ 8.26 (m, 1H), 7.79-7.76 (m, 1H), 7.62 (m, 2H), 6.86-6.83 (m, 1H), 6.14 (d, J=3.6 Hz, 1H), 6.09 (d, J=3.6 Hz, 1H), 4.53-4.48 (m, 1H), 2.49-2.42 (m, 2H), 1.69-1.64 (m, 5H), 1.48 (m, 3H).

(Z)-3-cyclohexyl-5-{[(4-methoxyphenyl)furan-2-yl]methylene}thiazolidine-2,4-dione (B2)

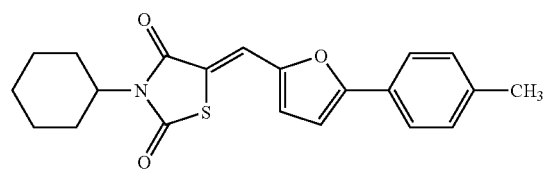 [SMILES: Cc1ccc(-c2ccc(/C=C3\SC(=O)N(C4CCCCC4)C3=O)o2)cc1]

¹H-NMR (500 MHz, C₆D₆): δ 7.70 (s, 1H), 7.65-7.63 (m, 2H), 6.84-6.82 (m, 2H), 6.29 (d, J=3.6 Hz, 1H), 6.28 (d, J=3.6

Hz, 1H), 4.56-4.50 (m, 1H), 3.40 (s, 3H), 2.52-2.45 (m, 2H), 1.68-1.66 (m, 4H), 1.49 (m, 1H), 1.21-1.10 (m, 3H).

(Z)-3-cyclohexyl-5-[(5-phenylfuran-2-yl)methylene]thiazolidine-2,4-dione (B4)

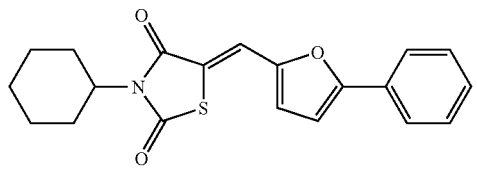

$^1$H-NMR (500 MHz, C$_6$D$_6$): δ 7.69-7.68 (s, 2H), 7.66 (s, 1H), 7.25-7.21 (m, 2H), 7.15-7.12 (m, 1H), 6.33 (d, J=3.6 Hz, 1H), 6.24 (d, J=3.6 Hz, 1H), 4.54-4.48 (m, 1H), 2.50-2.43 (m, 2H), 1.68-1.64 (m, 4H), 1.49 (m, 1H), 1.20-1.10 (m, 3H).

(Z)-3-cyclohexyl-5-{[(4-fluorophenyl)thiophen-2-yl]methylene}thiazolidine-2,4-dione (B5)

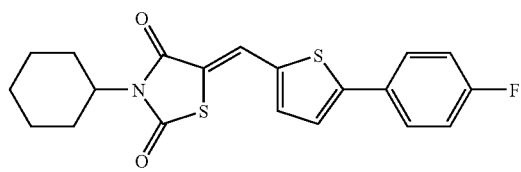

$^1$H-NMR (500 MHz, C$_6$D$_6$): δ 8.09 (s, 1H), 7.20-7.17 (m, 2H), 6.82-6.77 (m, 4H), 4.52-4.47 (m, 1H), 2.48-2.40 (m, 2H), 1.69-1.63 (m, 4H), 1.48 (m, 1H), 1.17-1.12 (m, 3H).

(Z)-3-cyclohexyl-5-{[(3,4-difluorophenyl)furan-2-yl]methylene}thiazolidine-2,4-dione (B6)

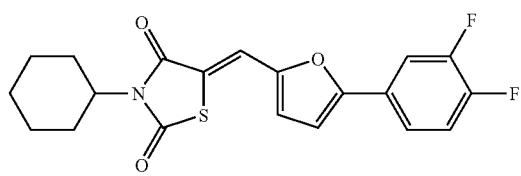 [SMILES: O=C1S/C(=C\c2ccc(-c3ccc(F)c(F)c3)o2)C(=O)N1C1CCCCC1]

$^1$H-NMR (500 MHz, C$_6$D$_6$): δ 7.63 (s, 1H), 7.22-7.18 (m, 1H), 7.12-7.09 (m, 1H), 6.77-6.72 (m, 1H), 6.18 (d, J=3.6 Hz, 1H), 6.07 (d, J=3.6 Hz, 1H), 4.54-4.47 (m, 1H), 2.49-2.42 (m, 2H), 1.69-1.64 (m, 4H), 1.48 (m, 1H), 1.20-1.08 (m, 3H).

(Z)-3-cyclohexyl-5-{[(4-fluorophenyl)furan-2-yl]methylene}thiazolidine-2,4-drone (B7)

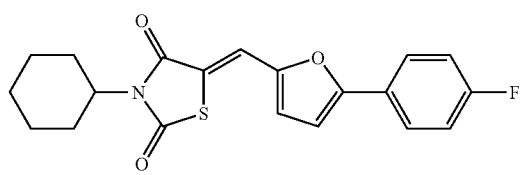 [SMILES: O=C1S/C(=C\c2ccc(-c3ccc(F)cc3)o2)C(=O)N1C1CCCCC1]

$^1$H-NMR (500 MHz, C$_6$D$_6$): δ 7.66 (s, 1H), 7.44-7.41 (m, 2H), 6.87-6.84 (m, 2H), 6.23 (d, J=3.6 Hz, 1H), 6.19 (d, J=3.6 Hz, 1H), 4.55-4.49 (m, 1H), 2.50-2.43 (m, 2H), 1.69-1.64 (m, 4H), 1.48 (m, 1H), 1.18-1.12 (m, 3H).

Example 4

Preparation of 3-N-cycloalkyl-5-[(phenyl or substituted phenyl)furan-2-yl]methylene-2-thioxoimidazolidin-4-ones or 3-N-cycloalkyl-5-[(Phenyl or Substituted Phenyl)thiophen-2-yl]methylene-2-thioxoimidazolidin-4-ones Preparation of 3-cycloalkyl-2-thioxoimidazolidin-4-ones (8): To a solution of glycine ethyl ester isothiocyanate (1 g, 6.9 mmol) in chloroform (25 mL) was added the cycloalkyl amine (7.0 mmol) in chloroform (25 mL) at room temperature. After 1 hour of stirring, the solution was brought to reflux for 30 minutes after which the solvent was removed in vacuo. The resulting residue was taken up in ethanol (25 mL) and 50% aqueous HCl (25 mL) was added. The solution was brought to reflux for 2 hours, and the solvent was then removed in vacuo. The crude 3-cycloalkyl-2-thioxoimidazolidin-4-ones were then recrystallized from ethanol.

Preparation of 2-thioxoimidazolidin-4-one analogs (9): To a solution of the 3-cycloalkyl-2-thioxoimidazolidin-4-one prepared above (0.5 mmol) in THF (2 mL) was added potassium tert-butoxide (0.6 mmol) at room temperature. The resulting yellow solution was stirred for 1 minute, after which time was added either a 5-aryl or 5-substituted aryl furan-2-yl carboxaldehyde, or a 5-aryl or 5-substituted aryl thiophene-2-yl carboxaldehyde (0.5 mmol) at room temperature as a solid at room temperature. The mixture was stirred for 6 hours. The reaction was then quenched by the addition of aqueous NH$_4$Cl and diluted with ethyl acetate (50 mL). The organic phase was washed with water (3×10 mL), and then dried over anhydrous Na$_2$SO$_4$. The solvent was removed in vacuo. The crude product was recrystallized from ethanol to afford the desired product.

The following are non-limiting examples of compounds prepared using Scheme IV and the procedures of Example 4.

(Z)-3-cyclohexyl-5-{[(4-methylphenyl)thiophen-2-yl]methylene}-2-thioxoimidazolidin-4-one (C1)

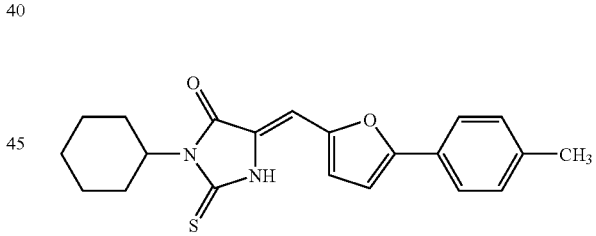

$^1$H-NMR (500 MHz, CDCl$_3$): δ 9.17 (br, 1H), 7.75-7.73 (m, 2H), 7.60-7.58 (m, 2H), 6.80-6.76 (m, 2H), 5.84 (m, 1H), 4.65-4.58 (m, 1H), 2.42 (s, 3H), 2.50-2.43 (m, 2H), 1.69-1.64 (m, 4H), 1.48 (m, 1H), 1.18-1.12 (m, 3H).

(Z)-3-cyclohexyl-5-{[(4-fluorophenyl)thiophen-2-yl]methylene}-2-thioxoimidazolidin-4-one (C2)

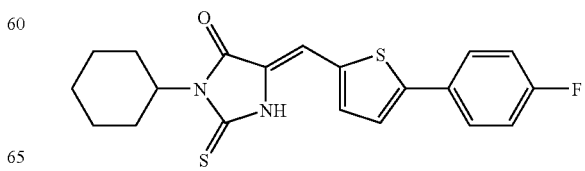

¹H-NMR (500 MHz, CDCl₃): δ 8.61 (br, 1H), 7.74 (s, 1H), 7.67-7.64 (m, 2H), 7.62-7.59 (m, 2H), 7.56-7.55 (m, 2H), 7.35-7.34 (m, 1H), 6.81 (s, 1H), 4.61-4.55 (m, 1H), 2.41-2.29 (m, 2H), 1.71-1.69 (m, 4H), 1.43 (m, 1H), 1.35-1.24 (m, 3H).

(Z)-3-cyclohexyl-5-{[(3-nitrophenyl)thiophen-2-yl]methylene}-2-thioxoimidazolidin-4-one (C3)

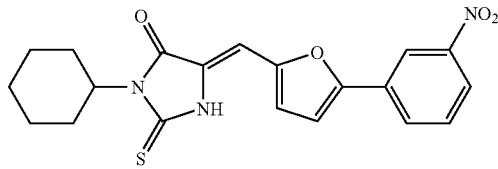 [SMILES: O=C1/C(=C/c2ccc(-c3cccc([N+](=O)[O-])c3)o2)NC(=S)N1C1CCCCC1]

¹H-NMR (500 MHz, C₆D₆): δ 8.24-8.23 (m, 1H), 7.76-7.74 (m, 2H), 7.68-7.66 (m, 2H), 7.43 (s, 1H), 6.77-6.74 (m, 1H), 5.34 (m, 1H), 2.70-2.68 (m, 2H), 1.75-1.73 (m, 4H), 1.54-1.23 (m, 4H).

(Z)-3-cyclohexyl-5-{[(2-fluoropyridin-3-yl)furan-2-yl]methylene}-2-thioxoimidazolidin-4-one (C4)

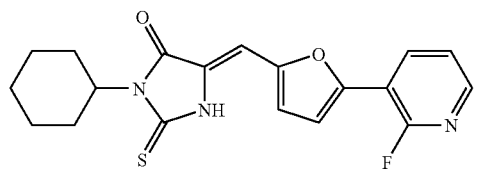 [SMILES: O=C1/C(=C/c2ccc(-c3cccnc3F)o2)NC(=S)N1C1CCCCC1]

¹H-NMR (500 MHz, CDCl₃): δ 9.14 (br, 1H), 8.23-8.17 (m, 1H), 8.13-8.11 (m, 1H), 7.37-7.33 (m, 2H), 7.06 (m, 1H), 6.82 (m, 1H), 4.60-4.56 (m, 1H), 2.35-2.28 (m, 2H), 1.89-1.69 (m, 5H), 1.42-1.26 (m, 3H).

(Z)-3-cyclohexyl-5-{[(3,4-difluorophenyl)thiophen-2-yl]methylene}-2-thioxoimidazolidin-4-one (C5)

¹H-NMR (500 MHz, CDCl₃): δ 9.06 (br, 1H), 7.65-7.41 (m, 5H), 6.80 (s, 1H), 4.60-4.56 (m, 1H), 2.35-2.28 (m, 2H), 1.89-1.69 (m, 5H), 1.42-1.26 (m, 3H).

(Z)-3-cyclohexyl-5-{[(4-fluorophenyl)thiophen-2-yl]methylene}-2-thioxoimidazolidin-4-one (C6)

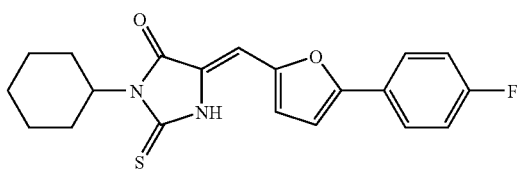

¹H-NMR (500 MHz, CDCl₃): δ 9.09 (br, 1H), 7.77-7.65 (m, 5H), 7.66 (m, 1H), 7.18-7.13 (m, 2H), 6.80-6.72 (m, 2H), 4.61-4.56 (m, 1H), 2.35-2.28 (m, 2H), 1.89-1.69 (m, 5H), 1.42-1.26 (m, 3H).

(Z)-3-cyclohexyl-5-{[(pyridin-3-yl)furan-2-yl]methylene}-2-thioxoimidazolidin-4-one (C7)

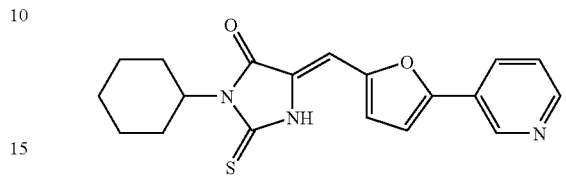

¹H-NMR (500 MHz, CDCl₃): δ 9.05 (br, 1H), 8.07-6.47 (m, 7H), 4.71 (m, 1H), 2.35-2.28 (m, 2H), 1.89-1.69 (m, 5H), 1.42-1.26 (m, 3H).

(Z)-3-cycloheptyl-5-{[(4-fluorophenyl)thiophen-2-yl]methylene}-2-thioxoimidazolidin-4-one (C8)

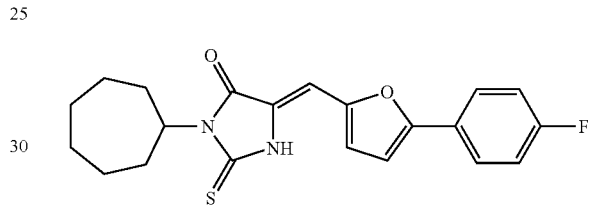

¹H-NMR (500 MHz, CDCl₃): δ 9.09 (br, 1H), 7.77-7.65 (m, 5H), 7.66 (m, 1H), 7.18-7.13 (m, 2H), 6.80-6.72 (m, 2H), 4.61-4.56 (m, 1H), 2.35-2.28 (m, 2H), 1.86-1.54 (m, 7H), 1.42-1.26 (m, 3H).

Example 5

Preparation of 3-N-cycloalkyl-5-[(phenyl or substituted phenyl)furan-2-yl]methyleneimidazolidine-2,4-diones or 3-N-cycloalkyl-5-[(Phenyl or Substituted Phenyl)thiophen-2-yl]methyleneimidazolidine-2,4-diones Preparation of 3-cycloalkyl-imidazolidine-2,4-diones (10): To a solution of glycine ethyl ester isocyanate (1 g, 7.6 mmol) in chloroform (25 mL) was added the cycloalkyl amine (7.7 mmol) in chloroform (25 mL) at room temperature. After 1 hour of stirring, the solution was brought to reflux for 30 minutes after which the solvent was removed in vacuo. The resulting residue was taken up in ethanol (25 mL) and 50% aqueous HCl (25 mL) was added. The solution was brought to reflux for 2 hours, and the solvent was removed in vacuo. The crude 3-cycloalkyl-imizadolidine-2,4-diones were recrystallized from ethanol.

Preparation of imizadolidine-2,4-dione analogs (9): To a solution of the 3-cycloalkyl-imizadolidine-2,4-dione prepared above (0.5 mmol) in THF (2 mL) was added potassium tert-butoxide (0.6 mmol) at room temperature. The resulting yellow solution was stirred for 1 minute, and then either a 5-aryl or 5-substituted aryl furan-2-yl carboxaldehyde, or a 5-aryl or 5-substituted aryl thiophene-2-yl carboxaldehyde (0.5 mmol) was added at room temperature. The resulting mixture was stirred for 6 hours. The reaction was then quenched by the addition of aqueous NH₄Cl, and the mixture was diluted with ethyl acetate (50 mL). The organic phase was washed with water (3×10 mL), and then dried over anhydrous Na$_2$SO$_4$. The solvent was removed in vacuo. The crude product was recrystallized from ethanol to afford the desired product.

The following are non-limiting examples of compounds prepared using Scheme V and the procedures of Example 5.

(Z)-3-cyclohexyl-5-{[5-(4-methylphenyl)furan-2-yl]methylene}imidazolidine-2,4-dione (E1)

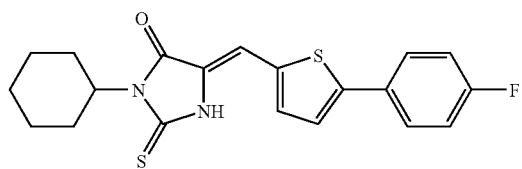

$^1$H-NMR (500 MHz, CDCl$_3$): δ 7.61-7.60 (m, 1H), 7.43 (br, 1H), 7.23-7.22 (m, 1H), 7.16-7.12 (m, 2H), 6.88 (s, 1H), 4.09-4.02 (m, 1H), 2.25-2.17 (m, 2H), 1.90-1.26 (m, 8H).

(Z)-3-cyclohexyl-5-{[5-(4-fluorophenyl)furan-2-yl]methylene}imidazolidine-2,4-dione (E2)

$^1$H-NMR (500 MHz, CDCl$_3$): δ 7.79 (s, 1H), 7.67-7.64 (m, 2H), 7.22-7.15 (m, 2H), 6.73-6.68 (m, 2H), 6.51 (s, 1H), 4.08-4.03 (m, 1H), 2.26-2.17 (m, 2H), 1.90-1.25 (m, 8H).

(Z)-3-cyclohexyl-5-{[5-(3-nitrophenyl)furan-2-yl]methylene}imidazolidine-2,4-dione (E3)

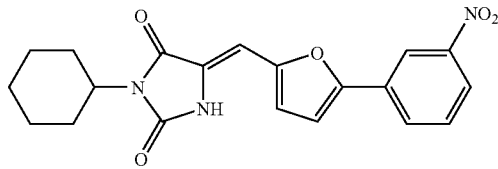

$^1$H-NMR (500 MHz, CDCl$_3$): δ 8.55-6.44 (m, 7H), 4.09-4.03 (m, 1H), 2.26-2.18 (m, 2H), 1.91-1.25 (m, 8H).

(Z)-3-cyclohexyl-5-{[(2-fluoropyridin-3-yl)furan-2-yl]methylene}imidazolidine-2,4-dione (E4)

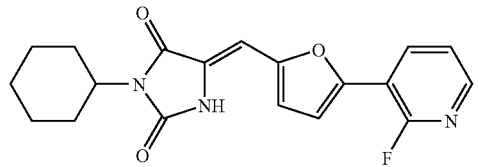

$^1$H-NMR (500 MHz, CDCl$_3$): δ 8.45-8.26 (m, 2H), 7.14-7.05 (m, 2H), 6.77 (m, 1H), 6.53 (m, 1H), 4.09-4.04 (m, 1H), 2.26-2.18 (m, 2H), 1.91-1.25 (m, 8H).

(Z)-3-cyclohexyl-5-{[5-(4-methylphenyl)furan-2-yl]methylene}imidazolidine-2,4-dione (E5)

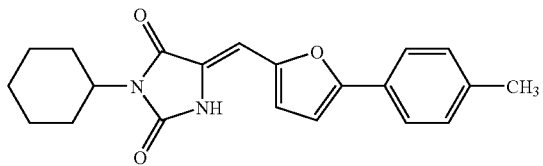

$^1$H-NMR (500 MHz, CDCl$_3$): δ 7.82 (br, 1H), 7.58-7.56 (m, 2H), 7.29-7.27 (m, 1H), 6.73-6.72 (m, 1H), 6.69-6.68 (m, 1H), 6.51 (s, 1H), 4.08-4.03 (m, 1H), 2.43 (s, 3H), 2.23-2.18 (m, 2H), 1.90-1.26 (m, 8H).

(Z)-3-cyclohexyl-5-[(5-phenylfuran-2-yl)methylene]-imidazolidine-2,4-dione (E6)

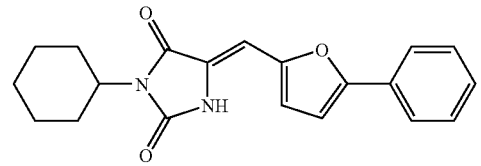

$^1$H-NMR (500 MHz, CDCl$_3$): δ 7.89 (br, 1H), 7.74-7.64 (m, 2H), 7.49-7.42 (m, 2H), 7.39-7.36 (m, 1H), 6.79-6.78 (m, 1H), 6.70-6.69 (m, 1H), 6.51 (s, 1H), 4.09-4.02 (m, 1H), 2.25-2.18 (m, 2H), 1.90-1.25 (m, 8H).

(Z)-3-cyclohexyl-5-{[5-(3,4-difluorophenyl)furan-2-yl]methylene}imidazolidine-2,4-dione (E7)

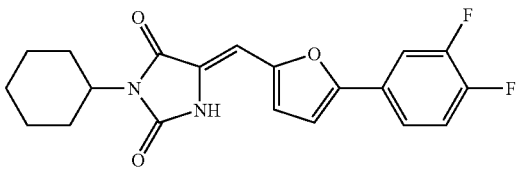 [SMILES: O=C1/C(=C/c2ccc(-c3ccc(F)c(F)c3)o2)NC(=S)N1C1CCCCC1]

$^1$H-NMR (500 MHz, CDCl$_3$): δ 8.55-6.44 (m, 7H), 4.09-4.03 (m, 1H), 2.26-2.18 (m, 2H), 1.91-1.25 (m, 8H).

(Z)-3-cycloheptyl-5-[(5-phenylfuran-2-yl)methylene]-imidazolidine-2,4-dione (E8)

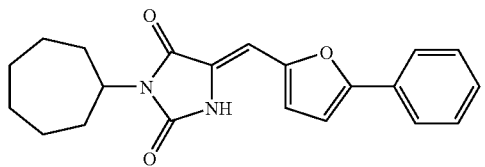 [SMILES: O=C1N/C(=C\c2ccc(-c3ccccc3)o2)C(=O)N1C1CCCCCC1]

$^1$H-NMR (500 MHz, CDCl$_3$): δ 7.89 (br, 1H), 7.74-7.64 (m, 2H), 7.49-7.42 (m, 2H), 7.39-7.36 (m, 1H), 6.79-6.78 (m, 1H), 6.70-6.69 (m, 1H), 6.51 (s, 1H), 4.23-4.18 (m, 1H), 2.30-2.19 (m, 2H), 1.86-1.28 (m, 10H).

(Z)-3-cycloheptyl-5-{[5-(4-fluorophenyl)thiophen-2-yl]methylene}imidazolidine-2,4-dione (E9)

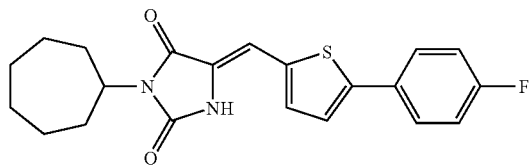 [SMILES: O=C1N/C(=C\c2ccc(-c3ccc(F)cc3)s2)C(=O)N1C1CCCCCC1]

$^1$H-NMR (500 MHz, CDCl$_3$): δ 7.76-7.02 (m, 7H), 4.09-4.02 (m, 1H), 2.27-2.18 (m, 2H), 1.79-1.28 (m, 10H).

(Z)-3-cycloheptyl-5-{[(3-nitrophenyl)furan-2-yl]methylene}imidazolidine-2,4-dione (E10)

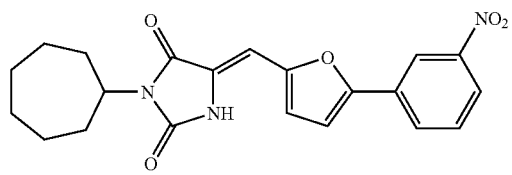 [SMILES: O=C1N/C(=C\c2ccc(-c3cccc([N+](=O)[O-])c3)o2)C(=O)N1C1CCCCCC1]

$^1$H-NMR (500 MHz, CDCl$_3$): δ 8.65-7.03 (m, 7H), 4.09-4.03 (m, 1H), 2.29-2.17 (m, 2H), 1.85-1.16 (m, 10H).

(Z)-3-cycloheptyl-5-{[(4-methylphenyl)furan-2-yl]methylene}imidazolidine-2,4-dione (E11)

$^1$H-NMR (500 MHz, CDCl$_3$): δ 7.82 (br, 1H), 7.58-7.56 (m, 2H), 7.29-7.27 (m, 1H), 6.73-6.72 (m, 1H), 6.69-6.68 (m, 1H), 6.51 (s, 1H), 4.23-4.18 (m, 1H), 2.42 (s, 3H), 2.30-2.29 (m, 2H), 1.86-1.26 (m, 10H).

(Z)-3-cycloheptyl-5-{[(2-fluoropyridin-3-yl)furan-2-yl]methylene}imidazolidine-2,4-dione (E12)

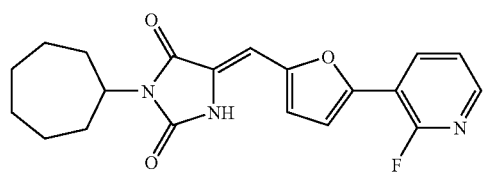 [SMILES: O=C1N/C(=C\c2ccc(-c3cccnc3F)o2)C(=O)N1C1CCCCCC1]

$^1$H-NMR (500 MHz, CDCl$_3$): δ 8.44-8.16 (m, 2H), 7.14-7.05 (m, 2H), 6.77 (m, 1H), 6.53 (m, 1H), 4.07-4.04 (m, 1H), 2.26-2.18 (m, 2H), 1.91-1.25 (m, 10H).

(Z)-3-cycloheptyl-5-{[(3,4-difluorophenyl)furan-2-yl]methylene}imidazolidine-2,4-dione (E13)

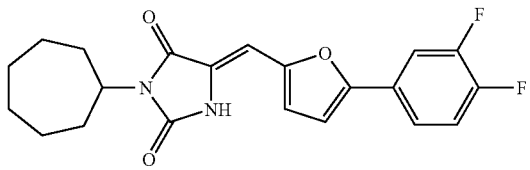

$^1$H-NMR (500 MHz, CDCl$_3$): δ 7.89 (br, 1H), 7.49-7.36 (m, 5H), 6.73 (s, 1H), 4.69-4.64 (m, 1H), 2.29-2.20 (m, 2H), 1.89-1.26 (m, 10H).

(Z)-3-cycloheptyl-5-{[5-(2-fluoropyridin-3-yl)furan-2-yl]methylene}-2-thioxothiazolidin-4-one (E14)

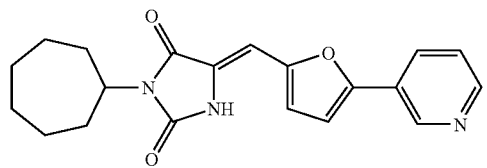 [SMILES: O=C1N/C(=C\c2ccc(-c3cccnc3)o2)C(=O)N1C1CCCCCC1]

$^1$H-NMR (500 MHz, CDCl$_3$): δ 9.03 (br, 1H), 8.13-6.41 (m, 7H), 4.72 (m, 1H), 2.27-2.25 (m, 2H), 1.89-1.26 (m, 10H).

Example 6

Method of Treating or Preventing a Viral Infection

The compounds described herein can be used to treat or prevent a viral infection. For example, the compounds can be used to inoculate a species against viral attack or as treatment after infection. This can be demonstrated as follows: (Z)-3-Cyclohexyl-5-{[5-(4-fluorophenyl)furan-2-yl]-methylene}-2-thioxothiazolidin-4-one (compound A1), or (Z)-3-cyclooctyl-5-{[(4-methylphenyl)furan-2-yl]methylene}-2-thioxothiazolidin-4-one (compound A17), was dissolved in dimethyl sulfoxide (DMSO) and diluted with growth medium to form an inhibitor solution. The inhibitor solution was added to a virus inoculum (e.g., A/Udorn/72, H$_3$N$_2$) and to a cell growth medium wherein the final concentration of A1 or A17 is 50 nM. The virus inoculum was incubated with A1 or A17 for one hour at 37° C. prior to inoculation of an MDCK cell monolayer, or added to the cell culture at a designated time point. FIG. 1 depicts the viral yield changes observed. The sample incubated with A1 or A17 for one hour prior to inoculation shows at least a 3 log difference in virus concentration versus the untreated MDCK cells. Further, the cell cultures treated with A1 and A17 after inoculation show decreased virus yield.

Figure 2:
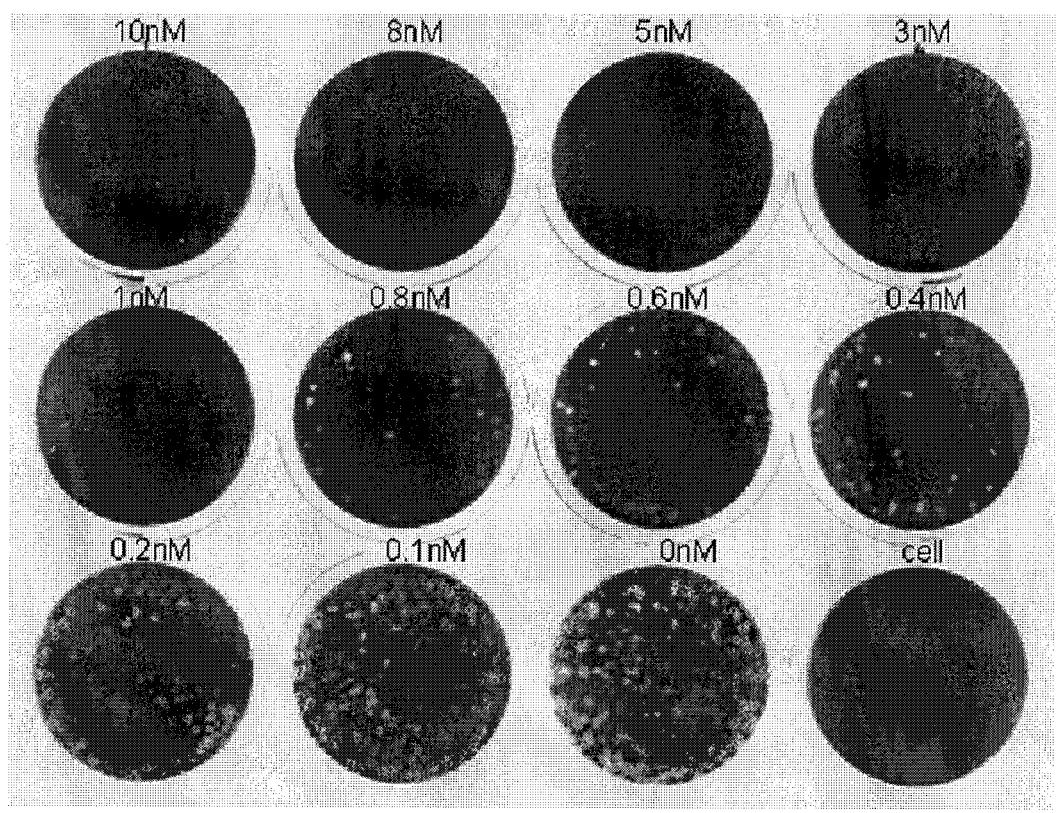
FIG. 2 is a photograph of plates that were inoculated with A/Udorn/72, H3N2 virus inoculums (250 pfu) and treated with varying amounts of inhibitor A1.

To determine effective concentrations of the compounds described herein, EC$_{50}$ values for the compounds described herein were obtained by the following procedure. Various concentrations of compounds in DMSO were pre-incubated with 100-250 pfu of the virus inoculum (e.g. A/Udorn/72, H$_3$N$_2$). FIG. 2 provides a photograph of the test plates of the A1 compound at various concentrations in the plaque assay. From this assay, the EC$_{50}$ value of compound A1 was determined to be less than or equal to about 0.4 nanomolar (<0.4 nM). The EC$_{50}$ values of compound A1 for other influenza virus strains were determined by the same method (data shown in Table I below). The EC$_{50}$ values of some other compounds for various influenza virus strains were determined by the same method (data shown in Table G below).

Example 7

Methods of Inhibiting Fusion by Destabilization of Surface Fusion Proteins

Figure 3:
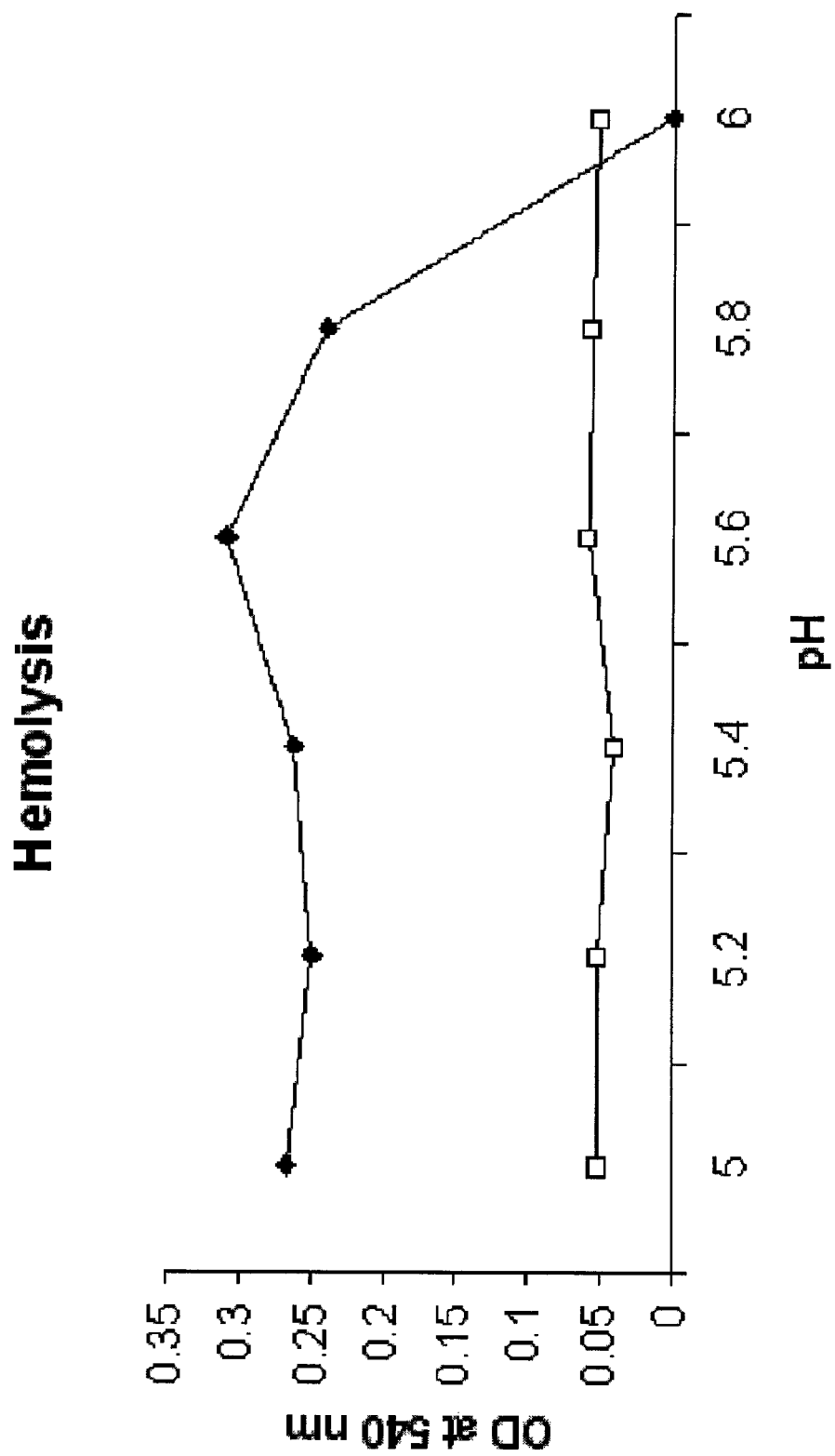
FIG. 3 depicts the results of inhibitor A1 on the growth of virus A/Udorn/72 at various pH values.

The compounds described herein can be used to inhibit fusion mediated by the surface fusion protein on the virion. This can be demonstrated as follows. (Z)-3-Cyclohexyl-5-{[5-(4-fluorophenyl)furan-2-yl]-methylene}-2-thioxothiazolidin-4-one (compound A1) was dissolved in polyethylene glycol having an average molecular weight of about 400 (PEG400). The A1 solution was incubated with influenza virus (A/Udorn/72, $H_3N_2$) wherein the final concentration of A1 is 10 μM. The A1 bound virus was incubated with human red blood cells and membrane fusion was induced by reducing the pH of the mixture. FIG. 3 shows the inhibitory effects of A1 on membrane fusion at various pH values.

Figure 4:
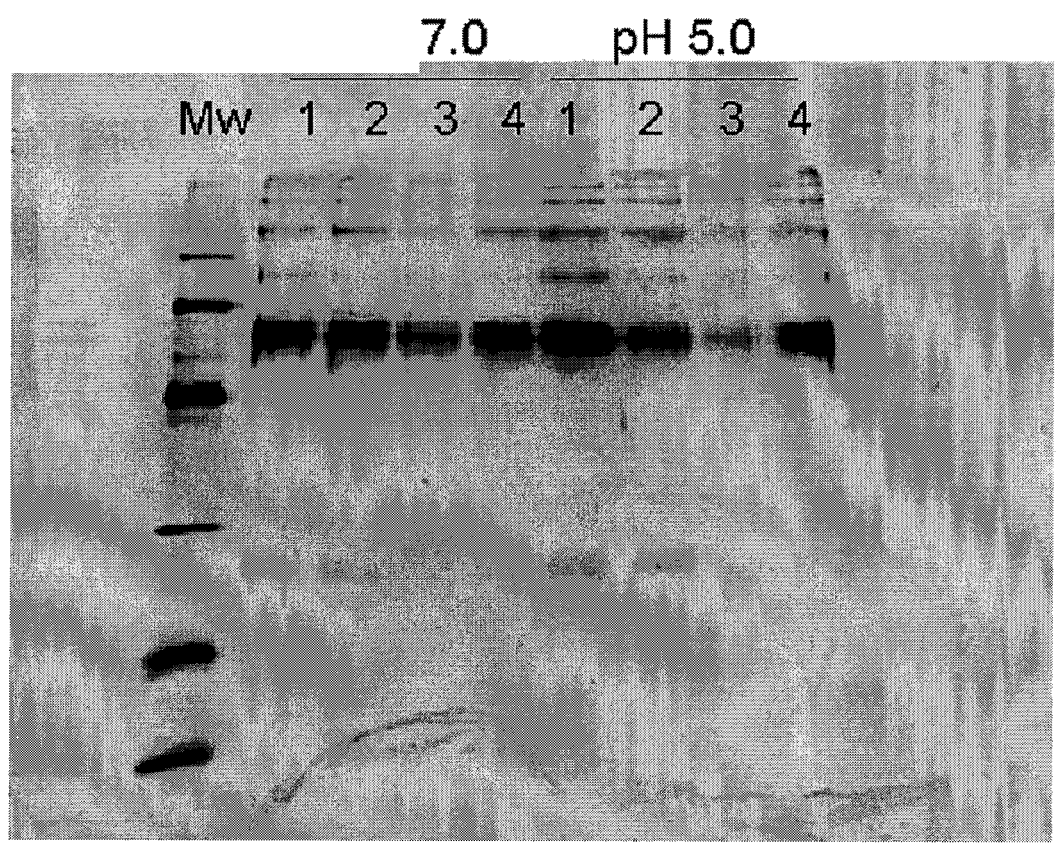
FIG. 4 shows the destabilization effects of A1 on HA at pH 7.0 and pH 5.0.

The compounds described herein also can be used to destablilize the surface fusion protein on the virion. This can be demonstrated as follows. (Z)-3-Cyclohexyl-5-{[5-(4-fluorophenyl)furan-2-yl]-methylene}-2-thioxothiazolidin-4-one (compound A1) was dissolved in polyethylene glycol having an average molecular weight of about 400 (PEG400). The A1 solution was incubated with recombinant influenza virus hemagglutinin (A/Wyoming/3/03), wherein the final concentration of A1 was 5 μM. The A1 treated HA was incubated with protease trypsin, wherein the final concentration of trypsin was 2 ng/μL. FIG. 4 shows the destabilization effects of A1 on HA at pH 7.0 and pH 5.0.

Example 8

Proteolytic Sensitivity Assay

The compounds described herein are capable of binding to hemagglutinin and thereby destabilizing the fusion protein. The following procedure can be used to determine the increase in destabilization and therefore the increased sensitivity of hemagglutinin to proteolytic attack caused by the compounds described herein. At the fusion conformation, HA becomes more sensitive to protease digestion. This property can be used to verify if a fusion inhibitor interacts with HA (Luo G. et al. "Molecular mechanism underlying the action of a novel fusion inhibitor of influenza A virus." *J Virol* (1997); 71(5):4062-70).

A purified trimer of hemagglutinin ectodomain can be incubated with the compound to be tested at a concentration of 5 μM. The trimers are subjected to trypsin digestion at pH 7.0 and pH 5.0 with controls of untreated HA and HA treated with DMSO, which is the solvent used to dissolve the test compound. For the pH 5.0 sample, the HA trimers are treated with a pH 5.0 buffer for 15 minutes and neutralized to pH 7.0. Trypsin (20 ng) is added to the sample in 10 μL and the digestion is allowed to proceed for 1 hour at 37° C. The amount of HA present is assessed by a Western Blot gel electrophoresis using anti-HA (H3) antisera. Samples containing effective inhibitors will provide an increase in digestion of HA by trypsin.

Example 9

Plaque Assays in MDCK Cells

The following assay can be used to screen compounds for antiviral activity. Madin-Darby canine kidney (MDCK) cells can be cultured to monolayers in 6-well plates. 120 PFU of A/Udorn/72 ($H_3N_2$) virus can be added to each well. Designated dosages of inhibitor compounds can be added with the virus inoculum (0 hour) for determination of antiviral activities. Corresponding amounts of DMSO used to dissolve the compound can be added in a separate well as the negative control.

The virus yield, at given time points, in the presence and absence of inhibitor compounds can be determined in a plaque assay using MDCK cells and A/Udorn/72 ($H_3N_2$) virus following the protocol in Kati et al. (Kati, M. et al. "In Vitro Characterizaion of A-315675, a Highly Potent Inhibitor of A and B Strain Influenza Virus Neuramididases and Influenza Virus Replication" *Antimicrobial Agents and Chemotherapy*, April (2002) p. 1014-1021). For example, MDCK cells were maintained in DMEM supplemented with 10% fetal calf serum, 20 mM HEPES buffer, and antibiotics. Cells were cultured in a flask at 37° C. and 5% $CO_2$. When monolayers of MDCK cells become 95% confluent in 6-well trays, the influenza virus inoculum in 0.1 mL DMEM was added to each well. After 1.0 hour absorption in 37° C., infected cells were washed with warm PBS once and the wells were overlaid with 0.6% agarose in DMEM supplemented with trypsin. After 48 hours of infection, the agar overlay was removed and the monolayers stained with 0.1% crystal violet in 10% formaldehyde. The antiviral efficacy of the test compounds against the clinical isolates was assessed by counting the number of the plaques at each drug concentration. The 50% effective concentration of the drug, i.e., that which reduced plaque number by 50% ($EC_{50}$), was determined with visional inspection.

Tables A-I below provide results of the above plaque assay for various compounds described herein at various concentrations.

TABLE A

| No. | Compound | 10 nM | 1 nM |
|---|---|---|---|
| A1 | 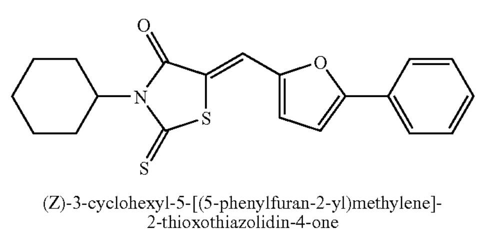 [SMILES: O=C1/C(=C/c2ccc(-c3ccccc3)o2)SC(=S)N1C1CCCCC1]  (Z)-3-cyclohexyl-5-[(5-phenylfuran-2-yl)methylene]-2-thioxothiazolidin-4-one | 0%* | 1%* |

TABLE A-continued

| No. | Compound | 10 nM | 1 nM |
|---|---|---|---|
| A2 | 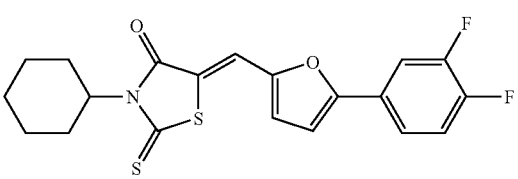<br>(Z)-3-cyclohexyl-5-{[(3,4-difluorophenyl)furan-2-yl]methylene}-2-thioxothiazolidin-4-one | 1% | 3% |
| A3 | 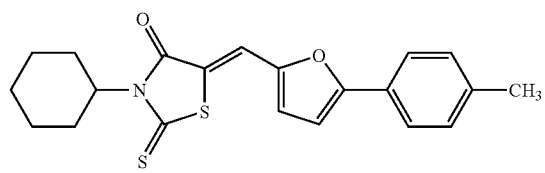<br>(Z)-3-cyclohexyl-5-{[(4-methylphenyl)furan-2-yl]methylene}-2-thioxothiazolidin-4-one | 0% | 5% |
| A4 | <br>(Z)-3-cyclohexyl-5-{[(4-methoxyphenyl)furan-2-yl]methylene}-2-thioxothiazolidin-4-one | 0% | 12% |
| A5 | 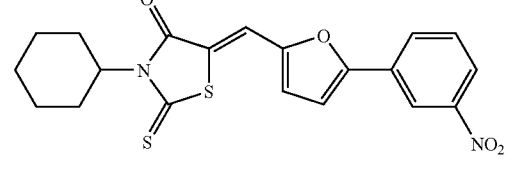<br>(Z)-3-cyclohexyl-5-{[(3-nitrophenyl)furan-2-yl]methylene}-2-thioxothiazolidin-4-one | 0% | 21% |
| A6 | 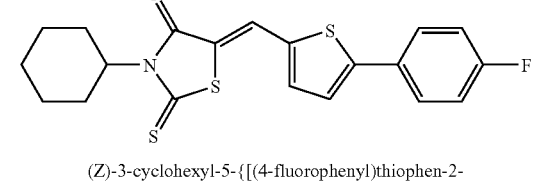<br>(Z)-3-cyclohexyl-5-{[(4-fluorophenyl)thiophen-2-yl]methylene}-2-thioxothiazolidin-4-one | 0% | 33% |
| A7 | 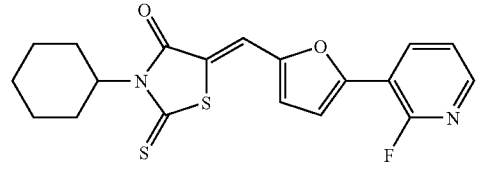<br>(Z)-3-cyclohexyl-5-{[5-(2-fluoropyridin-3-yl)furan-2-yl]methylene}-2-thioxothiazolidin-4-one | 0% | 4% |

TABLE A-continued

| No. | Compound | 10 nM | 1 nM |
|---|---|---|---|
| A8 | (Z)-3-cycloheptyl-5-[(5-phenylfuran-2-yl)methylene]-2-thioxothiazolidin-4-one | 0% | 1% |
| A9 | (Z)-3-cycloheptyl-5-{[(3,4-difluorophenyl)furan-2-yl]methylene}-2-thioxothiazolidin-4-one | 0% | 0% |
| A10 | (Z)-3-cycloheptyl-5-{[(4-methylphenyl)furan-2-yl]methylene}-2-thioxothiazolidin-4-one | 0% | 1% |
| A11 | (Z)-3-cycloheptyl-5-{[(4-fluorophenyl)furan-2-yl]methylene}-2-thioxothiazolidin-4-one | 0% | 1% |
| A12 | (Z)-3-cycloheptyl-5-{[(3-nitrophenyl)furan-2-yl]methylene}-2-thioxothiazolidin-4-one | 0% | 2% |
| A13 | (Z)-3-cycloheptyl-5-{[(4-fluorophenyl)thiophen-2-yl]methylene}-2-thioxothiazolidin-4-one | 0% | 19% |

TABLE A-continued

| No. | Compound | 10 nM | 1 nM |
|---|---|---|---|
| A14 | 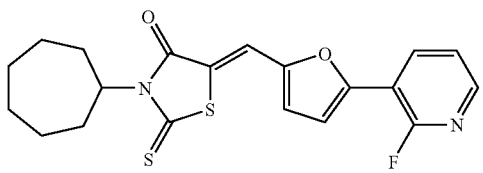<br>(Z)-3-cycloheptyl-5-{[(5-(2-fluoropyridin-3-yl)furan-2-yl]methylene}-2-thioxothiazolidin-4-one | 0% | 0% |
| A15 | 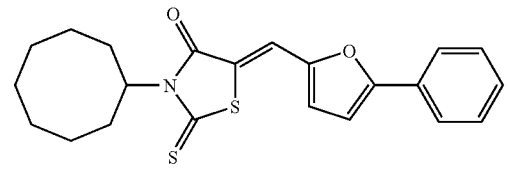<br>(Z)-3-cyclooctyl-5-[(5-phenylfuran-2-yl)methylene]-2-thioxothiazolidin-4-one | 0% | 1% |
| A16 | 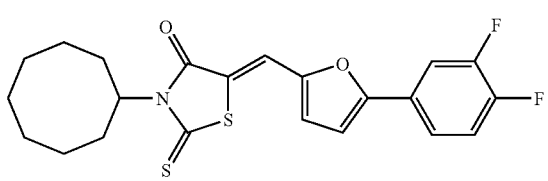<br>(Z)-3-cyclooctyl-5-{[(3,4-difluorophenyl)furan-2-yl]methylene}-2-thioxothiazolidin-4-one | 0% | 1% |
| A17 | 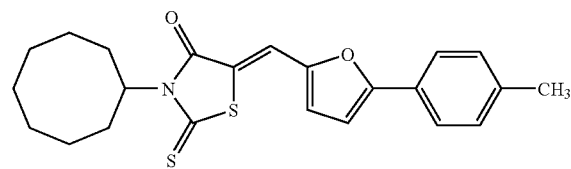<br>(Z)-3-cyclooctyl-5-{[(4-methylphenyl)furan-2-yl]methylene}-2-thioxothiazolidin-4-one | 0% | 1% |
| A18 | 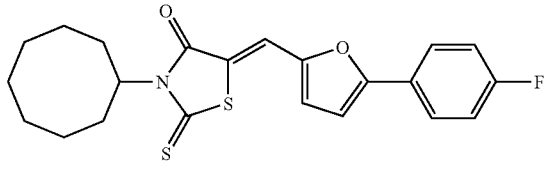<br>(Z)-3-cyclooctyl-5-{[(4-fluorophenyl)furan-2-yl]methylene}-2-thioxothiazolidin-4-one | 1% | 3% |
| A19 | 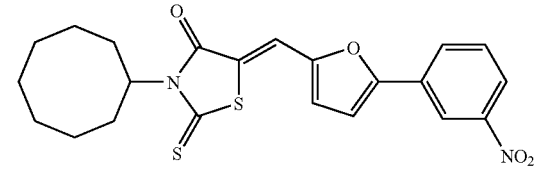<br>(Z)-3-cyclooctyl-5-{[(3-nitrophenyl)furan-2-yl]methylene}-2-thioxothiazolidin-4-one | 0% | 3% |

| No. | Compound | 10 nM | 1 nM |
|---|---|---|---|
| A20 | (Z)-3-cyclooctyl-5-{[(4-methoxyphenyl)furan-2-yl]methylene}-2-thioxothiazolidin-4-one | 0% | 0% |
| A21 | (Z)-3-cyclooctyl-5-{[(4-fluorophenyl)thiophen-2-yl]methylene}-2-thioxothiazolidin-4-one | 0% | 7% |
| A22 | (Z)-3-cyclooctyl-5-{[5-(2-fluoropyridin-3-yl)furan-2-yl]methylene}-2-thioxothiazolidin-4-one | 0% | 0% |
| A23 | (Z)-3-cyclododecyl-5-[(5-phenylfuran-2-yl]methylene]-2-thioxothiazolidin-4-one | 0% | 2% |
| A24 | (Z)-3-cyclododecyl-5-{[(3,4-difluorophenyl)furan-2-yl]methylene}-2-thioxothiazolidin-4-one | 0% | 7% |
| A25 | (Z)-3-cyclododecyl-5-{[(4-methylphenyl)furan-2-yl]methylene}-2-thioxothiazolidin-4-one | 0% | 35% |

TABLE A-continued

| No. | Compound | 10 nM | 1 nM |
|---|---|---|---|
| A26 | (Z)-3-cyclododecyl-5-{[(4-fluorophenyl)thiophen-2-yl]methylene}-2-thioxothiazolidin-4-one | 3% | 42% |
| A27 | (Z)-3-cyclododecyl-5-{[(3-nitrophenyl)furan-2-yl]methylene}-2-thioxothiazolidin-4-one | 0% | 37% |
| A28 | (Z)-3-cyclododecyl-5-{[5-(2-fluoropyridin-3-yl)furan-2-yl]methylene}-2-thioxothiazolidin-4-one | 0% | 0% |
| A29 | (Z)-3-cyclododecyl-5-{[(4-fluorophenyl)thiophen-2-yl]methylene}-2-thioxothiazolidin-4-one | 3% | 75% |
| A30 | (Z)-3-(bicyclo[2.2.1]heptan-2-yl)-2-thioxo-5-((5-p-tolylfuran-2-yl)methylene)-thiazolidin-4-one | 0% | 1% |
| A31 | (Z)-3-(bicyclo[2.2.1]heptan-2-yl)-5-((5-(4-methoxyphenyl)furan-2-yl)methylene)-2-thioxothiazolidin-4-one | 0% | 0% |

TABLE A-continued

| No. | Compound | 10 nM | 1 nM |
|---|---|---|---|
| A32 | 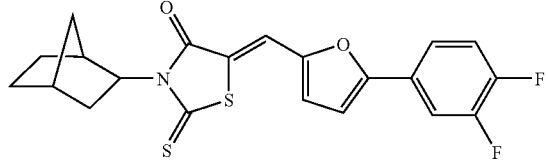 (Z)-3-(bicyclo[2.2.1]heptan-2-yl)-5-((5-(3,4-difluorophenyl)furan-2-yl)methylene)-2-thioxothiazolidin-4-one | 0% | 0% |
| A33 | 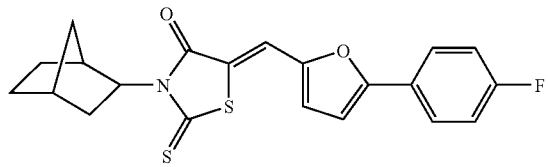 (Z)-3-(bicyclo[2.2.1]heptan-2-yl)-5-((5-(4-fluorophenyl)furan-2-yl)methylene)-2-thioxothiazolidin-4-one | 0% | 2% |
| A34 | 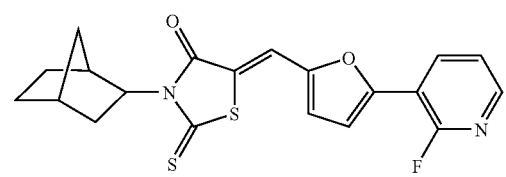 (Z)-3-(bicyclo[2.2.1]heptan-2-yl)-5-((5-(2-fluoropyridin-3-yl)furan-2-yl)methylene)-2-thioxothiazolidin-4-one | 0% | 0% |
| A35 | 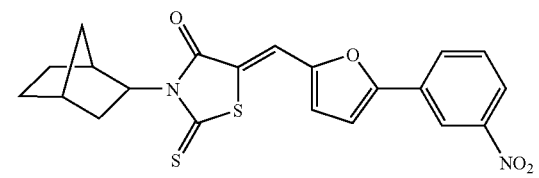 (Z)-3-(bicyclo[2.2.1]heptan-2-yl)-5-((5-(3-nitrophenyl)furan-2-yl)methylene)-2-thioxothiazolidin-4-one | 0% | 0% |
| A36 | 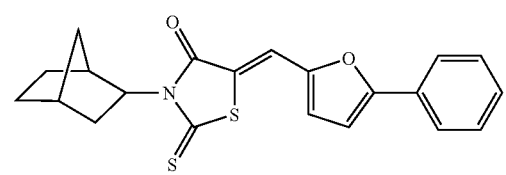 (Z)-3-(bicyclo[2.2.1]heptan-2-yl)-5-((5-(3-nitrophenyl)furan-2-yl)methylene)-2-ioxothiazolidin-4-one | 0% | 1% |
| A37 | 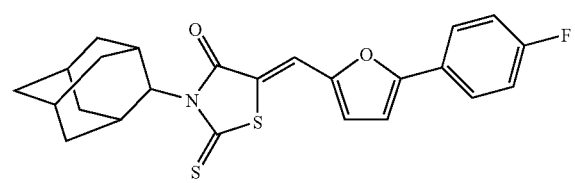 (Z)-3-adamantyl-5-{[(4-fluorophenyl)furan-2-yl]methylene}-2-thioxothiazolidin-4-one | 0% | 0% |

TABLE A-continued

| No. | Compound | 10 nM | 1 nM |
|---|---|---|---|
| A38 | (Z)-3-adamantyl-5-((5-(2-fluoropyridin-3-yl)furan-2-yl)methylene)-2-thioxothiazolidin-4-one | 0% | 0% |
| A39 | (Z)-3-adamantyl-5-[(5-phenylfuran-2-yl)methylene]-2-thioxothiazolidin-4-one | 0% | 0% |
| A40 | (Z)-3-adamantyl-5-{[(4-methoxyphenyl)furan-2-yl]methylene}-2-thioxothiazolidin-4-one | 0% | 0% |
| A41 | (Z)-3-adamantyl-5-{[(3,4-difluorophenyl)furan-2-yl]methylene}-2-thioxothiazolidin-4-one | 0% | 0% |
| A42 | (Z)-3-adamantyl-5-{[(3-nitrophenyl)furan-2-yl]methylene}-2-thioxothiazolidin-4-one | 0% | 0% |
| A43 | (Z)-3-cyclooctyl-5-{[5-(pyridin-3-yl)furan-2-yl]methylene}-2-thioxothiazolidin-4-one | 0% | 0% |

TABLE A-continued

| No. | Compound | 10 nM | 1 nM |
|---|---|---|---|
| A44 | (Z)-3-cyclopentyl-5-{[5-(2-fluoropyridin-3-yl)furan-2-yl]methylene}-2-thioxothiazolidin-4-one | 0% | 1% |
| A45 | (Z)-3-cyclopentyl-5-{[(3,4-difluorophenyl)furan-2-yl]methylene}-2-thioxothiazolidin-4-one | 0% | 2% |
| A46 | (Z)-3-cyclopentyl-5-{[(4-methylphenyl)furan-2-yl]methylene}-2-thioxothiazolidin-4-one | 0% | 4% |
| A47 | (Z)-3-cyclopentyl-5-{[(4-methoxyphenyl)furan-2-yl]methylene}-2-thioxothiazolidin-4-one | 0% | 4% |
| A48 | (Z)-3-cyclopentyl-5-{[(4-fluorophenyl)furan-2-yl]methylene}-2-thioxothiazolidin-4-one | 0% | 4% |
| A49 | (Z)-3-cyclopentyl-5-[(phenylfuran-2-yl)methylene-2-thioxothiazolidin-4-one | 0% | 5% |

TABLE A-continued

| No. | Compound | 10 nM | 1 nM |
|---|---|---|---|
| A50 | (Z)-3-cyclopentyl-5-{[(3-nitrophenyl)furan-2-yl]methylene}-2-thioxothiazolidin-4-one | 0% | 12% |
| A51 | (Z)-3-(bicyclo[2.2.1]heptan-2-yl)-5-{[5-(pyridin-3-yl)furan-2-yl]methylene}-2-thioxothiazolidin-4-one | 0% | 12% |
| A52 | (Z)-3-cyclooctyl-5-{[5-(pyridin-3-yl)furan-2-yl]methylene}-2-thioxothiazolidin-4-one | 0% | 20% |
| A53 | (Z)-3-cycloheptyl-5-{[5-(pyridin-3-yl)furan-2-yl]methylene}-2-thioxothiazolidin-4-one | 0% | 20% |
| A54 | (Z)-3-cyclohexyl-5-{[5-(pyridin-3-yl)furan-2-yl]methylene}-2-thioxothiazolidin-4-one | 0% | 28% |
| A55 | (Z)-3-cyclopentyl-5-{[(4-fluorophenyl)thiophen-2-yl]methylene}-2-thioxothiazolidin-4-one | 1% | 38% |

TABLE A-continued

| No. | Compound | 10 nM | 1 nM |
|---|---|---|---|
| A56 | 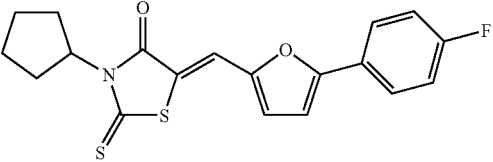<br>(Z)-3-cyclopentyl-5-{[(4-fluorophenyl)furan-2-yl]methylene}-2-thioxothiazolidin-4-one | 1% | 60% |

TABLE B

| No. | Compound | 1 μM |
|---|---|---|
| B1 | 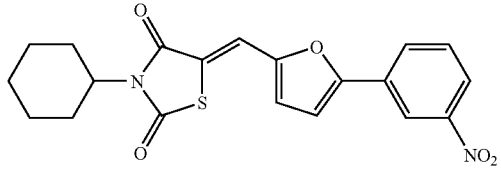<br>(Z)-3-cyclohexyl-5-{[(3-nitrophenyl)furan-2-yl]methylene}thiazolidine-2,4-dione | 0%* |
| B2 | 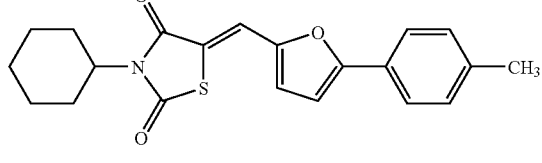<br>(Z)-3-cyclohexyl-5-{[(4-methylphenyl)furan-2-yl]methylene}thiazolidine-2,4-dione | 1% |
| B3 | 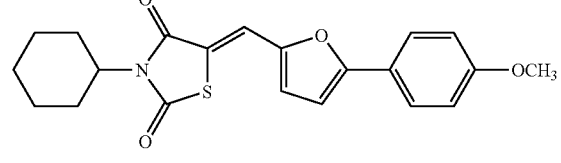<br>(Z)-3-cyclohexyl-5-{[(4-methoxyphenyl)furan-2-yl]methylene}thiazolidine-2,4-dione | 1% |
| B4 | 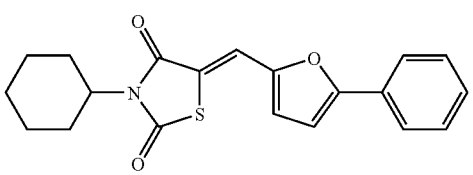<br>(Z)-3-cyclohexyl-5-[(5-phenylfuran-2-yl)methylene]thiazolidine-2,4-dione | 2% |
| B5 | 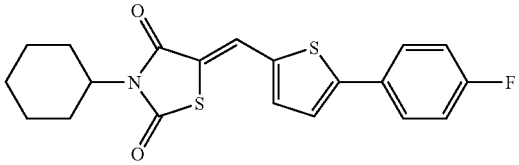<br>(Z)-3-cyclohexyl-5-{[(4-fluorophenyl)thien-2-yl]methylene}thiazolidine-2,4-dione | 3% |

TABLE B-continued

| No. | Compound | 1 μM |
|---|---|---|
| B6 | (Z)-3-cyclohexyl-5-{[(3,4-difluorophenyl)furan-2-yl]methylene}thiazolidine-2,4-dione | 8% |
| B7 | (Z)-3-cyclohexyl-5-{[(4-fluorophenyl)furan-2-yl]methylene}thiazolidine-2,4-dione | 14% |

TABLE C

| No. | Compound | 1 μM | 100 nM |
|---|---|---|---|
| C1 | (Z)-3-cyclohexyl-5-{[(4-methylphenyl)thiophen-2-yl]methylene}-2-thioxoimidazolidin-4-one | 0%* | 0%* |
| C2 | (Z)-3-cyclohexyl-5-{[(4-fluorophenyl)thiophen-2-yl]methylene}-2-thioxoimidazolidin-4-one | 0% | 0% |
| C3 | (Z)-3-cyclohexyl-5-{[(3-nitrophenyl)thiophen-2-yl]methylene}-2-thioxoimidazolidin-4-one | 1% | 0% |
| C4 | (Z)-3-cyclohexyl-5-{[(2-fluoropyridin-3-yl)furan-2-yl]methylene}-2-thioxoimidazolidin-4-one | 0% | 0% |

TABLE C-continued

| No. | Compound | 1 μM | 100 nM |
|---|---|---|---|
| C5 | (Z)-3-cyclohexyl-5-{[(3,4-difluorophenyl)thiophen-2-yl]methylene}-2-thioxoimidazolidin-4-one | 0% | 0% |
| C6 | (Z)-3-cyclohexyl-5-{[(4-fluorophenyl)thiophen-2-yl]methylene}-2-thioxoimidazolidin-4-one | 0% | 1% |
| C7 | Z)-3-cyclohexyl-5-{[(pyridin-3-yl)furan-2-yl]methylene}-2-thioxoimidazolidin-4-one | 0% | 16% |
| C8 | (Z)-3-cycloheptyl-5-{[(4-fluorophenyl)thiophen-2-yl]methylene}-2-thioxoimidazolidin-4-one | 35% | — |

TABLE D

| No. | Compound | 1000 nM | 100 nM | 10 nM | 1 nM |
|---|---|---|---|---|---|
| D1 | (Z)-3-cyclooctyl-5-[(3'-fluorobiphenyl-3-yl)methylene]-2-thioxoimidazolidin-4-one | 0 | 34 | 51 | 57 |
| D2 | (Z)-3-cyclohexyl-5-[(4'-fluorobiphenyl-4-yl)methylene]-2-thioxoimidazolidin-4-one | 3 | 37 | 71 | 100 |

TABLE D-continued

| No. | Compound | 1000 nM | 100 nM | 10 nM | 1 nM |
|---|---|---|---|---|---|
| D3 | (Z)-3-cyclohexyl-5-[(3'-fluorobiphenyl-3-yl)methylene]-2-thioxoimidazolidin-4-one | 6 | 86 | 86 | 89 |

TABLE E

| No. | Compound | 1 μM | 100 nM |
|---|---|---|---|
| E1 | (Z)-3-cyclohexyl-5-{[5-(4-fluorophenyl)thiophen-2-yl]methylene}imidazolidine-2,4-dione | 25% | 60% |
| E2 | (Z)-3-cyclohexyl-5-{[5-(4-fluorophenyl)furan-2-yl]methylene}imidazolidine-2,4-dione | 25% | — |
| E3 | (Z)-3-cyclohexyl-5-{[5-(3-nitrophenyl)furan-2-yl]methylene}imidazolidine-2,4-dione | 25% | — |
| E4 | (Z)-3-cyclohexyl-5-{[(2-fluoropyridin-3-yl)furan-2-yl]methylene}imidazolidine-2,4-dione | 28% | — |
| E5 | (Z)-3-cyclohexyl-5-{[5-(4-methylphenyl)furan-2-yl]methylene}imidazolidine-2,4-dione | 30% | — |

TABLE E-continued

| No. | Compound | 1 μM | 100 nM |
|---|---|---|---|
| E6 | 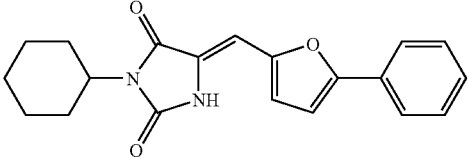<br>(Z)-3-cyclohexyl-5-[(5-phenylfuran-2-yl)methylene]-imidazolidine-2,4-dione | 31% | — |
| E7 | 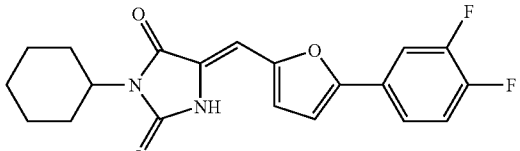<br>(Z)-3-cyclohexyl-5-{[5-(3,4-difluorophenyl)furan-2-yl]methylene}imidazolidine-2,4-dione | 34% | — |
| E8 | 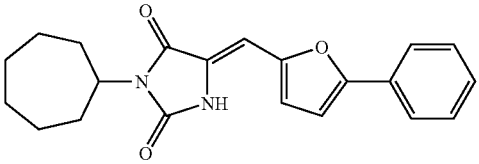<br>(Z)-3-cycloheptyl-5-[(5-phenylfuran-2-yl)methylene]-imidazolidine-2,4-dione | 1% | 31% |
| E9 | 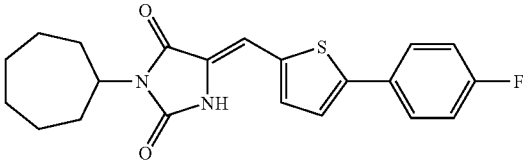<br>(Z)-3-cycloheptyl-5-{[(5-(4-fluorophenyl)thiophen-2-yl]methylene}imidazolidine-2,4-dione | 7% | — |
| E10 | 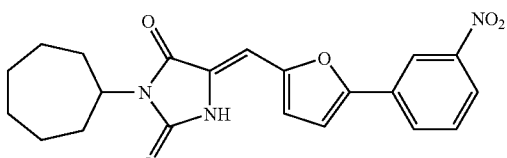<br>(Z)-3-cycloheptyl-5-{[(3-nitrophenyl)furan-2-yl]methylene}imidazolidine-2,4-dione | 8% | — |
| E11 | 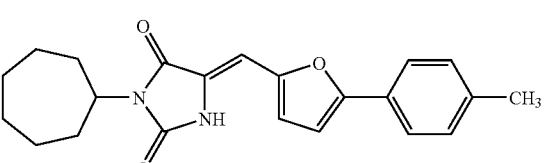<br>(Z)-3-cycloheptyl-5-{[(4-methylphenyl)furan-2-yl]methylene}imidazolidine-2,4-dione | 9% | — |

TABLE E-continued

| No. | Compound | 1 μM | 100 nM |
|---|---|---|---|
| E12 | (Z)-3-cycloheptyl-5-{[(2-fluoropyridin-3-yl)furan-2-yl]methylene}imidazolidine-2,4-dione | 14% | — |
| E13 | (Z)-3-cycloheptyl-5-{[(3,4-ifluorophenyl)furan-2-yl]methylene}imidazolidine-2,4-dione | 16% | — |
| E14 | (Z)-3-cycloheptyl-5-{[5-(2-fluoropyridin-3-yl)furan-2-yl]methylene}-2-thioxothiazolidin-4-one | 36 | 51 |

TABLE F

| No. | Compound | 1000 nM | 100 nM | 10 nM | 1 nM |
|---|---|---|---|---|---|
| F1 | (Z)-3-cyclohexyl-5-[(4'-fluorobiphenyl-4-yl)methylene]-2-thioxothiazolidin-4-one | 3% | 63% | 94% | 74% |
| F2 | (Z)-3-cyclooctyl-5-[(3'-fluorobiphenyl-3-yl)methylene]-2-thioxothiazolidin-4-one | — | 46% | 80% | 77% |

TABLE F-continued

| No. | Compound | 1000 nM | 100 nM | 10 nM | 1 nM |
|---|---|---|---|---|---|
| F3 | 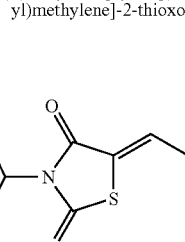<br>(Z)-3-cycloheptyl-5-[(3′-fluorobiphenyl-3-yl)methylene]-2-thioxothiazolidin-4-one | — | 49% | 80% | 69% |
| F4 | 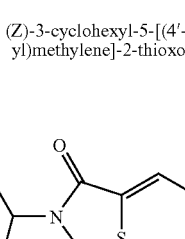<br>(Z)-3-cyclohexyl-5-[(4′-fluorobiphenyl-4-yl)methylene]-2-thioxothiazolidin-4-one | 3% | 57% | 74% | 77% |
| F5 | 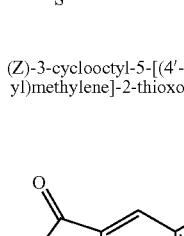<br>(Z)-3-cyclooctyl-5-[(4′-fluorobiphenyl-4-yl)methylene]-2-thioxothiazolidin-4-one | 3% | 37% | 71% | 100% |
| F6 | 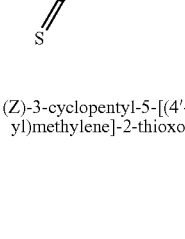<br>(Z)-3-cyclopentyl-5-[(4′-fluorobiphenyl-4-yl)methylene]-2-thioxothiazolidin-4-one | 0% | 63% | 97% | 111% |
| F7 | 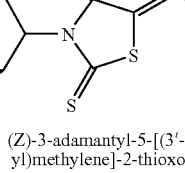<br>(Z)-3-adamantyl-5-[(3′-fluorobiphenyl-3-yl)methylene]-2-thioxothiazolidin-4-one | 43% | 80% | 86% | 74% |

TABLE G

| No. | Compound | H3N2 (Udorn) | H1N9 (G70C) | B (B/Lee/40) |
|---|---|---|---|---|
| G1 | (Z)-3-cyclooctyl-5-{[(4-methylphenyl)furan-2-yl]methylene}-2-thioxothiazolidin-4-one | <1.0 | 1.0 | 1.0 |
| G2 | (Z)-3-(bicyclo[2.2.1]heptan-2-yl-5-{[5-(4-methoxyphenyl)furan-2-yl]methylene}-2-thioxothiazolidin-4-one | <1.0 | 1.0 | 1.0 |
| G3 | (Z)-3-adamantyl-5-{[(4-methylphenyl)furan-2-yl]methylene}-2-thioxothiazolidin-4-one | <1.0 | 1.0 | <1.0 |
| G4 | (Z)-3-cyclohexyl-5-{[(4-methylphenyl)thiophen-2-yl]methylene}-2-thioxoimidazolidin-4-one | 10.0 | 10.0 | 10.0 |

TABLE H

| No. | Compound | 1000 nM | 100 nM | 10 nM | 1 nM |
|---|---|---|---|---|---|
| H1 | (Z)-3-cyclooctyl-5-[(3'-fluorobiphenyl-3-yl)methylene]-2-thioxoimidazolindin-4-one | 0% | 34% | 51% | 57% |

TABLE H-continued

| No. | Compound | 1000 nM | 100 nM | 10 nM | 1 nM |
|---|---|---|---|---|---|
| H2 | 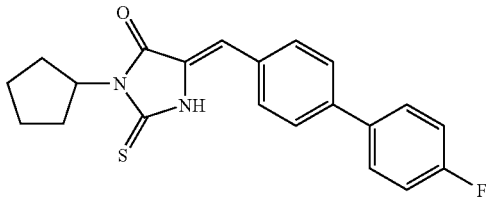 (Z)-3-cyclopentyl-5-[(4'-fluorobiphenyl-4-yl)methylene]-2-thioxoimidazolindin-4-one | 0% | 43% | — | 94% |
| H3 | 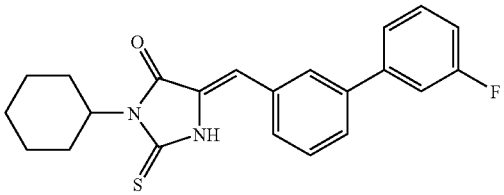 (Z)-3-cyclohexyl-5-[(3'-fluorobiphenyl-3-yl)methylene]-2-thioxoimidazolindin-4-one | 6% | 86% | 86% | 89% |

TABLE I

The $EC_{50}$ value of P25H2 against different influenza virus strains in plaque reduction assay.

| Flu strains | $EC_{50}$ (nM) |
|---|---|
| A/Udorn/72 (H3N2) | 0.4 |
| X-31 (H3N2) | 1 |
| A/PR/8/34 (H1N1) | 0.6 |
| A/NWS/G70C (H1N9) | 1 |
| A/Aichi/68 (H3N2) | 1 |
| B/Lee/40 (type B) | 1 |

The amounts listed in Tables A-I are the percentages of plaques that remain in a sample as compared to the number of plaques when no inhibitors were present (control).

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods are intended to fall within the scope of the appended claims. Thus a combination of steps, elements, components, or constituents may be explicitly mentioned herein; however, all other combinations of steps, elements, components, and constituents are included, even though not explicitly stated.

The invention claimed is:

1. A compound of the following formula:

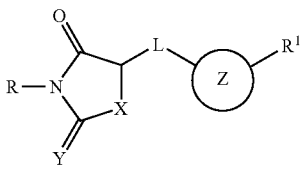

or a pharmaceutically acceptable salt or prodrug thereof, wherein:

X is S or NH;

Y is O or S;

Z is selected from a substituted or unsubstituted 5-member heteroaryl ring, 6-member heteroaryl ring, or phenyl;

$R^1$ is selected from a substituted or unsubstituted aryl or heteroaryl ring; and L is —CH$_2$— or =CH—, wherein when X is S, R is selected from a substituted or unsubstituted fused or bicyclic cycloalkyl ring; and when X is NH, R is selected from a substituted or unsubstituted fused or bicyclic cycloalkyl ring or a substituted or unsubstituted cycloalkyl ring having 3 to 14 carbon ring atoms.

2. The compound of claim 1, wherein R is selected from octahydro-pentalenyl, octahydro-1H-indenyl, decahydronaphthalenyl, decahydroazulenyl, and decahydro-1H-benzo[7]annulenyl.

3. The compound of claim 1, wherein R is selected from bicyclo[1.1.0]-butanyl, bicyclo[1.1.1]pentanyl, bicyclo[2.1.1]hexanyl, bicyclo[2.2.1]heptanyl, bicyclo[3.1.1]heptanyl, bicyclo[2.2.2]octanyl, bicyclo-[3.2.1]octanyl, bicyclo[3.3.2]decanyl, and adamantyl.

4. The compound of claim 1, wherein Z is a substituted or unsubstituted 5-member heteroaryl ring.

5. The compound of claim 1, wherein Z is selected from substituted or unsubstituted furanyl, thiophenyl, pyrazolyl, pyrrolyl, thiazolyl, oxazolyl, or imidazolyl.

6. The compound of claim 1, wherein Z is a substituted or unsubstituted 6-member heteroaryl ring.

7. The compound of claim 1, wherein Z is selected from substituted or unsubstituted phenyl, pyridin-2-yl, pyridin-3-yl, pyridin-4-yl, pyrimidin-2-yl, pyrimidin-4-yl, pyrimidin-5-yl, pyrazinyl, or triazinyl.

8. The compound of claim 1, wherein $R^1$ has the formula:

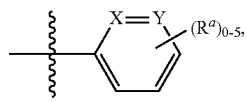

wherein X and Y are each independently selected from CH and N, and $R^a$ represents up to 5 organic radicals, wherein the radicals are substitutions for hydrogen.

9. The compound of claim 1, wherein $R^1$ is substituted by from 1 to 5 organic radicals independently selected from halogen; substituted or unsubstituted haloalkyl; substituted or unsubstituted $C_1$-$C_{12}$ alkyl; substituted or unsubstituted $C_2$-$C_{12}$ alkenyl; substituted or unsubstituted $C_2$-$C_{12}$ alkynyl; substituted or unsubstituted $C_5$-$C_{10}$ aryl; substituted or unsubstituted $C_1$-$C_{12}$ heteroalkyl, substituted or unsubstituted $C_1$-$C_{12}$ heteroalkenyl, substituted or unsubstituted $C_2$-$C_{12}$ heteroalkynyl; $C_1$-$C_9$ substituted or unsubstituted heterocyclic; $C_1$-$C_{11}$ substituted or unsubstituted heteroaryl; substituted or unsubstituted $C_1$-$C_5$ alkoxyalkyl; substituted or unsubstituted $C_2$-$C_5$ alkoxyalkenyl; substituted or unsubstituted $C_2$-$C_5$ alkoxyalkynyl; substituted or unsubstituted $C_1$-$C_5$ aminoalkyl; substituted or unsubstituted $C_2$-$C_5$ aminoalkenyl; substituted or unsubstituted $C_2$-$C_5$ aminoalkynyl; substituted or unsubstituted $C_1$-$C_5$ carboxyalkyl; substituted or unsubstituted $C_2$-$C_5$ carboxyalkenyl; substituted or unsubstituted $C_2$-$C_5$ carboxyalkynyl; substituted or unsubstituted $C_1$-$C_5$ amidoalkyl; substituted or unsubstituted $C_2$-$C_5$ amidoalkenyl; substituted or unsubstituted $C_2$-$C_5$ amidoalkynyl; substituted or unsubstituted $C_1$-$C_5$ cyanoalkyl; substituted or unsubstituted $C_2$-$C_5$ cyanoalkenyl; substituted or unsubstituted $C_2$-$C_5$ cyanoalkynyl; substituted or unsubstituted $C_1$-$C_5$ nitroalkyl; substituted or unsubstituted $C_2$-$C_5$ nitroalkenyl; substituted or unsubstituted $C_2$-$C_5$ nitroalkynyl; substituted or unsubstituted $C_1$-$C_5$ sulfonylalkyl; substituted or unsubstituted $C_2$-$C_5$ sulfonylalkenyl; substituted or unsubstituted $C_2$-$C_5$ sulfonylalkynyl; $C_1$-$C_4$ linear or branched haloalkyl; substituted or unsubstituted alkoxy; halogen; cyano; nitro; or substituted or unsubstituted amino.

10. The compound of claim 1, wherein X is NH and R is a monocyclic ring, a fused cycloalkyl ring, or a bicyclic ring.

11. The compound of claim 1, wherein X is NH and R is selected from cyclopropyl, cyclobutyl, cyclopentyl, cyclononyl, cyclodecyl, cyclohexyl, cycloheptyl, cyclooctyl, cyclododecyl, and cycloundecyl.

12. A composition comprising one or more compounds of claim 1 and a pharmaceutically acceptable carrier.

13. A method for treating an influenza viral infection in a subject, the method comprising administering to the subject an effective amount of the compound of claim 1.

14. The method of claim 13, further comprising administering a second compound or composition, wherein the second compound or composition is an antiviral compound.

15. The method of claim 14 wherein the second compound or composition is a nucleoside or nucleotide reverse transcriptase inhibitor, a non-nucleoside reverse transcriptase inhibitor, a protease inhibitor, an integrase inhibitor, an RNA polymerase inhibitor, a DNA polymerase inhibitor, a kinase inhibitor, an enzyme inhibitor, an entry inhibitor, an assembly inhibitor, a maturation inhibitor, a M2 inhibitor, or a neuraminidase inhibitor.

16. The method of claim 15 wherein the second compound or composition is amantadine, rimantadine, oseltamivir, zanamivir, peramivir, raltegravir, maraviros, enfuviritide, bevirimat, VIVECON®, abacavir, zidovudine, emtricitabine, lamivudine, didanosine, tenofovir disoproxil fumarate, COMBIVIR® (zidovudine+lamivudine), EPZICOM® (abacavir+lamivudine), TRIZIVIR® (abacavir+zidovudine+lamivudine), TRUVADA® (tenofovir disoproxil fumarate+emtricitabine), stavudine, racivir, amdoxovir, apricitabine, elvucitabine, alpha-epibromide, aldesleukin, HIV-1 Immunogen, BAY 50-4798, IR103, etravirine, delavirdine, efavirenz, nevirapine, rilpivirine, amprenavir, tipranavir, indinavir, saquinavir, lopinavir/ritonavir, fosamprenavir, ritonavir, darunavir, atazanavir, nelfinavir, enfuvirtide, maraviroc, vicriviroc, PRO140, TNX-355, raltegravir, elvitegravir, bevirimat, or hydroxyurea.

17. The method of claim 13, wherein the influenza viral infection is influenza A virus.

18. The method of claim 13, wherein the influenza viral infection is influenza B virus.

* * * * *